US008278293B2

(12) United States Patent
Wang et al.

(10) Patent No.: US 8,278,293 B2
(45) Date of Patent: Oct. 2, 2012

(54) DIAZO BICYCLIC SMAC MIMETICS AND THE USES THEREOF

(75) Inventors: Shaomeng Wang, Saline, MI (US); Yuefeng Peng, Ann Arbor, MI (US); Haiying Sun, Ann Arbor, MI (US); Qian Cai, Ann Arbor, MI (US); Zaneta Nikolovska-Coleska, Ann Arbor, MI (US); Jianfeng Lu, Ann Arbor, MI (US); Su Qiu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/159,249

(22) PCT Filed: Apr. 14, 2008

(86) PCT No.: PCT/US2008/060215
§ 371 (c)(1),
(2), (4) Date: Aug. 7, 2008

(87) PCT Pub. No.: WO2008/128171
PCT Pub. Date: Oct. 23, 2008

(65) Prior Publication Data
US 2010/0273812 A1 Oct. 28, 2010

Related U.S. Application Data

(60) Provisional application No. 60/923,348, filed on Apr. 13, 2007.

(51) Int. Cl.
*A61K 31/33* (2006.01)
*C07D 245/00* (2006.01)
(52) U.S. Cl. .................................. 514/183; 540/460
(58) Field of Classification Search ................. None
See application file for complete search history.

(56) References Cited

U.S. PATENT DOCUMENTS

| 8,202,902 B2 * | 6/2012 | Wang et al. ........... 514/483 |
| 2008/0089896 A1 * | 4/2008 | Wang et al. ........... 424/158.1 |
| 2009/0123480 A1 * | 5/2009 | Wang et al. ........... 424/158.1 |
| 2011/0046189 A1 * | 2/2011 | Wang et al. ........... 514/365 |

FOREIGN PATENT DOCUMENTS

| WO | 2005/069894 | 8/2005 |
| WO | 2006010118 | 1/2006 |
| WO | 2007/130626 | 11/2007 |

OTHER PUBLICATIONS

Jantzen and Robinson. Modern Pharmaceutics, 1996, p. 596.*
McCarthy. Nature Reviews Cancer, 2008, 8, p. 1.*
Han. Proceeding of the American Society of Clinical Oncology, 2007, 20, abstract 1657.*
"Prostate Cancer Prevention", http://www.cancer.gov/cancertopics/pdq/prevention/prostate/Patient, accessed Apr. 9, 2010.*
Arellano-:Llamas et al. BMC Cancer, 2006, 6, 256.*
Wu et al., "KILLER/DRS is a DNA damage-inducible p53-regulated death receptor gene" 1997 Nat. Genet. 17:141-143.
Wu et al., "Structural basis of IAP recognition by Smac/DIABLO" 2000 Nature 408:1008.
Yang et al., "Predominant Snppression of Apoptosome by Inhibitor of Apoptosis Protein in Non-Small Cell Lung Cancer H460 Cells: Therapentic Effect of a Novel Polyarginine-conjngated Smac Peptidel" 2003 Cancer Res. 63:831.
Yeh et al., "Requirement for Casper (c-FLIP) in Regulation of Death Receptor-Induced Apoptosis and Embryonic Development" 2000 Immunity 12:533.
Zhang et al., "Relation of TNF-related apoptosis-inducing ligand (TRAIL) receptor and FLICE-inhibitory protein expression to TRAIL-induced apoptosis of melanoma." 1999 Cancer Res. 59:2747.
Lenman et al., "Synthesis of fused 1,2,5-triazepine-1,5-diones and some N@- and N3-substituted derivatives: potential conformational mimetics for cis-peptidyl prolinamides" 1997 J Chemical Society 2297-2311.
International Search Report and Written Opinion dated Oct. 16, 2008, International Patent Application No. PCT/US2008/060215.
Peng, et al., "Design and Synthesis of a 1,5-diazabicyclo[6,3,0] dodecane amino acid derivative as a novel dipeptide reverse-turn mimetic," Tetrahedron Letters 2006, vol. 47, pp. 4769-4770.
Adams et al., "The Bcl-2 Protein Family: Arbiters of Cell Survival" 1998 Science 281:1322.
Arnt et al., "Synthetic Smac/DIABLO Peptides Enhance the Effects of Chemotherapeutic Agents by Binding XIAP and cIAPI in Situ*" 2002 J. Biol. Chem. 277:44236.
Ashkenazi et al., "Death Receptors: Signaling and Modulation" 1998 Science 281:1305.
Asselin et al., "XIAP Regulates Akt Activity and Caspase-3-dependent Cleavage during Cisplatin-induced Apoptosis in Human Ovarian Epithelial Cancer Cells!" 2001 Cancer Res. 61:1862.
Bin et al., "The short splice form of Casper/c-FLIP is a major cellular inhibitor of TRAIL-induced apoptosis" 2002 FEBS Lett 510:37.
Budihardjo et al., "Biochemical Pathways of Caspase Activation During Apoptosis" 1999 Annu. Rev. Cell Dev. Biol. 15:269.
Chai et al., "Structural Basis of Caspase-7 Inhibition by XIAP" 2001 Cell 104:769.
Cheng et al., "SRole of X-linked inhibitor of apoptosis protein in chemoresistance in ovarian cancer: possible involvement of the phosphoinositide-3 kinase/Akt pathway" 2002 Drug Resist. Update 5:131.
Deveraux et al., "X-linked IAP is a direct inhibitor of cell-death proteases" 1997 Nature 388:300-304.
Deveraux et al., "Cleavage of human inhibitor of apoptosis protein XIAP results in fragments with distinct specificities for caspases." 1999 EMBO J. 18:5242.
Deveraux et al., "IAP family proteins—suppressors of apoptosis." 1999 Genes Dev. 13:239.

(Continued)

*Primary Examiner* — Noble Jarrell
(74) *Attorney, Agent, or Firm* — Casimir Jones SC

(57) ABSTRACT

The invention relates to diazo bicyclic mimetics of Smac which function as inhibitors of Inhibitor of Apoptosis Proteins. The invention also relates to the use of these mimetics for inducing apoptotic cell death and for sensitizing cells to inducers of apoptosis.

5 Claims, 28 Drawing Sheets

OTHER PUBLICATIONS

Du et al., "Smac, a mitochondrial protein that promotes cytochrome c-dependent caspase activation by eliminating IAP inhibition." 2000 Cell 102:33.

Ekert et al., "DIABLO promotes apoptosis by removing MIHA/XIAP from processed caspase 9." 2001 J. Cell Biol. 152:483.

French et al., "The TRAIL to selective tumor death." 1999 Nat Med. 5:146.

Fulda et al., "Smac agonists sensitize for Apo2L/TRAIL- or anticancer drug-induced apoptosis and induce regression of malignant glioma in vivo." 2002 Nature Med. 8:808.

Griffith et al., "Intracellular regulation of TRAIL-induced apoptosis in human melanoma cells." 1998 J. Immunol. 161:2833.

Hofmann et al., "Expression of inhibitors of apoptosis (IAP) proteins in non-small cell human lung cancer." 2002 J. Cancer Res. Clin. Onlcol. 128:554.

Holcik et al., "XIAP: apoptotic brake and promising therapeutic target." 2001 Apoptosis 6:253.

Huang et al., "Structural basis of caspase inhibition by XIAP: differential roles of the linker versus the BIR domain." 2001 Cell 104:781-90.

Kataoka et al., "FLIP prevents apoptosis induced by death receptors but not by perforin/granzyme B, chemotherapeutic drugs, and gamma irradiation." 1998 J. Immunol. 161:3936-42.

Kim et al., "Molecular determinants of response to TRAIL in killing of normal and cancer cells." 2000 Clin. Cancer Res. 6:335.

Kischkel et al., "Apo2L/TRAIL-dependent recruitment of endogenous FADD and caspase-8 to death receptors 4 and 5." 2000 Immunity 12:611-20.

Kuang et al., "FADD is required for DR4- and DR5-mediated apoptosis: lack of trail-induced apoptosis in FADD-deficient mouse embryonic fibroblasts." 2000 J. Biol. Chem. 275:25065.

Lacasse et al., "The inhibitors of apoptosis (IAPs) and their emerging role in cancer." 1998 Oncogene 17:3247.

Li et al., "Human Ovarian Cancer and Cisplatin Resistance: Possible Role of Inhibitor of Apoptosis Proteins" 2001 Endocrinology 142:370.

Lowe et al., "Apoptosis in cancer" 2000 Carcinogenesis 21:485.

McEleny et al., "Inhibitors of Apoptosis Proteins in Prostate Cancer Cell Lines" 2002 Prostate 51:133.

Medema et al., "FLICE is, activated by association with the CD95 death-inducing signaling comples (DISC)" 1997 EMBO J. 16:2794.

Muzio et al., "An Induced Proximity Model for Caspase-8 Activation" 1998 J. Biol. Chem. 273:2926.

Ng et al., "X-linked Inhibitor of Apoptosis (XIAP) Blocks Ap02 Ligand/Tumor Necrosis Factor-related Apoptosisinducing Ligand-mediated Apoptosis of Prostate Cancer Cells in the Presence of Mitochondrial Activation: Sensitization by Overexpression of Second Mitochondria-derived Activator of Caspase/Direct IAP-binding Protein with Low pi (Smac/DIABLO)" 2002 Mol. Cancer Ther. 1:1051.

Nicholson, "From bench to clinic with apoptosis-based therapeutic agents" 2000 Nature 407:810.

Nikolovska-Coleska et al., "Development and optimization of a binding assay for the XIAP BIR3 domain using fluorescence polarization" 2004 Anal. Biochem. 332:261-73.

Pan et al., "The Receptor for the Cytotoxic Ligand TRAIL" 1997 Science 276:111.

Pan et al., "An Antagonist Decoy Receptor and a Death Domain-Containing Receptor for TRAIL" 1997 Science 277:815.

Polyak F. and Lubell W.D., "Rigid Dipeptide Mimics: Synthesis of Enantiopure 5.. and 7..Benzyl and 5,7..Dibenzyl Indolizidinone Amino Acids via Enolization and Alkylation of δ-OXO α,ω-DI-[N-(9-(9-phenylfluorenyl)) amino]azelate Esters" J. Org. Chem. 63 5937-5949.

Aggarwal et al., W.D., 2005 Tetrahedron Letters 46 945-947.

Ponder, "Cancer Genetics" 2001 Nature 411:336.

Reed et al., "BCL-2 Family Proteins: Regulators of Cell Death Involved in the Pathogenesis of Cancer and Resistance to Therapy" 1996 J. Cell Biochem. 60:23.

Riedl, 2001 "Structural basis for the inhibition of caspase-3 by XIAP." Cell 104:791.

Salvesen et al., "IAP Proteins: Blocking the Road to Death's Door" 2002 Nat. Rev. Mol. Cell. Biol. 3:401.

Santoro et al., "Birc2 (clap1) regulates endothelial cell integrity and blood vessel homeostasis." 2007 Nature Genetics 39:1397.

Srinivasula et al., "AconseNed XIAP-interaction motif in caspase-9 and SmacIDIABLO regulates caspase activity and apoptosis" 2001 Nature 410:112.

Sun et al., "NMR structure and mutagenesis of the inhibitor-of-apoptosis protein XIAP" 1999 Nature 401:818.

Srinivasa et al., "Molecular Determinants of the Caspase-promoting Activity of SmacIDIABLO and Its Role in the Death Receptor Pathway" 2000 J. Biol. Chem. 275:36152.

Takahashi et al., "A Single BIR Domain of XIAP Sufficient for Inhibiting Caspases" 1998 J. Biol. Chem. 273:7787.

Tamm et al., "Expression and prognostic significance of IAP-family genes in human cancers and myeloid leukemias." 2000 Clin. Cancer Res. 6:1796.

Teitz et al., "Caspase 8 is deleted or silenced preferentially in childhood neuroblastomas with amplification of MYCN" 2000 Nat. Med. 6:529.

Wagenknecht et al., "Expression and biological activity of X-linked inhibitor of apoptosis (XIAP) in human malignant glioma" 1999 Cell Death Differ. 6:370.

Walczak et al., "TRAIL-R2: a novel apoptosis-mediating receptor for TRAIL" 1997 EMBO J. 16:5386.

Walczak et al., "Tumoricidal activity of tumor necrosis factor-related apoptosis-inducing ligand in vivo" 1999 Nat. Med. 5:157.

U.S. Patent Office Office Communication dated Dec. 18, 2009, U.S. Appl. No. 11/800,200.

U.S. Patent Office Communication dated Apr. 1, 2010, U.S. Appl. No. 11/800,220.

U.S. Patent Office Communication dated Nov. 8, 2010, U.S. Appl. No. 11/800,220.

U.S. Patent Office Notice of Allowance dated Feb. 11, 2011, U.S. Appl. No. 11/800,220.

U.S. Patent Office Communication dated Jun. 13, 2011, U.S. Appl. No. 12/270,374.

* cited by examiner

SEQUENCE LISTING
<160> NUMBER OF SEQ ID NOS: 2
<210> SEQ ID NO 1
<211> LENGTH: 4
<212> TYPE: PRT
<213> ORGANISM: Artificial Sequence
<220> FEATURE:
<223> OTHER INFORMATION: Synthetic
<400> SEQUENCE: 1
Ala Val Pro Ile
1
<210> SEQ ID NO 2
<211> LENGTH: 4
<212> TYPE: PRT
<213> ORGANISM: Artificial Sequence
<220> FEATURE:
<223> OTHER INFORMATION: Synthetic
<400> SEQUENCE: 2
Ala Thr Pro Phe
1

US 8,278,293 B2

DIAZO BICYCLIC SMAC MIMETICS AND THE USES THEREOF

CROSS REFERENCE TO RELATED APPLICATIONS

The present application is a 371 national stage non-provisional application of pending International Patent Application No. PCT/US08/060215, international filing date Apr. 14, 2008, which claims the benefit of expired U.S. provisional application No. 60/923,348 filed Apr. 13, 2007, both of which are incorporated herein by reference in their entireties.

STATEMENT REGARDING FEDERALLY SPONSORED RESEARCH OR DEVELOPMENT

This invention was made with government support under Grant No. RO1CA109025 awarded by the National Institute of Health. The government has certain rights in the invention.

BACKGROUND OF THE INVENTION

1. Field of the Invention

This invention is in the field of medicinal chemistry. In particular, the invention relates to conformationally constrained mimetics of the N-terminal sequence of Smac which function as inhibitors of Inhibitor of Apoptosis Proteins. The invention also relates to the use of these mimetics for inducing or sensitizing cells to the induction of apoptotic cell death.

2. Related Art

The aggressive cancer cell phenotype is the result of a variety of genetic and epigenetic alterations leading to deregulation of intracellular signaling pathways (Ponder, Nature 411:336 (2001)). The commonality for all cancer cells, however, is their failure to execute an apoptotic program, and lack of appropriate apoptosis due to defects in the normal apoptosis machinery is a hallmark of cancer (Lowe et al., Carcinogenesis 21:485 (2000)). Most current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., Carcinogenesis 21:485 (2000); Nicholson, Nature 407: 810 (2000)). Accordingly, current and future efforts towards designing and developing new molecular target-specific anticancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class of regulators is the Bcl-2 family of proteins, as exemplified by two potent anti-apoptotic molecules, Bcl-2 and Bcl-XL proteins (Adams et al., Science 281:1322 (1998); Reed, Adv. Pharmacol. 41:501 (1997); Reed et al., J. Cell. Biochem. 60:23 (1996)). Therapeutic strategies for targeting Bcl-2 and Bcl-XL in cancer to restore cancer cell sensitivity and overcome resistance of cancer cells to apoptosis have been extensively reviewed (Adams et al., Science 281:1322 (1998); Reed, Adv. Pharmacol. 41:501 (1997); Reed et al., J. Cell. Biochem. 60:23 (1996)). Several laboratories are interested in designing small molecule inhibitors of Bcl-2 and Bcl-XL.

The second class of central negative regulators of apoptosis is the inhibitor of apoptosis proteins (IAPs) (Deveraux et al., Genes Dev. 13:239 (1999); Salvesen et al., Nat. Rev. Mol. Cell. Biol. 3:401 (2002)). This class includes proteins such as XIAP, cIAP-1, cIAP-2, ML-IAP, HIAP, KIAP, TSIAP, NAIP, survivin, livin, ILP-2, apollon, and BRUCE. IAP proteins potently suppress apoptosis induced by a large variety of apoptotic stimuli, including chemotherapeutic agents, radiation, and immunotherapy in cancer cells.

X-linked IAP (XIAP) is the most potent inhibitor in suppressing apoptosis among all of the IAP members (Holcik et al., Apoptosis 6:253 (2001); LaCasse et al., Oncogene 17:3247 (1998); Takahashi et al., J. Biol. Chem. 273:7787 (1998); Deveraux et al., Nature 388:300 (1997); Sun et al., Nature 401:818 (1999); Deveraux et al., EMBO J. 18:5242 (1999); Asselin et al., Cancer Res. 61:1862 (2001)). XIAP plays a key role in the negative regulation of apoptosis in both the death receptor-mediated and the mitochondria-mediated pathways. XIAP functions as a potent endogenous apoptosis inhibitor by directly binding and potently inhibiting three members of the caspase family of enzymes, caspase-3, -7, and -9 (Takahashi et al., J. Biol. Chem. 273:7787 (1998); Deveraux et al., Nature 388:300 (1997); Sun et al., Nature 401:818 (1999); Deveraux et al., EMBO J. 18:5242 (1999); Asselin et al., Cancer Res. 61:1862 (2001); Riedl et al., Cell 104:791 (2001); Chai et al., Cell 104:769 (2001); Huang et al., Cell 104:781 (2001)). XIAP contains three baculovirus inhibitor of apoptosis repeat (BIR) domains as well as a C-terminal RING finger. The third BIR domain (BIR3) selectively targets caspase-9, the initiator caspase in the mitochondrial pathway, whereas the linker region between BIR1 and BIR2 inhibits both caspase-3 and caspase-7 (Salvesen et al., Nat. Rev. Mol. Cell. Biol. 3:401 (2002)). While binding to XIAP prevents the activation of all three caspases, it is apparent that the interaction with caspase-9 is the most critical for its inhibition of apoptosis (Ekert et al., J. Cell Biol. 152:483 (2001); Srinivasula et al., Nature 410:112 (2001)). Because XIAP blocks apoptosis at the down-stream effector phase, a point where multiple signaling pathways converge, strategies targeting XIAP may prove to be especially effective to overcome resistance of cancer cells to apoptosis (Fulda et al., Nature Med. 8:808 (2002); Arnt et al., J. Biol. Chem. 277:44236 (2002)).

Although the precise role of XIAP in each type of cancer is far from completely understood, evidence is mounting to indicate that XIAP is widely overexpressed in many types of cancer and may play an important role in the resistance of cancer cells to a variety of current therapeutic agents (Holcik et al., Apoptosis 6:253 (2001); LaCasse et al., Oncogene 17:3247 (1998)).

XIAP protein was found to be expressed in most of the NCI 60 human cancer cell lines (Tamm et al., Clin. Cancer Res. 6:1796 (2000)). Analysis of tumor samples in 78 previously untreated patients showed that those with lower levels of XIAP had significantly longer survival (Tamm et al., Clin. Cancer Res. 6:1796 (2000)). XIAP was found to be expressed in human malignant glioma (Wagenknecht et al., Cell Death Differ. 6:370 (1999); Fulda et al., Nature Med. 8:808 (2002)). XIAP was found to be expressed in human prostate cancer cells and blocks Apo2 ligand/tumor necrosis factor-related apoptosis inducing ligand-mediated apoptosis of prostate cancer cells in the presence of mitochondrial activation (McEleny et al., Prostate 51:133 (2002); Ng et al., Mol. Cancer. Ther. 1:1051 (2002)). XIAP is overexpressed in non-small cell lung cancer (NSCLC) in patients and has been implicated in pathogenesis of NSCLC (Hofmann et al., J.

Cancer Res. Clin. Oncol. 128:554 (2002)). Expression of XIAP and lack of down-regulation of XIAP upon treatment with cisplatin have been implicated in cisplatin resistance of human ovarian cancer (Li et al., Endocrinology 142:370 (2001); Cheng et al., Drug Resist. Update 5:131 (2002)). Taken together, these data suggest that XIAP may play an important role in resistance of several human cancers to current therapeutic agents.

Integrity of the blood vessel wall is essential for vascular homeostasis and organ function. A dynamic balance between endothelial cell survival and apoptosis contributes to this integrity during vascular development and pathological angiogenesis. It has been shown that cIAP-1 is essential for maintaining endothelial cell survival and blood vessel homeostasis during vascular development (Santoro et al., Nature Genetics 39:1397 (2007). As such, cIAP-1 may play an important role in the control of angiogenesis and blood vessel homeostasis during embryogenesis, regeneration and tumorigenesis.

Apoptosis is not a single process, rather, it is involved with a number of different, sometimes interconnected, signaling pathways leading to cell degradation. The pathways involved in a particular form of apoptosis depend on many factors, such as the insult or insults that initiate the process. Other factors include the activation or overactivation of specific receptors, such as the activation of "death" receptors by tumor necrosis factor alpha (TNFα), tumor necrosis factor-related apoptosis-inducing ligand (TRAIL or Apo2L), or FAS ligand. Another determining factor is the type of cell which is involved, since different signaling pathways are shown for so called type I and type II cells after Fas or TNFα receptor activation.

TRAIL (Apo2L) has been shown to be a selective and potent inducer of apoptosis in cancer cells (but not normal cells) upon binding to either of two pro-apoptotic TRAIL receptors, TRAIL-R1 (or DR4) (Pan et al., Science 276:111 (1997)) or TRAIL-R2 (KILLER, or DR5) (Wu et al., Nat. Genet. 17:141-143 (1997); Pan et al., Science 277:815 (1997); Walczak et al., EMBO J. 16:5386 (1997)). Activation of the pro-apoptotic death receptors by TRAIL induces the formation of death inducing signaling complex (DISC), which consists of receptor FADD as an adaptor (Kischkel et al., Immunity 12:611 (2000); Kuang et al., J. Biol. Chem. 275:25065 (2000)), and caspase-8 as an initiator caspase. Once DISC is formed, caspase-8 is auto-processed and activated by induced proximity (Medema et al., EMBO J. 16:2794 (1997); Muzio et al., J. Biol. Chem. 273:2926 (1998)).

TRAIL has generated significant interest as a potential cancer therapeutic (French et al., Nat. Med. 5:146 (1999)) because of its selective targeting of cancer cells, whereas most normal cells appear to be resistant to TRAIL (Ashkenazi et al., Science 281:1305 (1998); Walczak et al., Nat. Med. 5:157 (1999)). Systemic administration of TRAIL has proven to be safe and effective at killing breast or colon xenografted tumors and prolonging survival in mice (Walczak et al., Nat. Med. 5:157 (1999)). Although TRAIL can specifically kill many types of cancer cells, many others display TRAIL-resistance (Kim et al., Clin. Cancer Res. 6:335 (2000); Zhang et al., Cancer Res. 59:2747 (1999)). In addition, cancer cells have been killed by application of antibodies (monoclonal or polyclonal) that specifically recognize either TRAIL-R1 or TRAIL-R2.

Numerous mechanisms have been identified as potential factors responsible for TRAIL-resistance. Such mechanisms exist at a number of levels, including at the receptor level, mitochondria level, post-mitochondria level, and at the DISC level. For example, loss of caspase-8 expression (Teitz et al., Nat. Med. 6:529 (2000); Griffith et al., J. Immunol. 161:2833 (1998)), or high expression of the cellular FLICE inhibitor protein (cFLIP) (Kim et al., Clin. Cancer Res. 6:335 (2000); Zhang et al., Cancer Res. 59:2747 1999; Kataoka et al., J. Immunol. 161:3936 (1998)) make cancer cells resistant to TRAIL. Yeh et al. have shown that cFLIP-deficient embryonic mouse fibroblasts are particularly sensitive to receptor-mediated apoptosis (Yeh et al., Immunity 12:533 (2000)). Several splice variants of cFLIP are known, including a short splice variant, cFLIP-S, and a longer splice variant, cFLIP-L. It has been shown that cFLIP-deficient embryonic mouse fibroblasts become resistant to TRAIL-induced apoptosis as a result of retroviral-mediated transduction of cFLIP-S (Bin et al., FEBS Lett. 510:37 (2002)).

Although TRAIL represents a potentially promising candidate for tumor-selective death receptor activation (i.e., it induces apoptosis preferentially in tumor cells but not in normal tissues), many cancer cells are resistant to apoptosis-inducing drugs, as discussed above. As a result, treatment with such drugs often requires co-treatment with irradiation and/or cytotoxic chemicals to achieve a therapeutic effect. However, both radiation and chemotherapy have significant side effects, and are generally avoided if possible.

Thus, a need exists for an agent that can selectively and efficiently sensitize tumor cells to selective, apoptosis-inducing drugs such as TRAIL or TRAIL receptor antibodies, without also sensitizing surrounding normal cells. Such an agent would also be useful for reducing or preventing the drug resistance commonly associated with the use of receptor-mediated apoptotic cancer drugs, thus improving their effectiveness and eliminating the need for combination therapies.

Recently, Smac/DIABLO (second mitochondria-derived activator of caspases) was identified as a protein released from mitochondria into the cytosol in response to apoptotic stimuli (Budihardjo et al., Annu. Rev. Cell Dev. Biol. 15:269 (1999); Du et al., Cell 102:33 (2000)). Smac is synthesized with an N-terminal mitochondrial targeting sequence that is proteolytically removed during maturation to the mature polypeptide. Smac was shown to directly interact with XIAP and other IAPs and to disrupt their binding to caspases and facilitate caspase activation. Smac is a potent endogenous inhibitor of XIAP.

High resolution, experimental three-dimensional (3D) structures of the BIR3 domain of XIAP in complex with Smac protein and peptide have recently been determined (Sun et al., J. Biol. Chem. 275:36152 (2000); Wu et al., Nature 408:1008 (2000)) (FIG. 1). The N-terminal tetrapeptide of Smac (Ala-Val-Pro-Ile, or AVPI (SEQ ID NO:1)) recognizes a surface groove on the BIR3 domain of XIAP through several hydrogen-bonding interactions and van der Waals contacts. The interaction between BIR3 and caspase-9 has also been shown to involve four residues (Ala-Thr-Pro-Phe, or ATPF (SEQ ID NO:2)) on the amino terminus of the small subunit of caspase-9 to the same surface groove on the BIR3 domain. Several recent studies have convincingly demonstrated that Smac promotes the catalytic activity of caspase-9 by competing with caspase-9 for the same binding groove on the surface of the BIR3 domain (Ekert et al., J. Cell Biol. 152:483 (2001); Srinivasula et al., Nature 410:112 (2001)).

Unlike most protein-protein interactions, the Smac-XIAP interaction is mediated by only four amino acid residues on the Smac protein and a well-defined surface groove on the BIR3 domain of XIAP. The $K_d$ value of Smac peptide AVPI (SEQ ID NO:1) to XIAP BIR3 ($K_d$=0.4 µM) is essentially the same as the mature Smac protein ($K_d$=0.42 µM). This well-defined interaction site is ideal for the design of non-peptide, drug-like small molecules that mimic the binding of Smac to XIAP.

A cell permeable Smac peptide, which consists of the first four amino acid residues (AVPI (SEQ ID NO:1)) of the N-terminus of Smac tethered to a carrier peptide to facilitate intracellular delivery, was recently shown to sensitize various tumor cells in vitro and malignant glioma cells in vivo to apoptosis induced by death receptor ligation or cytotoxic drugs (Fulda et al., *Nature Med.* 8:808 (2002)). Importantly, this Smac peptide strongly enhanced the anti-tumor activity of Apo2L/TRAIL in an intracranial malignant glioma xenograft model in vivo. Complete eradication of established tumors and survival of mice was only achieved upon combined treatment with Smac peptides and Apo2L/TRAIL. Of significance, Smac peptide does not have detectable toxicity to normal brain tissue.

A second recent independent study also showed that peptides consisting of the first four to eight amino acid residues of the N-terminus of Smac tethered to a different carrier peptide enhanced the induction of apoptosis and the long term anti-proliferative effects of diverse chemotherapeutic drugs, including paclitaxel, etoposide, SN-38, and doxorubicin in MCF-7 and other human breast cancer cell lines (Arnt et al., *J. Biol. Chem.* 277:44236 (2002). This study conclusively showed that XIAP and cIAP-1 are the primary molecular targets for these peptides in cells.

A third study showed that a Smac peptide of the first seven N-terminal residues tethered to polyarginine restored the apoptosome activity and reversed the apoptosis resistance in non-small cell lung cancer H460 cells (Yang et al., *Cancer Res.* 63:831 (2003)). XIAP was shown to be responsible for the defect in apoptosome activity and suppression of caspase activity in H460 cells. When used in combination with chemotherapy, the cell-permeable Smac peptide regressed tumor growth in vivo with little murine toxicity. Taken together, these recent independent studies strongly suggest that a potent, stable, cell-permeable Smac mimetic may have great therapeutic potential for the treatment of human breast cancer and other types of cancer.

Peptide-based inhibitors are useful tools to elucidate the anti-apoptotic function of IAPs and the role of IAPs in response of cancer cells to chemotherapeutic agents. But peptide-based inhibitors in general have intrinsic limitations as potentially useful therapeutic agents. These limitations include their poor cell-permeability and poor in vivo stability. Indeed, in these three published studies using Smac-based peptide inhibitors, the peptides had to be fused to carrier peptides to make them relatively cell-permeable.

To overcome the intrinsic limitations of peptide-based inhibitors, the present invention involves the design of conformationally constrained Smac mimetics.

SUMMARY OF THE INVENTION

It is generally accepted that the inability of cancer cells or their supporting cells to undergo apoptosis in response to genetic lesions or exposure to inducers of apoptosis (such as anticancer agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is increased expression and accumulation of IAPs.

The present invention contemplates that exposure of animals suffering from cancer or other hyperproliferative disorders or diseases associated with dysregulation of apoptosis to therapeutically effective amounts of drug(s) (e.g., small molecules) that inhibit the function(s) of IAPs will kill the diseased cells or supporting cells outright (those cells whose continued survival is dependent on the overactivity or overexpression of IAPs) and/or render such cells as a population more susceptible to the cell death-inducing activity of cancer therapeutic drugs or radiation therapies. The present invention contemplates that inhibitors of IAPs satisfy an unmet need for the treatment of multiple cancer types, either when administered as monotherapy to induce apoptosis in cancer cells dependent on IAP function, or when administered in a temporal relationship with other cell death-inducing cancer therapeutic drugs or radiation therapies so as to render a greater proportion of the cancer cells or supportive cells susceptible to executing the apoptosis program compared to the corresponding proportion of cells in an animal treated only with the cancer therapeutic drug or radiation therapy alone.

The present invention also contemplates that treatment of animals suffering from endothelial cell-associated diseases (e.g., tumor angiogenesis, retinopathies and atherosclerosis) with therapeutically effective amounts of drug(s) (e.g., small molecules) that inhibit the function(s) of IAPs (e.g., cIAP-1) may prevent or inhibit angiogenesis and disrupt blood vessel homeostasis during vascular development in pathological conditions. Particular disorders that may be treated with the compounds of the invention include macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma and hypertrophic scars.

Applicants have found that insertion of $NR^5$ into the bicyclic ring system has certain unexpected influence on binding to XIAP as compared to carbocyclic analogs (e.g., SM-122) (Chart 1). For example, the binding affinity to XIAP BIR3 and the cellular activity in MDA-MB-231 and SK-OV-3 cancer cell lines of SM-245P3 ($R^5$=Me) and SM-246P($R^5$=Bn) are less than that of SM-122. Surprisingly, the binding affinity to XIAP BIR3 and the cellular activity in MDA-MB-231 and SK-OV-3 cancer cell lines of SM-337 ($R^5$=COCH$_2$Ph) and SM-406 ($R^5$=COCH$_2$CH(CH$_3$)$_2$ are equal to or better than that of SM-122. In addition to certain biological properties, Applicants have found that SM-406 and other related analogs display an unexpected improvement in oral bioavailability relative to SM-122.

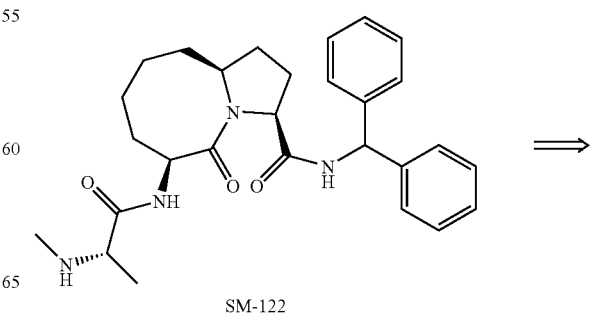

SM-122

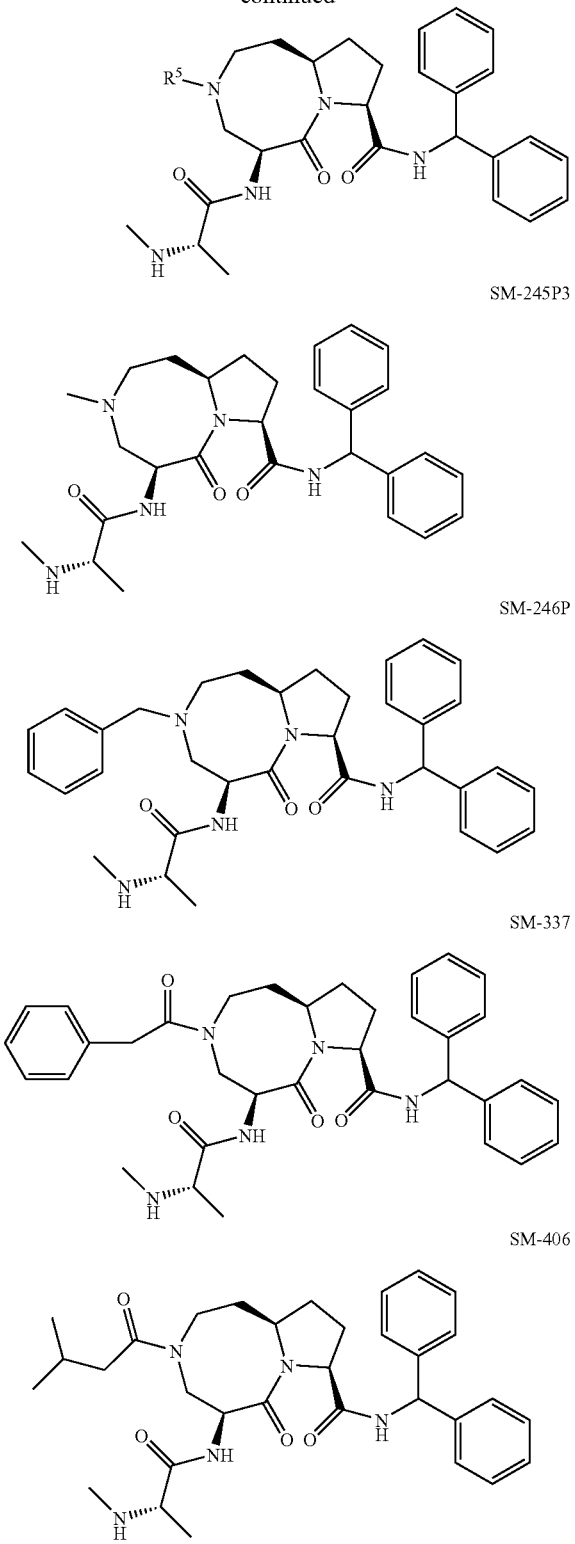

SM-245P3

SM-246P

SM-337

SM-406

Applicants have also found that compounds of the present invention when combined with other anticancer agents (e.g., Tykerb®, taxotere, gemcitabine, mitoxantrone, etoposide) display unexpected improvements in in vitro activity in cancer cell lines. In addition, Applicants have found that compounds of the present invention when combined with other anticancer agents (e.g., Tykerb®, taxotere, gemcitabine) display surprising reductions in mean tumor volume in in vivo cancer xenograph models. Thus, in certain embodiments of the invention, combination treatment of animals with a therapeutically effective amount of a compound of the present invention and a course of an anticancer agent or radiation produces a greater tumor response and clinical benefit in such animals compared to those treated with the compound or anticancer drugs/radiation alone. Put another way, because the compounds of the present invention lower the apoptotic threshold of all cells that express IAPs, the proportion of cells that successfully execute the apoptosis program in response to the apoptosis inducing activity of anticancer drugs/radiation is increased. Alternatively, the compounds of the present invention can be used to allow administration of a lower, and therefore less toxic and more tolerable, dose of an anticancer agent and/or radiation to produce the same tumor response/clinical benefit as the conventional dose of the anticancer agent/radiation alone. Since the doses for all approved anticancer drugs and radiation treatments are known, the present invention contemplates the various combinations of them with the compounds of the present invention. Also, since the compounds of the present invention act at least in part by inhibiting IAPs, the exposure of cancer cells and supporting cells to therapeutically effective amounts of the compounds can be temporally linked to coincide with the attempts of cells to execute the apoptosis program in response to the anticancer agent or radiation therapy. Thus, in some embodiments, administering the compositions of the present invention in connection with certain temporal relationships, provides especially efficacious therapeutic practices.

The present invention relates to Smac mimetics that are useful for inhibiting the activity of IAP proteins and inter alia increasing the sensitivity of cells to inducers of apoptosis. In one particular embodiment, the Smac mimetics are compounds of formula I:

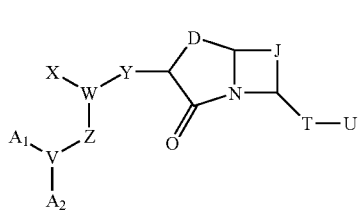

I wherein:
$A_1$ and $A_2$ are independently selected from the group consisting of hydrogen and optionally substituted alkyl, wherein $A_2$ is absent when V is O;
V is selected from the group consisting of N, CH and O;
W is selected from the group consisting of CH and N;
X is selected from the group consisting of hydrogen and optionally substituted $C_{1-3}$ alkyl;
Y is selected from the group consisting of CONH, NHCO, C(O)O, OC(O), $(CH_2)_{1-3}$, wherein one or more $CH_2$ groups can be replaced by O, S, or $NR^1$, optionally substituted aryl and optionally substituted heteroaryl;
Z is $(CR^1R^2)_r$;
D is $(CR^1R^2)_n$—$NR^5$—$(CR^3R^4)_m$;
J is selected from the group consisting of optionally substituted alkylenyl and $(CR^1R^2)_p$—$R^6$—$(CR^3R^4)_q$;
T is selected from the group consisting of C=O, C=S, C=$NR^1$, S, S=O, $SO_2$, O, $NR^1$, $CR^1R^2$, optionally substituted carbocyclic, optionally substituted heterocyclic, optionally substituted aryl and optionally substituted heteroaryl;

U is selected from the group consisting of H, $NR^1R^2$, $N(R^1)COR^7$, $OR^1$, $SR^1$, optionally substituted alkyl, optionally substituted aryl and heteroaryl;

n, m, p and q are independently selected from the group consisting of 0-5;

r is 0-3;

each $R^1$, $R^2$, $R^3$ and $R^4$ are independently selected from the group consisting of hydrogen, optionally substituted alkyl, optionally substituted carbocyclic, optionally substituted heterocyclic, optionally substituted aryl and optionally substituted heteroaryl;

$R^5$ is selected from the group consisting of hydrogen, optionally substituted alkyl, optionally substituted heteroalkyl, optionally substituted carbocyclic, optionally substituted heterocyclic, optionally substituted aryl, optionally substituted heteroaryl and $COR^7$;

$R^6$ is selected from the group consisting of O, S, $NR^1$, $CR^1R^2$, C=O, C=S and C=$NR^1$; and $R^7$ is selected from the group consisting of hydrogen, optionally substituted alkyl, optionally substituted carbocyclic, optionally substituted heterocyclic, optionally substituted aryl and optionally substituted heteroaryl; or a pharmaceutically acceptable salt or prodrug thereof.

In another embodiment, Smac mimetics are compounds having the general Formula II:

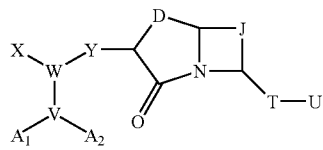

II wherein:

$A_1$ and $A_2$ are independently selected from the group consisting of hydrogen and optionally substituted alkyl, wherein $A_2$ is absent when V is O;

V is selected from the group consisting of N, CH and O;

W is selected from the group consisting of CH and N;

X is optionally substituted $C_{1-3}$ alkyl;

Y is selected from the group consisting of CONH, C(O)O, $(CH_2)_{1-3}$ wherein one or more $CH_2$ groups can be replaced by O, S, or $NR^1$, optionally substituted aryl and optionally substituted heteroaryl;

D is $(CR^1R^2)_n$—$NR^5$—$(CR^3R^4)_m$;

J is selected from the group consisting of optionally substituted alkylenyl and $(CR^1R^2)_p$—$R^6$—$(CR^3R^4)_q$;

T is selected from the group consisting of C=O, C=S, C=$NR^1$, S, O, $NR^1$, $CR^1R^2$, optionally substituted carbocyclic, optionally substituted heterocyclic, optionally substituted aryl and optionally substituted heteroaryl;

U is selected from the group consisting of H, $NR^1R^2$, $OR^1$, $SR^1$, optionally substituted alkyl and optionally substituted aryl;

n, m, p and q are independently selected from 0-5;

each $R^1$, $R^2$, $R^3$ and $R^4$ are independently selected from the group consisting of hydrogen, optionally substituted alkyl, optionally substituted carbocyclic, optionally substituted heterocyclic, optionally substituted aryl and optionally substituted heteroaryl;

$R^5$ is selected from the group consisting of hydrogen, optionally substituted alkyl, optionally substituted heteroalkyl, optionally substituted carbocyclic, optionally substituted heterocyclic, optionally substituted aryl, optionally substituted heteroaryl and $COR^7$;

$R^6$ is selected from the group consisting of O, S, $NR^1$, $CR^1R^2$, C=O, C=S and C=$NR^1$;

$R^7$ is selected from the group consisting of hydrogen, optionally substituted alkyl, optionally substituted carbocyclic, optionally substituted heterocyclic, optionally substituted aryl and optionally substituted heteroaryl;

or a pharmaceutically acceptable salt or prodrug thereof.

In one embodiment, the optional substituents do not include carboxylic acid, cycloalkyl optionally substituted with one or more alkyl, halo, hydroxyl or haloalkyl groups, or aryl optionally substituted with an aryl group, and an optionally substituted heterocyclic group does not include oxopiperizinyl.

In another particular embodiment, Smac mimetics are compounds of Formula III:

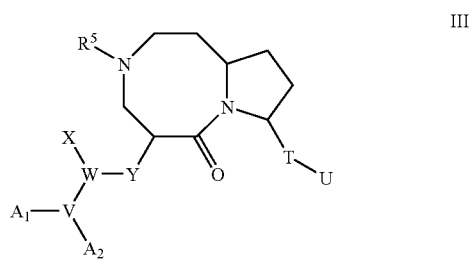

III wherein $A_1$, $A_2$, V, W, X, Y, $R^5$, T and U have the meanings as described above for Formula I; or pharmaceutically acceptable salts or prodrugs thereof.

In another particular embodiment, Smac mimetics are compounds of Formula IV:

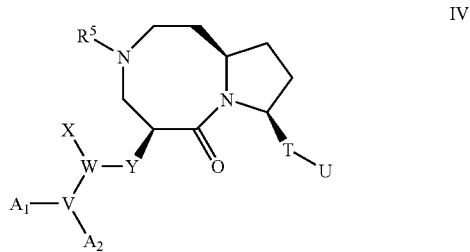

IV wherein $A_1$, $A_2$, V, W, X, Y, $R^5$, T and U have the meanings as described above for Formula I; or a pharmaceutically acceptable salt or prodrug thereof.

In another particular embodiment, Smac mimetics are compounds of Formula V:

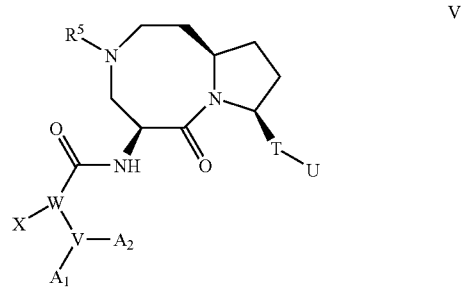

V wherein $A_1$, $A_2$, V, W, X, $R^5$, T and U have the meanings as described above for Formula I; or a pharmaceutically acceptable salt or prodrug thereof.

In another particular embodiment, Smac mimetics are compounds of Formula VI:

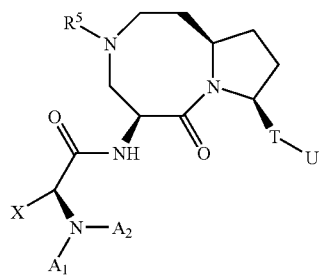

VI wherein $A_1$, $A_2$, $R^5$, T and U have the meanings as described above for Formula I, and X is optionally substituted alkyl; or a pharmaceutically acceptable salt or prodrug thereof.

In another particular embodiment, Smac mimetics are compounds of Formula VII:

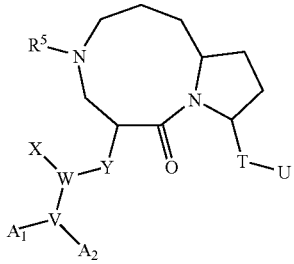

VII wherein $A_1$, $A_2$, V, W, X, Y, $R^5$, T and U have the same meanings as described above for Formula I; or a pharmaceutically acceptable salt or prodrug thereof.

In another particular embodiment, Smac mimetics are compounds of Formula VIII:

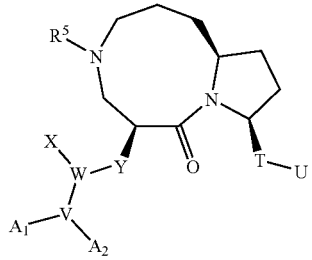

VIII wherein $A_1$, $A_2$, V, W, X, Y, $R^5$, T and U have the same meanings as described above for Formula I; or a pharmaceutically acceptable salt or prodrug thereof.

In another particular embodiment, Smac mimetics are compounds of Formula IX:

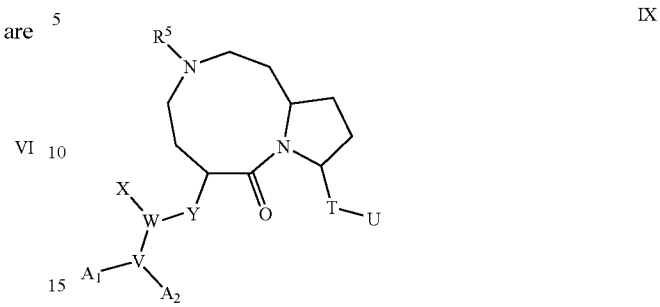

IX wherein $A_1$, $A_2$, V, W, X, Y, $R^5$, T and U have the same meanings as described above for Formula I; or a pharmaceutically acceptable salt or prodrug thereof.

In another particular embodiment, Smac mimetics are compounds of Formula X:

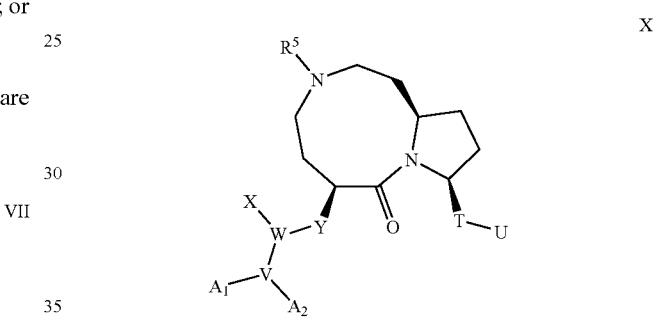

X wherein $A_1$, $A_2$, V, W, X, Y, $R^5$, T and U have the same meanings as described above for Formula I; or a pharmaceutically acceptable salt or prodrug thereof.

The invention relates to compounds represented by Formulae I-X which are inhibitors of IAP proteins. The invention relates to the use of the compounds of the invention to induce apoptosis in cells and inhibit angiogenesis. The invention also relates to the use of the compounds of the invention for sensitizing cells to inducers of apoptosis. The compounds are useful for the treatment, amelioration, or prevention of disorders responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those which are chemoresistant, radiation resistant, hormone resistant, and the like). In other embodiments, the compounds can be used to treat hyperproliferative diseases characterized by overexpression of IAPs. In other embodiments, the compounds can be used as a method of preventing or inhibiting angiogenesis in animals in need thereof.

The present invention provides pharmaceutical compositions comprising compounds of Formulae I-X in a therapeutically effective amount to induce apoptosis in cells or to sensitize cells to inducers of apoptosis.

The invention further provides kits comprising a compound of Formula I and instructions for administering the compound to an animal. The kits may optionally contain other therapeutic agents, e.g., anticancer agents or apoptosis-modulating agents.

The present invention also provides a process for preparing a compound of Formula XI

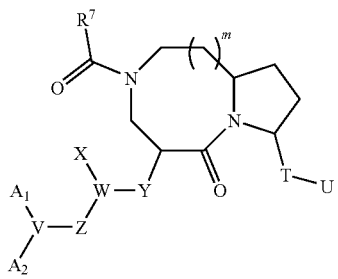

XI wherein
$A_1$ and $A_2$ are independently selected from the group consisting of hydrogen and optionally substituted alkyl, wherein $A_2$ is absent when V is O;
V is selected from the group consisting of N, CH and O;
W is selected from the group consisting of CH and N;
X is selected from the group consisting of hydrogen and optionally substituted $C_{1-3}$ alkyl;
Y is selected from the group consisting of CONH, NHCO, C(O)O, OC(O), $(CH_2)_{1-3}$, wherein one or more $CH_2$ groups can be replaced by O, S, or $NR^1$, optionally substituted aryl and optionally substituted heteroaryl;
Z is $(CR^1R^2)_r$;
T is selected from the group consisting of C=O, C=S, C=NR$^1$, S, S=O, SO$_2$, O, NR$^1$, CR$^1$R$^2$, optionally substituted carbocyclic, optionally substituted heterocyclic, optionally substituted aryl and optionally substituted heteroaryl;
U is selected from the group consisting of H, $NR^1R^2$, $N(R^1)COR^7$, $OR^1$, $SR^1$, optionally substituted alkyl, optionally substituted aryl and heteroaryl;
m is 1 or 2;
r is 0-3;
each $R^1$, $R^2$, $R^3$ and $R^4$ are independently selected from the group consisting of hydrogen, optionally substituted alkyl, optionally substituted carbocyclic, optionally substituted heterocyclic, optionally substituted aryl and optionally substituted heteroaryl; and
$R^7$ is selected from the group consisting of hydrogen, optionally substituted alkyl, optionally substituted carbocyclic, optionally substituted heterocyclic, optionally substituted aryl and optionally substituted heteroaryl;
comprising condensing a compound of Formula XII

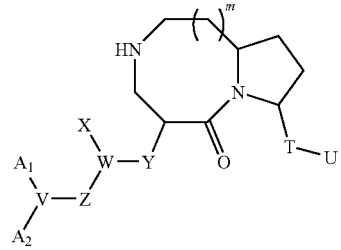

XII wherein $A_1$, $A_2$, V, W, X, Y, Z, T, U and m have the meanings described above for Formula XI,
with $R^7$CO-L, wherein:
$R^7$ is selected from the group consisting of hydrogen, optionally substituted alkyl, optionally substituted carbocyclic, optionally substituted heterocyclic, optionally substituted aryl and optionally substituted heteroaryl; and
L is a leaving group, to form a compound of Formula XI.
The present invention also provides a process for the preparation of a compound of Formula XIX

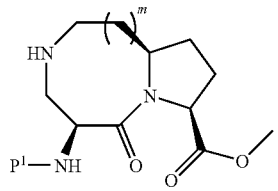

XIX wherein m is 1 or 2, and $P^1$ is an amine protecting group comprising:
a) condensing a compound of Formula XX

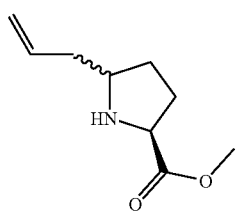

XX with a compound of formula XXI,

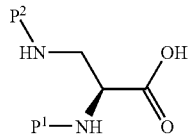

XXI wherein $P^1$ and $P^2$ are amine protecting groups and $P^1$ does not equal $P^2$, to give a compound of Formula XXII

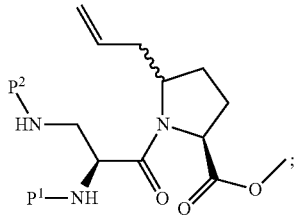

XXII b) converting the alkene of Formula XXII to an aldehyde, to give a compound of Formula XXIII;

$$\text{XXIII}$$

c) removing P² of a compound of Formula XXIII to give a compound of Formula XXIV;

$$\text{XXIV}$$

and d) reducing the C=N double bond of a compound of Formula XXIV, to give a compound of Formula XIX.

DETAILED DESCRIPTION OF THE INVENTION

Figure 1:
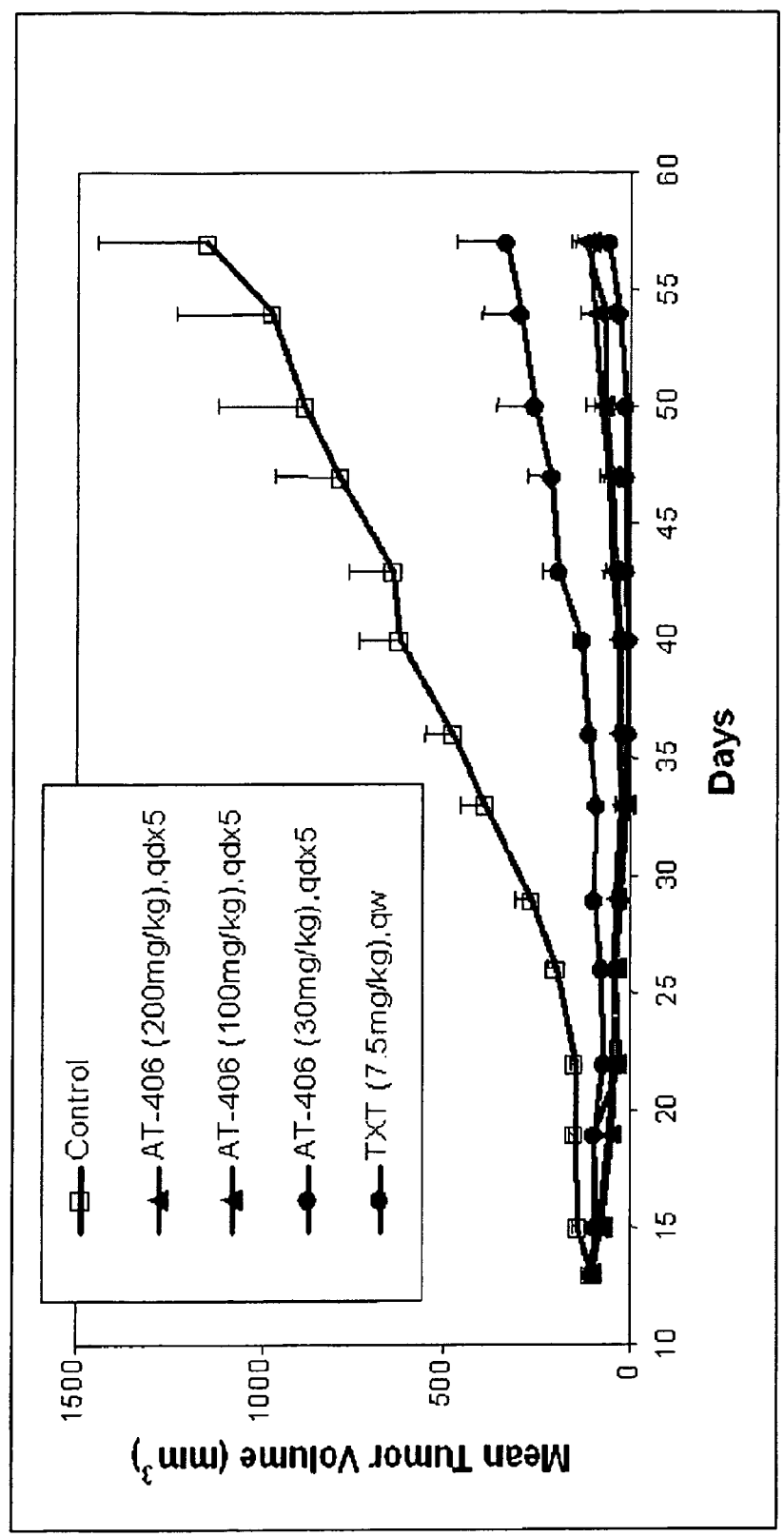
FIG. 1 is a graph illustrating the anti-tumor activity of SM-406 (AT-406) in a breast cancer xenograft model

The present invention relates to conformationally constrained compounds represented by Formulae I-X, which are mimetics of Smac and function as inhibitors of IAPs. These compounds sensitize cells to inducers of apoptosis and, in some instances, themselves induce apoptosis by inhibiting IAPs. Therefore, the invention relates to methods of sensitizing cells to inducers of apoptosis and to methods of inducing apoptosis in cells, comprising contacting the cells with a compound of Formulae I-X alone or in combination with an inducer of apoptosis. The invention further relates to methods of treating, ameliorating, or preventing disorders in an animal that are responsive to induction of apoptosis comprising administering to the animal a compound of Formulae I-X and an inducer of apoptosis. Such disorders include those characterized by a dysregulation of apoptosis and those characterized by overexpression of IAPs. The invention further relates methods of preventing or inhibiting angiogenesis in an animal in need thereof comprising administering to an animal a compound of Formulae I-X.

The term "IAP proteins," as used herein, refers to any known member of the Inhibitor of Apoptosis Protein family, including, but not limited to, XIAP, cIAP-1, cIAP-2, ML-IAP, HIAP, TSIAP, KIAP, NAIP, survivin, livin, ILP-2, apollon, and BRUCE.

The term "overexpression of IAPs," as used herein, refers to an elevated level (e.g., aberrant level) of mRNAs encoding for an IAP protein(s), and/or to elevated levels of IAP protein(s) in cells as compared to similar corresponding non-pathological cells expressing basal levels of mRNAs encoding IAP proteins or having basal levels of IAP proteins. Methods for detecting the levels of mRNAs encoding IAP proteins or levels of IAP proteins in a cell include, but are not limited to, Western blotting using IAP protein antibodies, immunohistochemical methods, and methods of nucleic acid amplification or direct RNA detection. As important as the absolute level of IAP proteins in cells is to determining that they overexpress IAP proteins, so also is the relative level of IAP proteins to other pro-apoptotic signaling molecules (e.g., pro-apoptotic Bcl-2 family proteins) within such cells. When the balance of these two are such that, were it not for the levels of the IAP proteins, the pro-apoptotic signaling molecules would be sufficient to cause the cells to execute the apoptosis program and die, said cells would be dependent on the IAP proteins for their survival. In such cells, exposure to an inhibiting effective amount of an IAP protein inhibitor will be sufficient to cause the cells to execute the apoptosis program and die. Thus, the term "overexpression of an IAP protein" also refers to cells that, due to the relative levels of pro-apoptotic signals and anti-apoptotic signals, undergo apoptosis in response to inhibiting effective amounts of compounds that inhibit the function of IAP proteins.

The terms "anticancer agent" and "anticancer drug," as used herein, refer to any therapeutic agents (e.g., chemotherapeutic compounds and/or molecular therapeutic compounds), radiation therapies, or surgical interventions, used in the treatment of hyperproliferative diseases such as cancer (e.g., in mammals).

The term "prodrug," as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, toxicity, lack of specificity, or limited bioavailability. Exemplary prodrugs comprise an active drug molecule itself and a chemical masking group (e.g., a group that reversibly suppresses the activity of the drug). Some preferred prodrugs are variations or derivatives of compounds that have groups cleavable under metabolic conditions. Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol), amides prepared by reaction of the parent acid compound with an amine, or basic groups reacted to form an acylated base derivative (e.g., a lower alkylamide).

The term "pharmaceutically acceptable salt," as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a compound of Formula I), an animal or a cell within an animal more susceptible, or more responsive, to the biological effects (e.g., promotion or retardation of an aspect of cellular function including, but not limited to, cell division, cell growth, proliferation, invasion, angiogenesis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, including for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "angiogenesis," as used herein means the generation of new blood vessels into a tissue or organ. The term "antiangiogenesis," as used herein, refers to prevention or reduction of the growth of new blood vessels. Examples of diseases or disorders associated with angiogenesis that may be treated with the compounds of the invention include macular degeneration, rheumatoid arthritis, psoriasis, diabetic retinopathy, retinopathy of prematurity, corneal graft rejection, neovascular glaucoma, retrolental fibroplasia, rubeosis, Osler-Webber Syndrome, myocardial angiogenesis, plaque neovascularization, telangiectasia, hemophiliac joints, angiofibroma, wound granulation, intestinal adhesions, atherosclerosis, scleroderma and hypertrophic scars.

The term "hyperproliferative disease," as used herein, refers to any condition in which a localized population of proliferating cells in an animal is not governed by the usual limitations of normal growth. Examples of hyperproliferative disorders include, but are not restricted to cancers (e.g., tumors, neoplasms, lymphomas and the like) or autoimmune disorders. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell. In another embodiment, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "apoptosis-modulating agents," as used herein, refers to agents which are involved in modulating (e.g., inhibiting, decreasing, increasing, promoting) apoptosis. In one embodiment, the apoptosis-modulating agent is an inducer of apoptosis. The term "inducer of apoptosis," as used herein, refers to an agent that induces apoptosis in cells (e.g., cancer cells), rendering those cells more susceptible to executing the apoptosis program. In one embodiment, an agent that induces apoptosis is an anticancer agent. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptotic-modulating agents include, but are not limited to, TNFα, Fas ligand, antibodies to Fas/CD95 and other TNF family receptors, TRAIL (also known as Apo2 Ligand or Apo2L/TRAIL), agonists (e.g., monoclonal or polyclonal agonistic antibodies) of TRAIL-R1 or TRAIL-R2, Bcl-2, p53, BAX, BAD, Akt, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Preferred apoptosis-modulating agents are inducers of apoptosis, such as TNF or a TNF-related ligand, particularly a TRAMP ligand, a Fas/CD95 ligand, a TNFR-1 ligand, or TRAIL The inhibitors of IAPs of the present invention are Smac mimetics having the general Formula I:

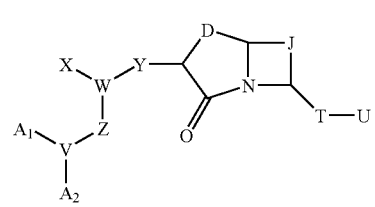

wherein:

$A_1$ and $A_2$ are independently selected from the group consisting of hydrogen and optionally substituted alkyl, wherein $A_2$ is absent when V is O;

V is selected from the group consisting of N, CH and O;
W is selected from the group consisting of CH and N;
X is selected from the group consisting of hydrogen and optionally substituted $C_{1-3}$ alkyl;
Y is selected from the group consisting of CONH, NHCO, C(O)O, OC(O), $(CH_2)_{1-3}$, wherein one or more $CH_2$ groups can be replaced by O, S, or $NR^1$, optionally substituted aryl and optionally substituted heteroaryl;
Z is $(CR^1R^2)_r$;
D is $(CR^1R^2)_n$—$NR^5$—$(CR^3R^4)_m$;
J is selected from the group consisting of optionally substituted alkylenyl and $(CR^1R^2)_p$—$R^6$—$(CR^3R^4)_q$;
T is selected from the group consisting of C=O, C=S, C=NR$^1$, S, S=O, SO$_2$, O, NR$^1$, CR$^1$R$^2$, optionally substituted carbocyclic, optionally substituted heterocyclic, optionally substituted aryl and optionally substituted heteroaryl;
U is selected from the group consisting of H, NR$^1$R$^2$, N(R$^1$)COR$^7$, OR$^1$, SR$^1$, optionally substituted alkyl, optionally substituted aryl and heteroaryl;
n, m, p and q are independently selected from the group consisting of 0-5;
r is 0-3;
each R$^1$, R$^2$, R$^3$ and R$^4$ are independently selected from the group consisting of hydrogen, optionally substituted alkyl, optionally substituted carbocyclic, optionally substituted heterocyclic, optionally substituted aryl and optionally substituted heteroaryl;
R$^5$ is selected from the group consisting of hydrogen, optionally substituted alkyl, optionally substituted heteroalkyl, optionally substituted carbocyclic, optionally substituted heterocyclic, optionally substituted aryl, optionally substituted heteroaryl and COR$^7$;
R$^6$ is selected from the group consisting of O, S, NR$^1$, CR$^1$R$^2$, C=O, C=S and C=NR$^1$; and
R$^7$ is selected from the group consisting of hydrogen, optionally substituted alkyl, optionally substituted carbocyclic, optionally substituted heterocyclic, optionally substituted aryl and optionally substituted heteroaryl;
or a pharmaceutically acceptable salt or prodrug thereof.

In one embodiment, R$^1$ is optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups.

In another particular embodiment, Smac mimetics are compounds of Formula II:

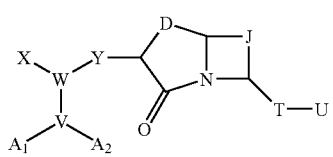

II wherein:
A$_1$ and A$_2$ are independently selected from the group consisting of hydrogen and optionally substituted alkyl, wherein A$_2$ is absent when V is O;
V is selected from the group consisting of N, CH and O;
W is selected from the group consisting of CH and N;
X is optionally substituted C$_{1-3}$ alkyl;
Y is selected from the group consisting of CONH, C(O)O, (CH$_2$)$_{1-3}$ wherein one or more CH$_2$ groups can be replaced by O, S, or NR$^1$, optionally substituted aryl and optionally substituted heteroaryl;
D is $(CR^1R^2)_n$—$NR^5$—$(CR^3R^4)_m$;
J is selected from the group consisting of optionally substituted alkylenyl and $(CR^1R^2)_p$—$R^6$—$(CR^3R^4)_q$;
T is selected from the group consisting of C=O, C=S, C=NR$^1$, S, O, NR$^1$, CR$^1$R$^2$, optionally substituted carbocyclic, optionally substituted heterocyclic, optionally substituted aryl and optionally substituted heteroaryl;
U is selected from the group consisting of H, NR$^1$R$^2$, OR$^1$, SR$^1$, optionally substituted alkyl and optionally substituted aryl;
n, m, p and q are independently selected from 0-5;
each R$^1$, R$^2$, R$^3$ and R$^4$ are independently selected from the group consisting of hydrogen, optionally substituted alkyl, optionally substituted carbocyclic, optionally substituted heterocyclic, optionally substituted aryl and optionally substituted heteroaryl;
R$^5$ is selected from the group consisting of hydrogen, optionally substituted alkyl, optionally substituted heteroalkyl, optionally substituted carbocyclic, optionally substituted heterocyclic, optionally substituted aryl, optionally substituted heteroaryl and COR$^7$;
R$^6$ is selected from the group consisting of O, S, NR$^1$, CR$^1$R$^2$, C=O, C=S and C=NR$^1$; and
R$^7$ is selected from the group consisting of hydrogen, optionally substituted alkyl, optionally substituted carbocyclic, optionally substituted heterocyclic, optionally substituted aryl and optionally substituted heteroaryl;
or a pharmaceutically acceptable salt or prodrug thereof.

In one embodiment, the optional substituents do not include carboxylic acid, cycloalkyl optionally substituted with one or more alkyl, halo, hydroxyl or haloalkyl groups, or aryl optionally substituted with an aryl group, and an optionally substituted heterocyclic group does not include oxopiperizinyl.

In a further embodiment, n and m are independently selected from 0-4 such that n+m is 3 or 4. In a further embodiment, p and q are independently selected from 0 and 1 such that p+q is 1. In a further embodiment, n and m are independently selected from 0-4 such that n+m is 3 or 4 and p and q are independently selected from 0 and 1 such that p+q is 1. In a further embodiment, n and m are independently selected from 0-4 such that n+m is 3 or 4, p and q are independently selected from 0 and 1 such that p+q is 1 and T is C=O. In a further embodiment, n and m are independently selected from 0-4 such that n+m is 3 or 4, p and q are independently selected from 0 and 1 such that p+q is 1 and U is NR$^1$R$^2$. In a further embodiment, n and m are independently selected from 0-4 such that n+m is 3 or 4, p and q are independently selected from 0 and 1 such that p+q is 1 and R$^6$ is CH$_2$. In a further embodiment, n and m are independently selected from 0-4 such that n+m is 3 or 4, p and q are independently selected from 0 and 1 such that p+q is 1, Y is CONH, W is CH and V is N. In another embodiment, R$^1$ is optionally substituted alkyl wherein the optional substituents are selected from the group consisting of aryl optionally substituted with one or more lower alkyl, halo, haloalkyl or heteroaryl groups and heteroaryl optionally substituted with one or more lower alkyl, haloalkyl, and aryl groups.

In another particular embodiment, Smac mimetics are compounds of Formula III:

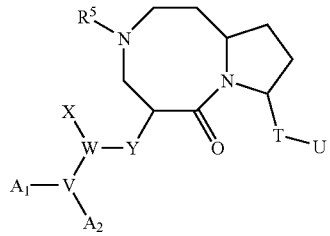

III wherein $A_1, A_2, V, W, X, Y, R^5, T$ and U have the meanings as described above for Formula I; or pharmaceutically acceptable salts or prodrugs thereof.

In one embodiment, $A_1, A_2, V, W, X, Y, R^5, T$ and U have the meanings as described above for Formula II. In another embodiment, W is CH, V is N, T is C=O, U is $NR^1R^2$ and $R^5$ is $COR^7$. In another embodiment, $A_1$ is optionally substituted alkyl and $A_2$ is hydrogen. In another embodiment, $R^1$ is selected from the group consisting of optionally substituted carbocyclic and optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups. In another embodiment, $R^1$ is optionally substituted alkyl wherein the optional substituents are aryl optionally substituted with one or more lower alkyl, halo, haloalkyl or heteroaryl groups, and $R^2$ is hydrogen. In another embodiment, $R^1$ is —CHPh$_2$. In another embodiment, $R^7$ is optionally substituted alkyl. In another embodiment, $R^7$ is —CH$_2$CH(CH$_3$).

In another particular embodiment, Smac mimetics are compounds of Formula IV:

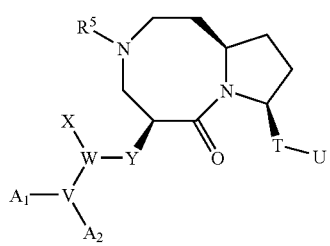

IV wherein $A_1, A_2, V, W, X, Y, R^5, T$ and U have the meanings as described above for Formula I; or a pharmaceutically acceptable salt or prodrug thereof.

In one embodiment, $A_1, A_2, V, W, X, Y, R^5, T$ and U have the meanings as described above for Formula II. In another embodiment, W is CH, V is N, T is C=O, U is $NR^1R^2$ and $R^5$ is $COR^7$. In another embodiment, $A_1$ is optionally substituted alkyl and $A_2$ is hydrogen. In another embodiment, $R^1$ is selected from the group consisting of optionally substituted carbocyclic and optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups. In another embodiment, $R^1$ is optionally substituted alkyl wherein the optional substituents are aryl optionally substituted with one or more lower alkyl, halo, haloalkyl or heteroaryl groups, and $R^2$ is hydrogen. In another embodiment, $R^1$ is —CHPh$_2$. In another embodiment, $R^7$ is optionally substituted alkyl. In another embodiment, $R^7$ is —CH$_2$CH(CH$_3$)$_2$.

In another particular embodiment, Smac mimetics are compounds of Formula V:

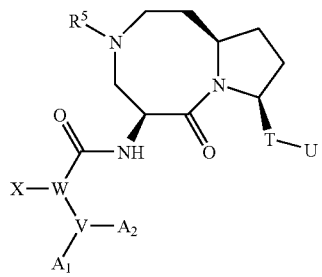

V wherein $A_1, A_2, V, W, X, R^5, T$ and U have the meanings as described above for Formula I; or a pharmaceutically acceptable salt or prodrug thereof.

In one embodiment, $A_1, A_2, V, W, X, Y, R^5, T$ and U have the meanings as described above for Formula II. In another embodiment, W is CH, V is N, T is C=O, U is $NR^1R^2$ and $R^5$ is $COR^7$. In another embodiment, $A_1$ is optionally substituted alkyl and $A_2$ is hydrogen. In another embodiment, $R^1$ is selected from the group consisting of optionally substituted carbocyclic and optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups. In another embodiment, $R^1$ is optionally substituted alkyl wherein the optional substituents are aryl optionally substituted with one or more lower alkyl, halo, haloalkyl or heteroaryl groups, and $R^2$ is hydrogen. In another embodiment, $R^1$ is —CHPh$_2$. In another embodiment, $R^7$ is optionally substituted alkyl. In another embodiment, $R^7$ is —CH$_2$CH(CH$_3$)$_2$.

In another particular embodiment, Smac mimetics are compounds of Formula VI:

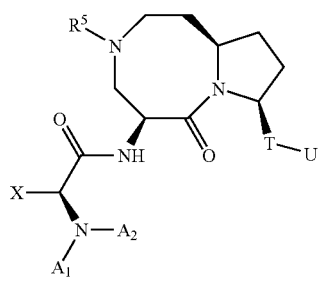

VI wherein $A_1, A_2, R^5, T$ and U have the meanings as described above for Formula I, and X is optionally substituted alkyl; or a pharmaceutically acceptable salt or prodrug thereof.

In one embodiment, $A_1, A_2, X, R^5, T$ and U have the meanings as described above for Formula II. In another embodiment, T is C=O, U is $NR^1R^2$ and $R^5$ is $COR^7$. In another embodiment, $A_1$ is optionally substituted alkyl and $A_2$ is hydrogen. In another embodiment, $R^1$ is selected from the group consisting of optionally substituted carbocyclic and optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups. In another embodiment, $R^1$ is optionally substituted alkyl wherein the optional substituents are aryl optionally substituted with one or more lower alkyl, halo, haloalkyl or heteroaryl groups, and $R^2$ is hydrogen. In another embodiment, $R^1$ is —$CHPh_2$. In another embodiment, $R^7$ is optionally substituted alkyl. In another embodiment, $R^7$ is —$CH_2CH(CH_3)_2$.

In another particular embodiment, Smac mimetics are compounds of Formula VII:

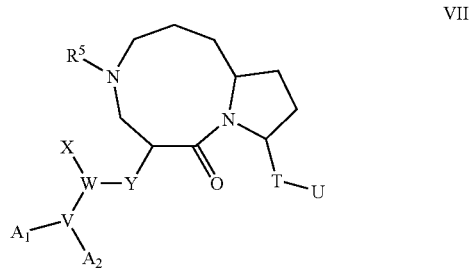

VII wherein $A_1$, $A_2$, V, W, X, Y, $R^5$, T and U have the same meanings as described above for Formula I; or a pharmaceutically acceptable salt or prodrug thereof.

In one embodiment, W is CH, V is N, T is C=O, U is $NR^1R^2$ and $R^5$ is $COR^7$. In another embodiment, Y is CONH. In another embodiment, $A_1$ is optionally substituted alkyl and $A_2$ is hydrogen. In another embodiment, $R^1$ is selected from the group consisting of optionally substituted carbocyclic and optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups. In another embodiment, $R^1$ is optionally substituted alkyl wherein the optional substituents are aryl optionally substituted with one or more lower alkyl, halo, haloalkyl or heteroaryl groups, and $R^2$ is hydrogen. In another embodiment, $R^1$ is —$CHPh_2$. In another embodiment, $R^7$ is optionally substituted alkyl. In another embodiment, $R^7$ is —$CH_2CH(CH_3)_2$.

In another particular embodiment, Smac mimetics are compounds of Formula VIII:

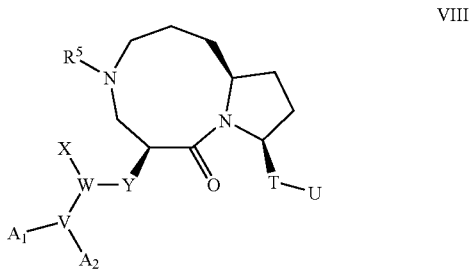

VIII wherein $A_1$, $A_2$, V, W, X, Y, $R^5$, T and U have the same meanings as described above for Formula I; or a pharmaceutically acceptable salt or prodrug thereof.

In one embodiment, W is CH, V is N, T is C=O, U is $NR'R^2$ and $R^5$ is $COR^7$. In another embodiment, Y is CONH. In another embodiment, $A_1$ is optionally substituted alkyl and $A_2$ is hydrogen. In another embodiment, $R^1$ is selected from the group consisting of optionally substituted carbocyclic and optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups. In another embodiment, $R^1$ is optionally substituted alkyl wherein the optional substituents are aryl optionally substituted with one or more lower alkyl, halo, haloalkyl or heteroaryl groups, and $R^2$ is hydrogen. In another embodiment, $R^1$ is —$CHPh_2$. In another embodiment, $R^7$ is optionally substituted alkyl. In another embodiment, $R^7$ is —$CH_2CH(CH_3)_2$.

In another particular embodiment, Smac mimetics are compounds of Formula IX:

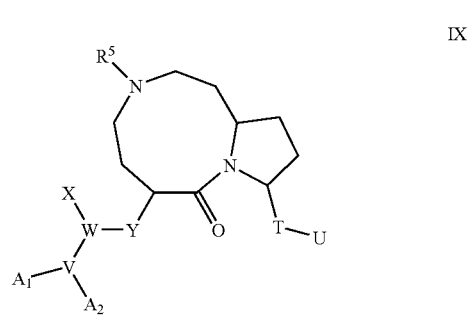

IX wherein $A_1$, $A_2$, V, W, X, Y, $R^5$, T and U have the same meanings as described above for Formula I; or a pharmaceutically acceptable salt or prodrug thereof.

In one embodiment, W is CH, V is N, T is C=O, U is $NR^1R^2$ and $R^5$ is $COR^7$. In another embodiment, Y is CONH. In another embodiment, $A_1$ is optionally substituted alkyl and $A_2$ is hydrogen. In another embodiment, $R^1$ is selected from the group consisting of optionally substituted carbocyclic and optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups. In a another embodiment, $R^1$ is optionally substituted alkyl wherein the optional substituents are aryl optionally substituted with one or more lower alkyl, halo, haloalkyl or heteroaryl groups, and $R^2$ is hydrogen. In another embodiment, $R^1$ is —$CHPh_2$. In another embodiment, $R^7$ is optionally substituted alkyl. In another embodiment, $R^7$ is —$CH_2CH(CH_3)_2$.

In another particular embodiment, Smac mimetics are compounds of Formula X:

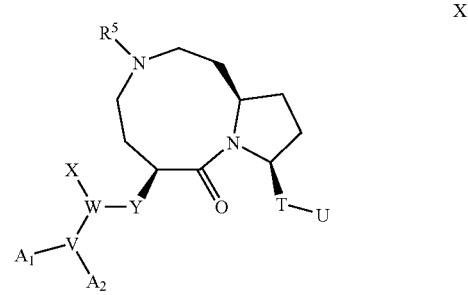

X wherein $A_1$, $A_2$, V, W, X, Y, $R^5$, T and U have the same meanings as described above for Formula I; or a pharmaceutically acceptable salt or prodrug thereof.

In one embodiment, W is CH, V is N, T is C=O, U is $NR^1R^2$ and $R^5$ is $COR^7$. In another embodiment, Y is CONH.

In another embodiment, $A_1$ is optionally substituted alkyl and $A_2$ is hydrogen. In another embodiment, $R^1$ is selected from the group consisting of optionally substituted carbocyclic and optionally substituted alkyl wherein the optional substituents are selected from the group consisting of aryl optionally substituted with one or more lower alkyl, halo, haloalkyl or heteroaryl groups, and heteroaryl optionally substituted with one or more lower alkyl, haloalkyl, and aryl groups. In another embodiment, $R^1$ is optionally substituted alkyl wherein the optional substituents are aryl optionally substituted with one or more lower alkyl, halo, haloalkyl or heteroaryl groups, and $R^2$ is hydrogen. In another embodiment, $R^1$ is —$CHPh_2$. In another embodiment, $R^7$ is optionally substituted alkyl. In another embodiment, $R^7$ is —$CH_2CH(CH_3)_2$.

Useful alkyl groups include straight-chained or branched $C_{1-18}$ alkyl groups, especially methyl, ethyl, propyl, isopropyl, t-butyl, sec-butyl, 3-pentyl and 3-hexyl groups. In one embodiment, the alkyl is a $C_{1-6}$ alkyl group.

The term "alkylenyl" refers to a divalent alkyl radical containing 1, 2, 3 or 4 joined methylene groups as exemplified by —$(CH_2)_4$—.

Useful alkenyl groups include straight-chained or branched $C_{2-18}$ alkyl groups, especially ethenyl, propenyl, isopropenyl, butenyl, isobutenyl, and hexenyl.

Useful alkynyl groups are $C_{2-18}$ alkynyl groups, especially ethynyl, propynyl, butynyl, and 2-butynyl groups.

Useful cycloalkyl groups include $C_{3-10}$ cycloalkyl groups. Typical cycloalkyl groups include cyclopropyl, cyclobutyl, cyclopentyl, cyclohexyl, cycloheptyl, adamantyl and norbornyl.

Useful aryl groups include $C_{6-14}$ aryl, especially phenyl (abbreviated as "Ph"), naphthyl, phenanthrenyl, anthracenyl, indenyl, azulenyl, biphenyl, biphenylenyl, and fluorenyl groups.

Useful heteroaryl groups include $C_{5-14}$ heteroaryl groups, especially thienyl, benzo[1]thienyl, naphtho [2,3-b]thienyl, thianthrenyl, furyl, pyranyl, isobenzofuranyl, chromenyl, xanthenyl, phenoxanthenyl, 2H-pyrrolyl, pyrrolyl, imidazolyl, triazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

Optional substituents include one or more alkyl; halo; hydroxyl; carboxylic acid (i.e., —$CO_2H$ and salts thereof); haloalkyl; cycloalkyl optionally substituted with one or more alkyl, halo, hydroxyl or haloalkyl groups; aryl optionally substituted with one or more lower alkyl, halo, haloalkyl, aryl or heteroaryl groups; aryloxy optionally substituted with one or more lower alkyl, haloalkyl, or heteroaryl groups; aralkyl; heteroaryl optionally substituted with one or more lower alkyl, haloalkyl, and aryl groups; heteroaryloxy optionally substituted with one or more lower alkyl, haloalkyl, and aryl groups; alkoxy; alkylthio; arylthio; amido; amino; acyloxy; arylacyloxy optionally substituted with one or more lower alkyl, haloalkyl, and aryl groups; diphenylphosphinyloxy optionally substituted with one or more lower alkyl, halo or haloalkyl groups; heterocyclo optionally substituted with one or more lower alkyl, haloalkyl, and aryl groups; heterocycloalkoxy optionally substituted with one or more lower alkyl, haloalkyl, and aryl groups; partially unsaturated heterocycloalkyl optionally substituted with one or more lower alkyl, haloalkyl, and aryl groups; or partially unsaturated heterocycloalkyloxy optionally substituted with one or more lower alkyl, haloalkyl, and aryl groups.

Useful saturated or partially saturated carbocyclic groups are cycloalkyl groups as defined above, as well as cycloalkenyl groups, such as cyclopentenyl, cycloheptenyl and cyclooctenyl. Carbocyclic groups also include groups having fused optionally substituted aryl groups such as tetralin.

Useful halo or halogen groups include fluorine, chlorine, bromine and iodine.

Useful aralkyl and heteroaralkyl groups include any of the above-mentioned $C_{1-18}$ alkyl groups substituted by one or more of the above-mentioned optionally substituted $C_{6-14}$ aryl groups or heteroaryl groups. In one embodiment, the aralkyl is substituted with two optionally substituted $C_{6-14}$ aryl groups. In another embodiment, the aralkyl is substituted with one optionally substituted $C_{6-14}$ aryl group. In one embodiment, the optionally substituted $C_{6-14}$ aryl group is an optionally substituted phenyl group. Useful aralkyl groups include benzyl (abbreviated as Bn), phenethyl and naphthylmethyl.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful alkoxy groups include oxygen substituted by one of the $C_{1-18}$ alkyl groups mentioned above.

Useful alkylthio groups include sulfur substituted by one of the $C_{1-18}$ alkyl groups mentioned above. Also included are the sulfoxides and sulfones of such alkylthio groups.

Useful amido groups include carbonylamido as well as any $C_{1-6}$ acyl (alkanoyl) attached to an amino nitrogen, e.g., acetamido, propionamido, butanoylamido, pentanoylamido, hexanoylamido as well as aryl-substituted $C_{2-6}$ substituted acyl groups.

Useful acyloxy groups are any $C_{1-6}$ acyl (alkanoyl) attached to an oxy (—O—) group, e.g., formyloxy, acetoxy, propionoyloxy, butanoyloxy, pentanoyloxy, hexanoyloxy and the like.

Useful arylacyloxy groups include any of the aryl groups mentioned above substituted on any of the acyloxy groups mentioned above, e.g., 2,6-dichlorobenzoyloxy, 2,6-difluorobenzoyloxy and 2,6-di-(trifluoromethyl)-benzoyloxy groups.

Useful amino groups include —$NH_2$, —$NHR_{11}$, and —$NR_{11}R_{12}$, wherein $R_{11}$ and $R_{12}$ are $C_{1-18}$ alkyl or cycloalkyl groups as defined above.

Useful saturated or partially saturated heterocyclic groups include tetrahydrofuranyl, pyranyl, piperidinyl, piperizinyl, oxopiperizinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

Useful arylene groups include $C_{6-14}$ arylene, especially phenylene, naphthylene, phenanthrenylene, anthracenylene, indenylene, azulenylene, biphenylene, biphenylenylene, and fluorenylene groups.

Useful heteroarylene groups include disubstituted heteroaryl groups such as 2,5-thienylene, 2,4-imidazoylene, and 1,3-triazolylene.

The term "leaving group" as used herein refers to an atom or group that becomes detached from an atom or group in what is considered to be the residual or main part of the substrate in a specified reaction. In amide coupling reactions, exemplary leaving groups include —F, —Cl, —Br, —OH, —OC$_6$F$_5$, —O(CO)alkyl and the like. In one embodiment, the leaving group is —Cl. In another embodiment, the leaving group is an activated form of —OH (e.g., OBt, O-acylisourea). An activating agent (e.g., dicyclohexylcarbodiimide (DCC), 1-ethyl-3-(3-dimethylaminopropyl)carbodiimide (EDC), benzotriazol-1-yloxy)tripyrrolidinophosphonium hexafluorophosphate (PyBop)) may be employed to active a carboxylic acid (i.e., the leaving group is —OH) toward amide formation. Such activating agents are well known to those of skill in the art of organic synthesis. Other additives, such as N-hydroxybenzotriazole (HOBt) or N-hydroxysuccinimide (HOSu), may also be added to optimize reaction parameters (e.g., rate, yield, purity, racemization).

The term "isolated" as used herein when referring to the product of a chemical reaction means that the desired product or products are separated from undesired components of the reaction mixture (e.g., solvents, starting materials, chemical reagents) prior to a subsequent chemical transformation. The desired product(s) of a chemical reaction may be separated from undesired components by a variety of methods, e.g., filtration through celite or silica gel followed by removal of volatile (e.g., solvent) components.

The term "amine protecting group" as used herein refers to group that blocks (i.e., protects) the amine functionality while reactions are carried out on other functional groups or parts of the molecule. Those skilled in the art will be familiar with the selection, attachment, and cleavage of amine protecting groups and will appreciate that many different protective groups are known in the art, the suitability of one protective group or another being dependent on the particular the synthetic scheme planned. Treatises on the subject are available for consultation, such as Greene and Wuts, "Protective Groups in Organic Synthesis," 3rd Ed., pp. 17-245 (J. Wiley & Sons, 1999), the disclosure of which is incorporated by reference. Suitable amine protecting groups include the carbobenzyloxy (Cbz), tert-butyloxycarbonyl (BOC), 9-fluorenylmethyloxycarbonyl (FMOC) and benzyl (Bn) group.

The term "about," as used herein, includes the recited number±10%. Thus, "about 10" means 9 to 11.

Throughout the specification, groups an optional substituents thereof are chosen to provide stable moieties and compounds.

Certain of the compounds of the present invention may exist as stereoisomers including optical isomers. The invention includes all stereoisomers, both as pure individual stereoisomer preparations and enriched preparations of each, and both the racemic mixtures of such stereoisomers as well as the individual enantiomers that may be separated according to methods that are well known to those of skill in the art.

In certain embodiments of the invention the compound of Formula I is selected from the group consisting of:

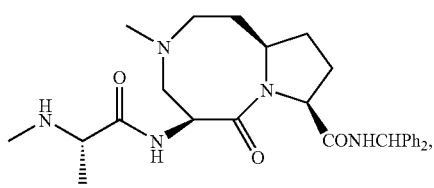

-continued

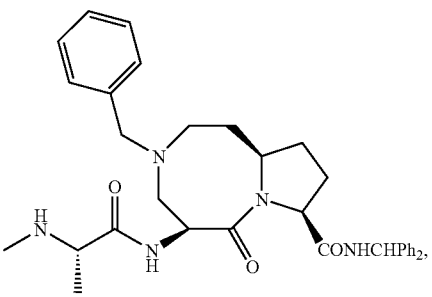

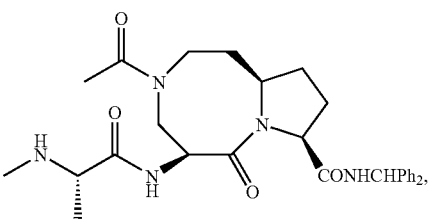

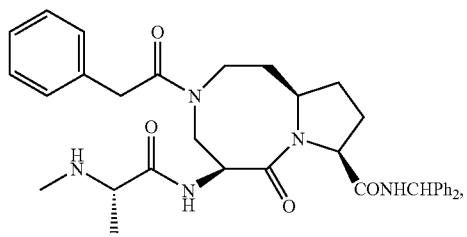

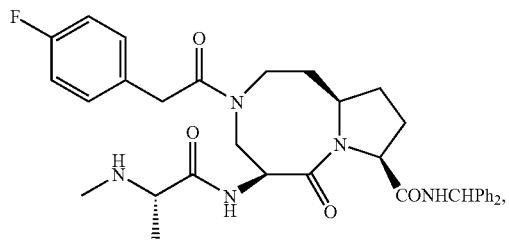

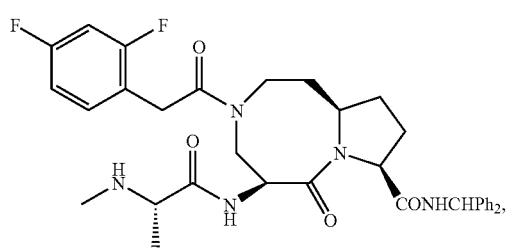

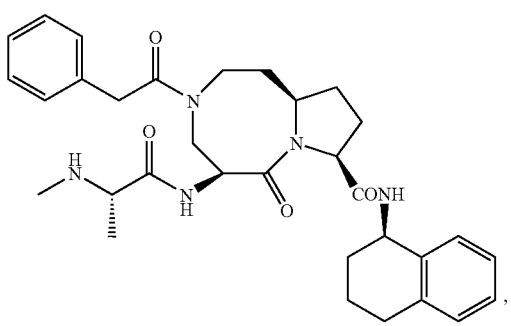

31
-continued
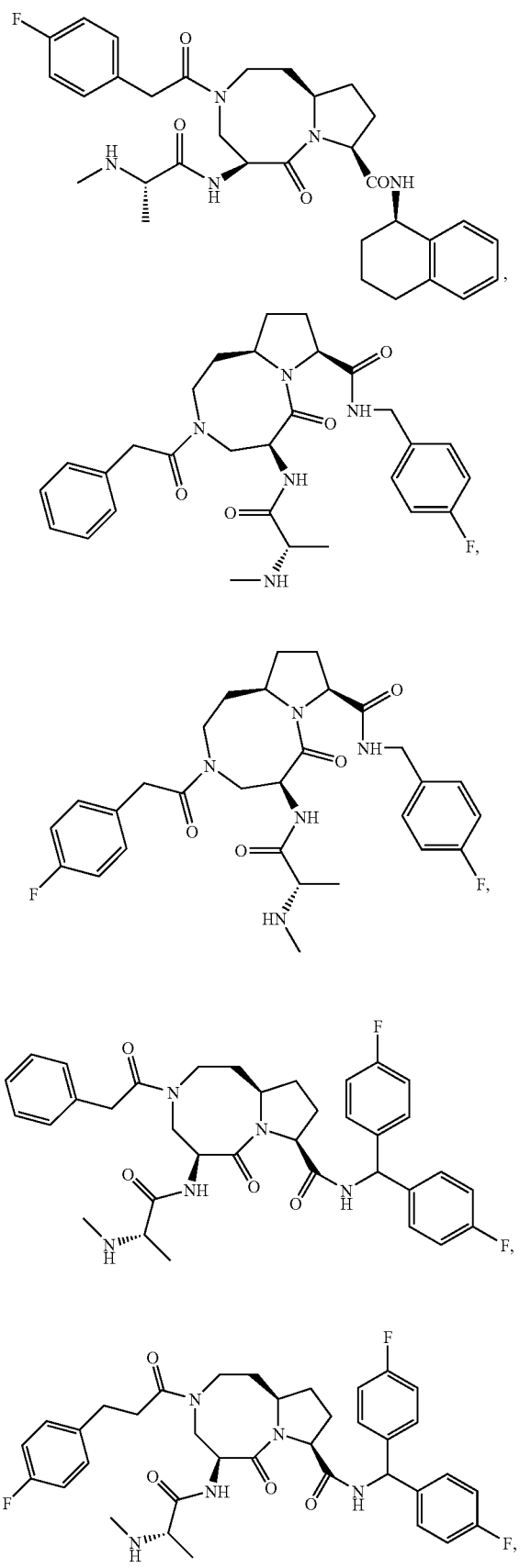
32
-continued
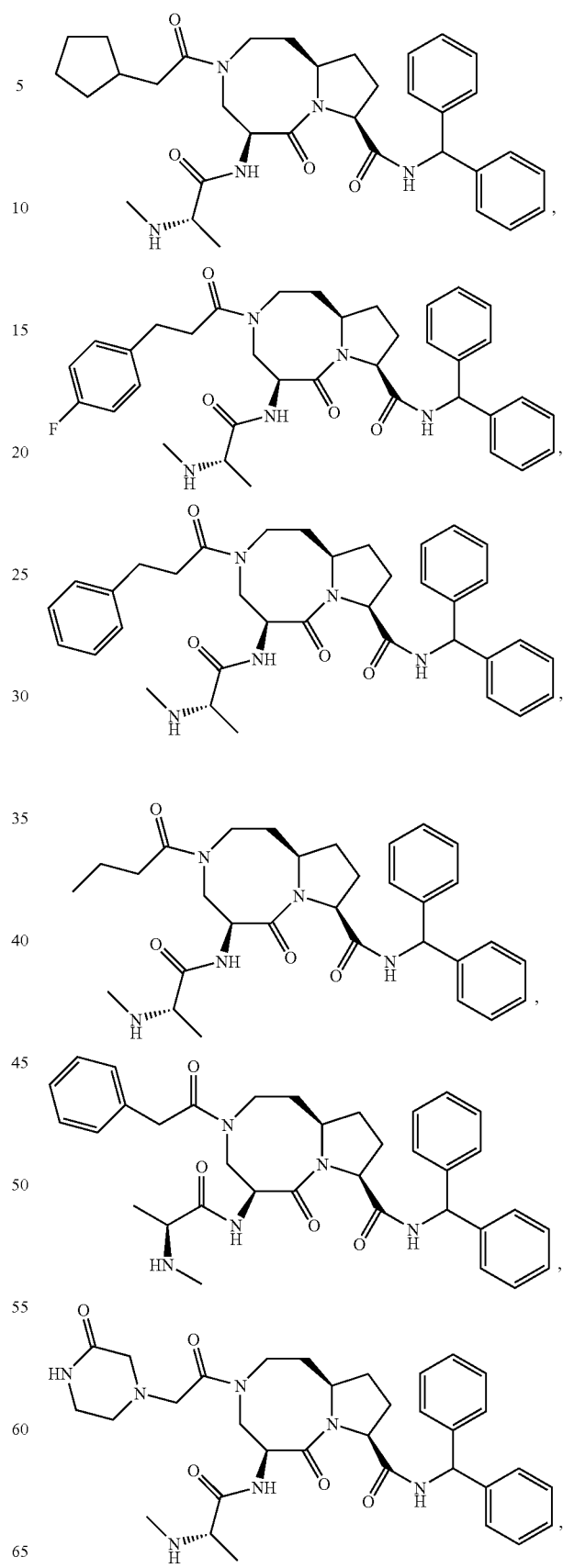

33
-continued
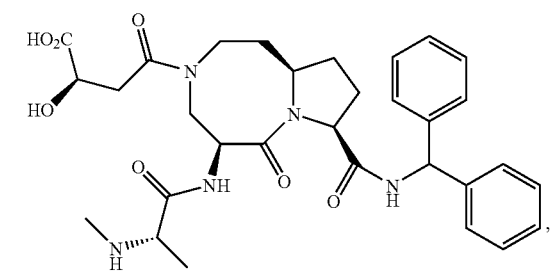
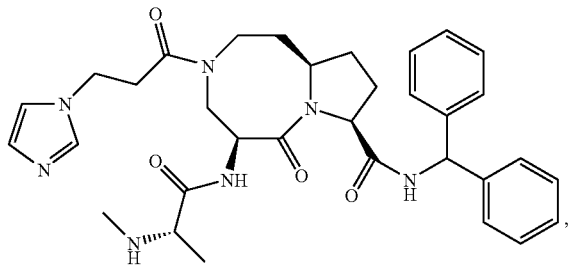
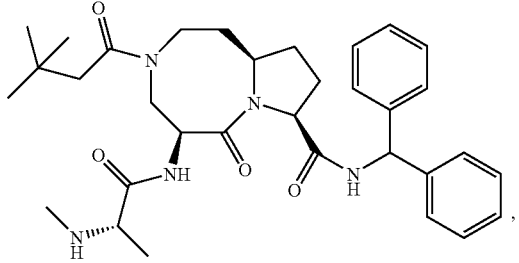
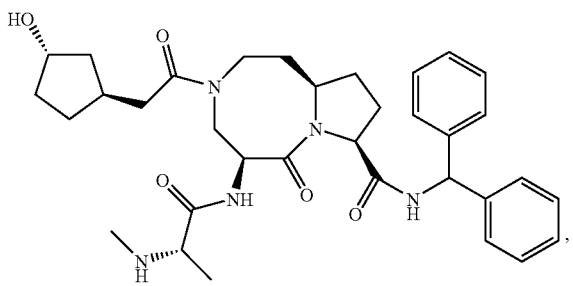
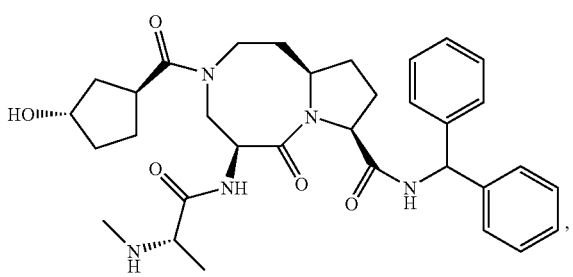
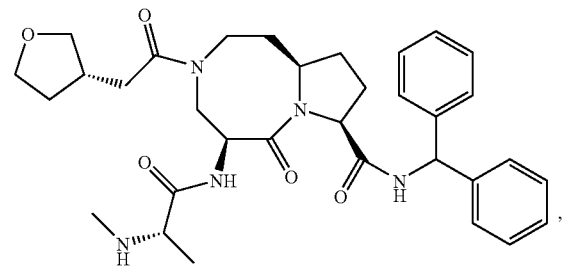
34
-continued
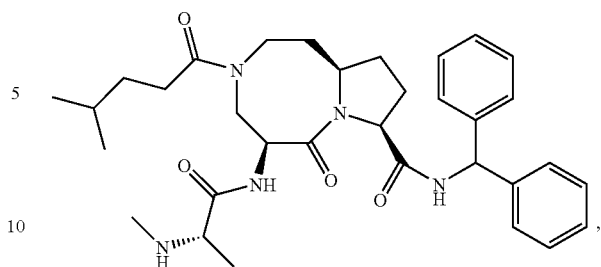
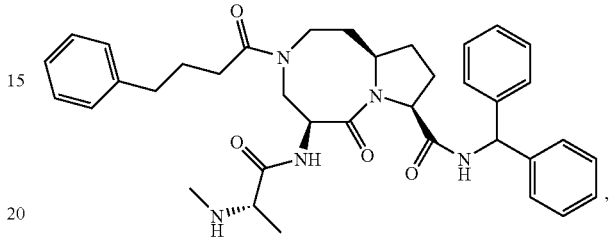
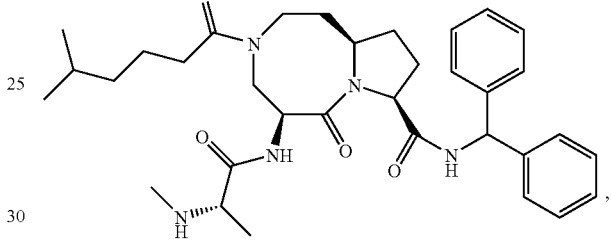
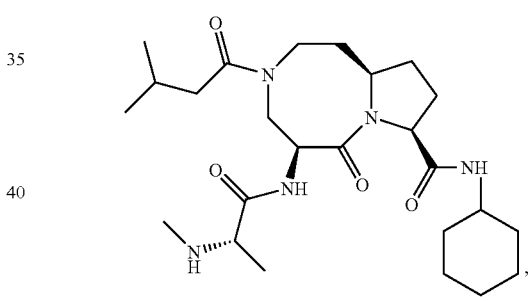
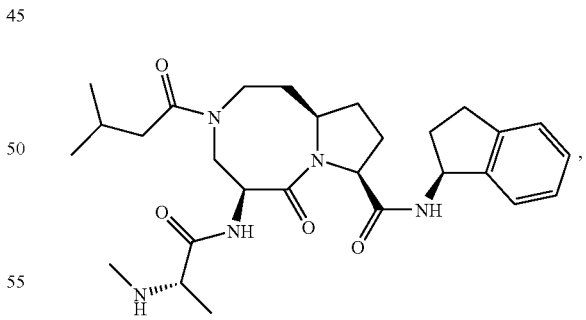
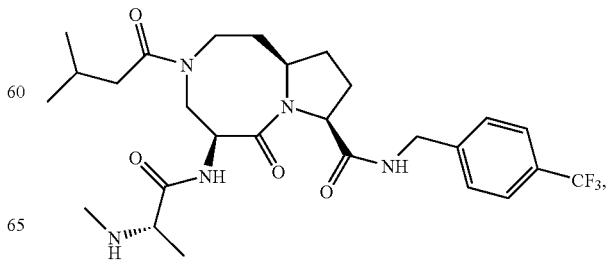

35
-continued
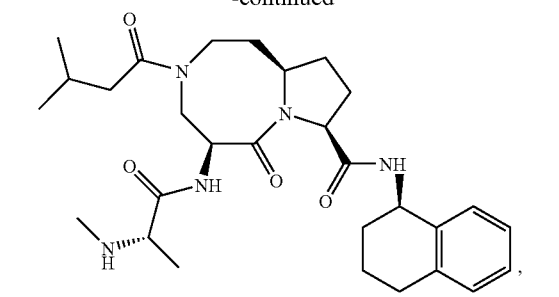
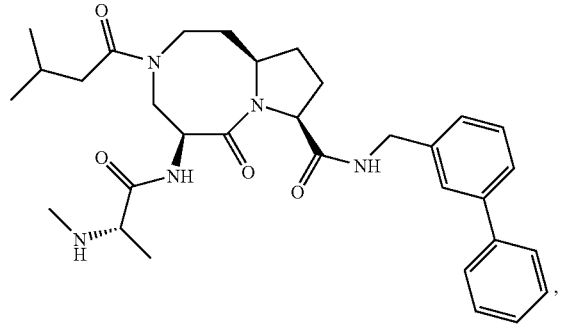
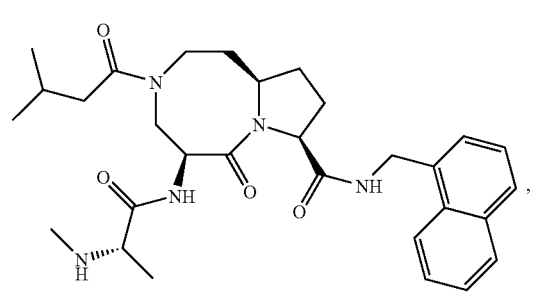
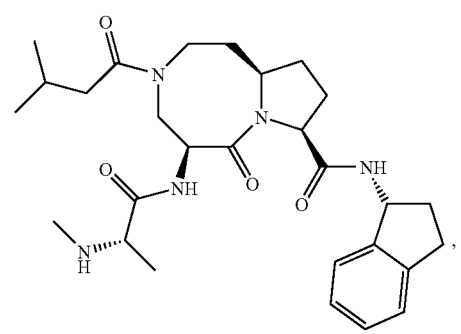
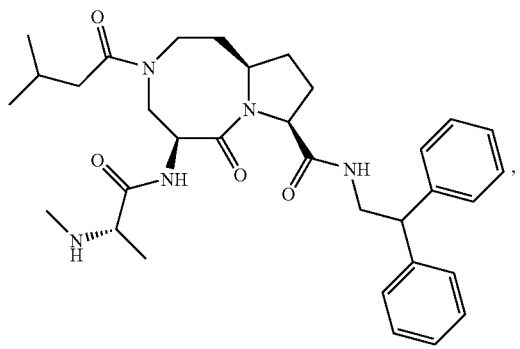
36
-continued
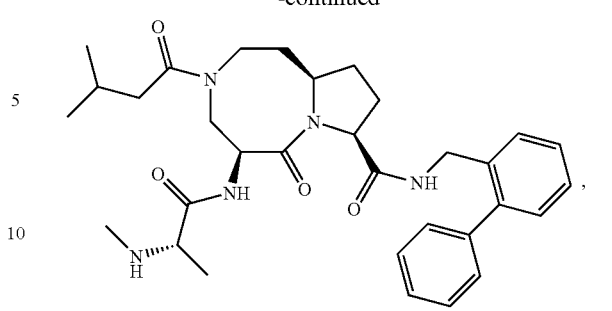
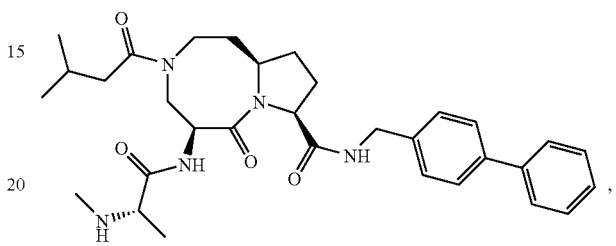
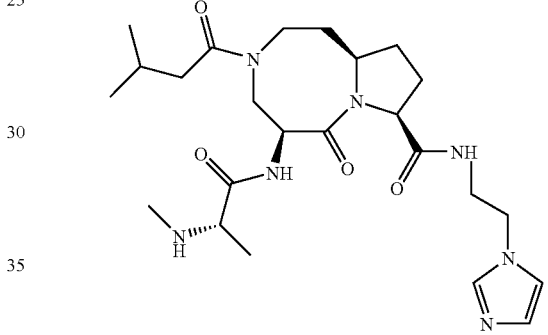
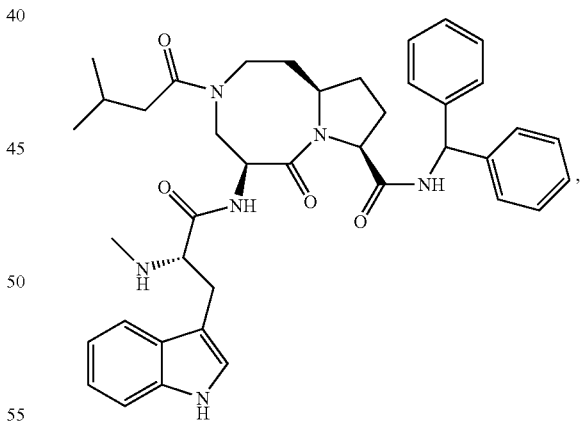
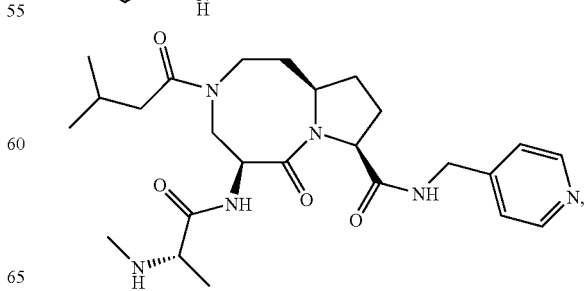

-continued
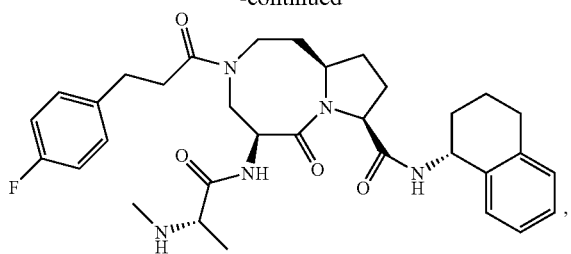
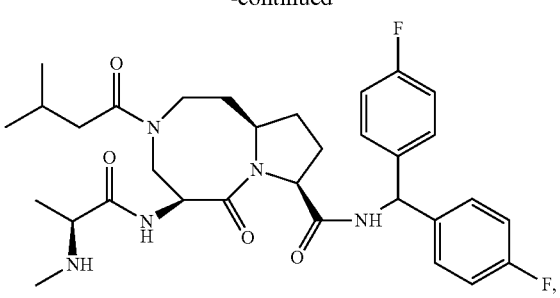
or a pharmaceutically acceptable salt or prodrug thereof.
In another embodiment of the invention the compound of Formula II is selected from the group consisting of:
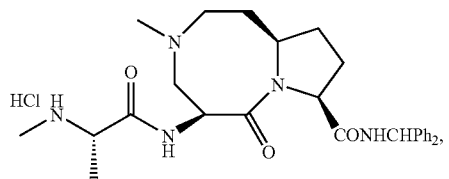
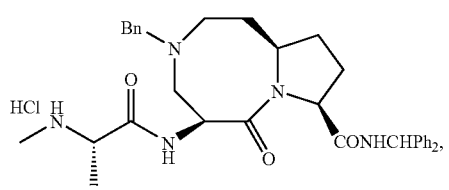
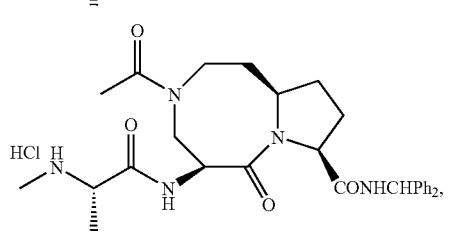

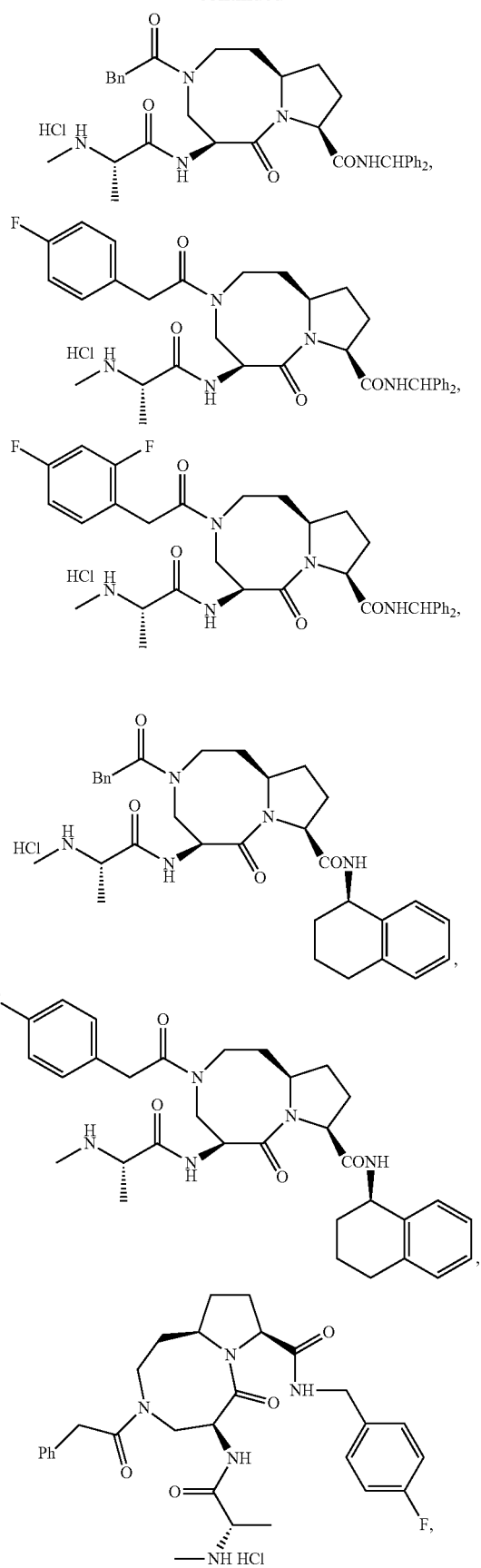
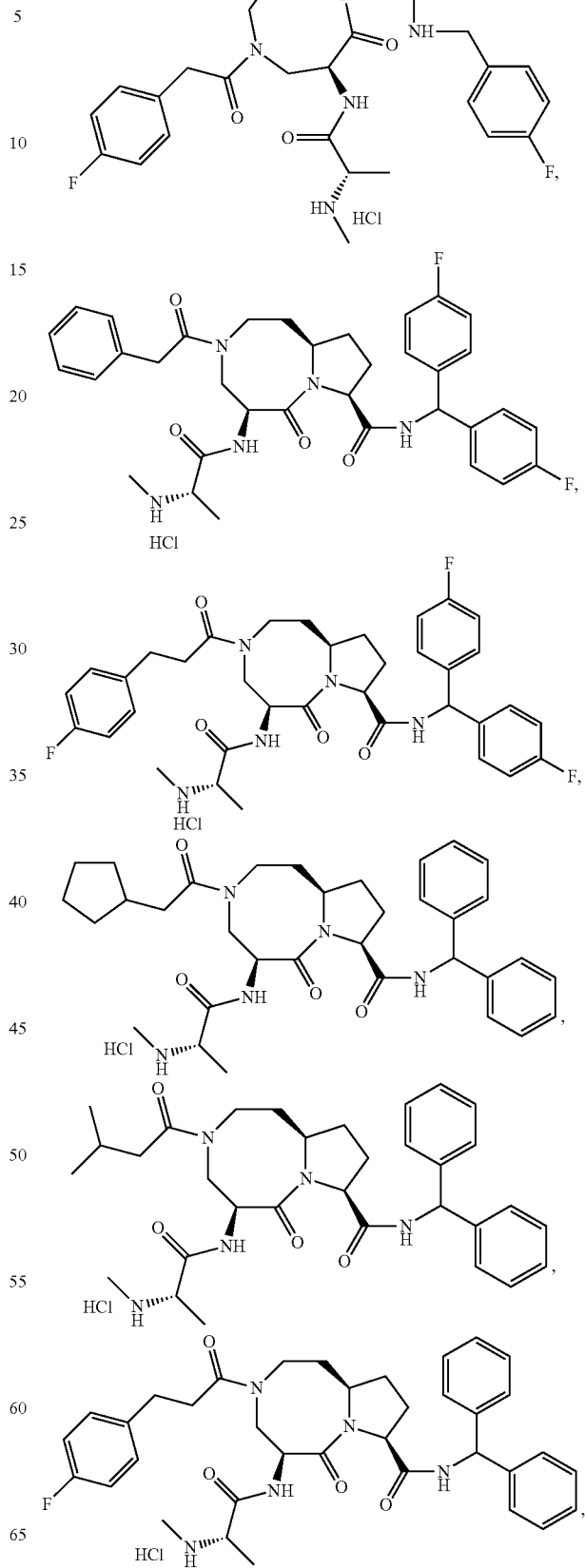

-continued

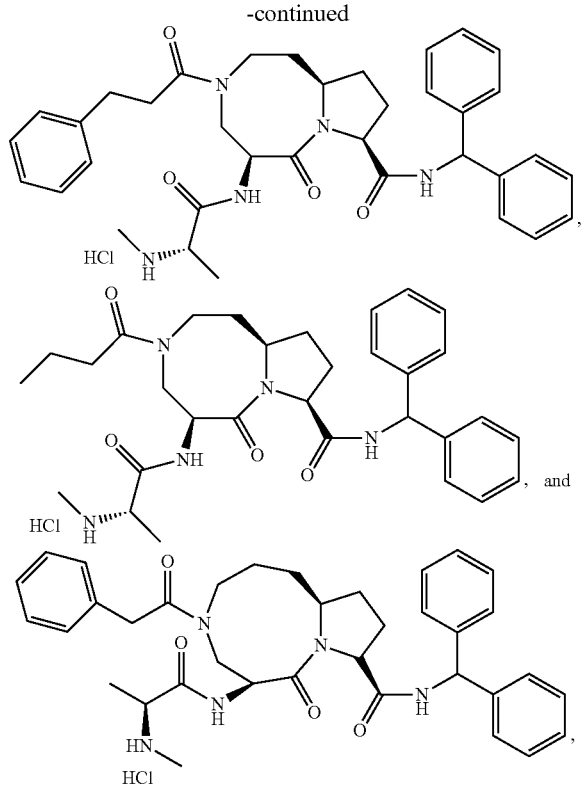

or the free base thereof, or another pharmaceutically acceptable salt thereof, or a prodrug thereof.

In another embodiment of the invention, the compound of Formula I is:

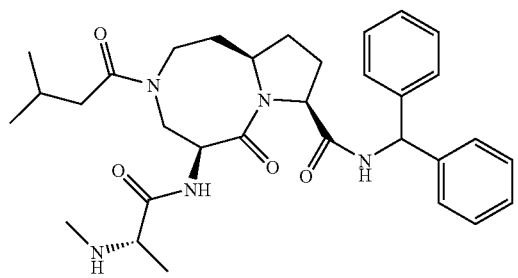

or a pharmaceutically acceptable salt or prodrug thereof.

The present invention also pertains to a process for the preparation of a compound of Formula XI

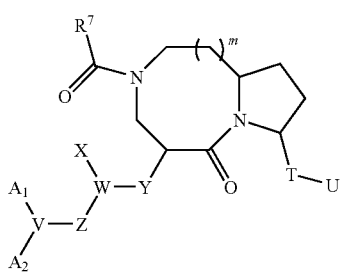

comprising condensing a compound of Formula XII

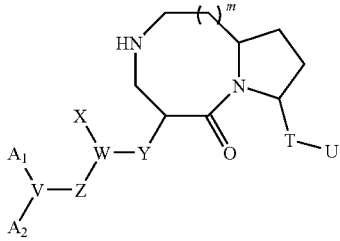

with $R^7CO$-L, wherein $A_1$, $A_2$, V, W, X, Y, Z, T, U and $R^7$ have the meanings as described above for Formula I, m is 1 or 2, and L is a leaving group. In one embodiment, L is Cl or OBt. In one embodiment, Z is $(CR^1R^2)_r$ and r is 0. In another embodiment, m is 1.

In one embodiment, the condensation reaction is conducted in an inert organic solvent such as acetonitrile, benzene, chloroform, 1,2-dichloroethane, 1,2-dimethoxyethane, dimethylformamide, dimethylsulfoxide, dioxane, dichloromethane, N-methyl-2-pyrrolidinone or tetrahydrofuran. In another embodiment, the condensation reaction is carried out in tetrahydrofuran. In another embodiment, the condensation reaction is carried out in dichloromethane. In one embodiment, the condensation reaction is carried out at about −20° C. to about 25° C. In another embodiment, the condensation reaction is carried out at about 20° C. In one embodiment, the condensation reaction is complete in about 1 hour to about 48 hours. In another embodiment, the condensation reaction is complete in about 12 hours.

In one embodiment, L is —OH. In another embodiment, the condensation reaction is carried out in the presence of an activating agent. In another embodiment, the activating agent is dicyclohexylcarbodiimide, 1-ethyl-3-(3-dimethylaminopropyl)carbodiimide or benzotriazol-1-yloxy)tripyrrolidinophosphonium hexafluorophosphate. In another embodiment, the activating agent is 1-ethyl-3-(3-dimethylaminopropyl) carbodiimide. In another embodiment, the condensation reaction is carried out in the presence of an activating agent and an additive that optimize reaction parameters such as purity and yield. In another embodiment, the additive is N-hydroxybenzotriazole.

The progress of the condensation reaction between a compound of Formula XII and $R^7CO$-L can be monitored by analytical methods known in the art such as TLC, LC, LC/MS, HPLC, NMR, etc. A compound of Formula XI can be isolated and purified by any means known in the art such normal- and reverse-phase column chromatography (e.g., column chromatography on silica gel or reverse-phase HPLC), crystallization, extraction, etc. The product thus isolated can be subjected to further purification (e.g., recrystallization) until the desired level of purity is achieved. In one embodiment, a compound of Formula XI has a purity of 90%, 91%, 92%, 93%, 94%, 95%, 96%, 97%, 98%, 99% or more.

In another embodiment, the invention pertains to a process for the preparation of a compound of Formula XIII

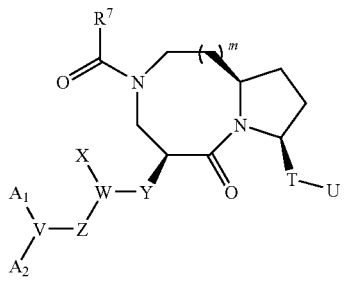

XIII comprising condensing a compound of Formula XIV

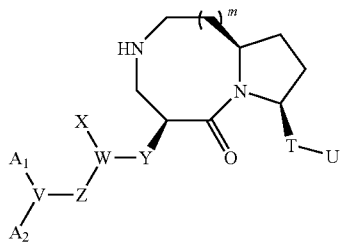

XIV with R⁷CO-L, wherein $A_1$, $A_2$, V, W, X, Y, Z, T and U have the meanings as described above for Formula I, m is 1 or 2, and L is a leaving group. In one embodiment, L is Cl or OBt. In one embodiment, Z is $(CR^1R^2)_r$ and r is 0. In another embodiment, m is 1.

In one embodiment, the condensation reaction is conducted in an inert organic solvent such as acetonitrile, benzene, chloroform, 1,2-dichloroethane, 1,2-dimethoxyethane, dimethylformamide, dimethylsulfoxide, dioxane, dichloromethane, N-methyl-2-pyrrolidinone or tetrahydrofuran. In another embodiment, the condensation reaction is carried out in tetrahydrofuran. In another embodiment, the condensation reaction is carried out in dichloromethane. In one embodiment, the condensation reaction is carried out at about –20° C. to about 25° C. In another embodiment, the condensation reaction is carried out at about 20° C. In one embodiment, the condensation reaction is complete in about 1 hour to about 48 hours. In another embodiment, the condensation reaction is complete in about 12 hours.

In one embodiment, L is —OH or —OBt. In another embodiment, the condensation reaction is carried out in the presence of an activating agent. In another embodiment, the activating agent is dicyclohexylcarbodiimide, 1-ethyl-3-(3-dimethylaminopropyl)carbodiimide or benzotriazol-1-yloxy)tripyrrolidinophosphonium hexafluorophosphate. In another embodiment, the activating agent is 1-ethyl-3-(3-dimethylaminopropyl)carbodiimide. In another embodiment, the condensation reaction is carried out in the presence of an activating agent and an additive that optimize reaction parameters such as purity and yield. In another embodiment, the additive is N-hydroxybenzotriazole.

The progress of the condensation reaction between a compound of Formula XIV and R⁷CO-L can be monitored by analytical methods known in the art such as TLC, LC, LC/MS, HPLC, NMR, etc. A compound of Formula XIII can be isolated and purified by any means known in the art such normal- and reverse-phase column chromatography (e.g., column chromatography on silica gel or reverse-phase HPLC), crystallization, extraction, etc. The product thus isolated can be subjected to further purification (e.g., recrystallization) until the desired level of purity is achieved. In one embodiment, a compound of Formula XIII has a purity of 90%, 91%, 92%, 93%, 94%, 95%, 96%, 97%, 98%, 99% or more.

In another embodiment, the invention pertains to a process for the preparation of a compound of Formula XV

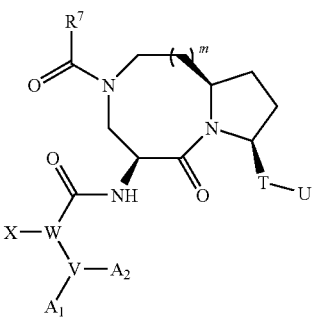

XV comprising condensing a compound of Formula XVI

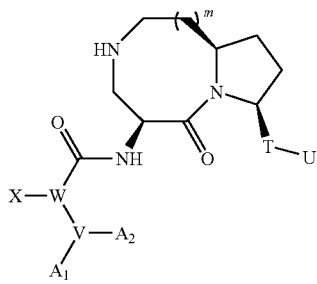

XVI with R⁷CO-L, wherein $A_1$, $A_2$, V, W, X, T, U and R⁷ have the meanings as described above for Formula I, m is 1 or 2, and L is a leaving group. In one embodiment, L is Cl, OH or OBt. In one embodiment, m is 1.

In one embodiment, the condensation reaction is conducted in an inert organic solvent such as acetonitrile, benzene, chloroform, 1,2-dichloroethane, 1,2-dimethoxyethane, dimethylformamide, dimethylsulfoxide, dioxane, dichloromethane, N-methyl-2-pyrrolidinone or tetrahydrofuran. In another embodiment, the condensation reaction is carried out in tetrahydrofuran. In another embodiment, the condensation reaction is carried out in dichloromethane. In one embodiment, the condensation reaction is carried out at about –20° C. to about 25° C. In another embodiment, the condensation reaction is carried out at about 20° C. In one embodiment, the condensation reaction is complete in about 1 hour to about 48 hours In another embodiment, the condensation reaction is complete in about 12 hours.

In one embodiment, L is —OH or —OBt. In another embodiment, the condensation reaction is carried out in the presence of an activating agent. In another embodiment, the activating agent is dicyclohexylcarbodiimide, 1-ethyl-3-(3-dimethylaminopropyl)carbodiimide or benzotriazol-1-yloxy)tripyrrolidinophosphonium hexafluorophosphate. In another embodiment, the activating agent is 1-ethyl-3-(3- dimethylaminopropyl)carbodiimide. In another embodiment, the condensation reaction is carried out in the presence of an activating agent and an additive that optimize reaction parameters such as purity and yield. In another embodiment, the additive is N-hydroxybenzotriazole.

The progress of the condensation reaction between a compound of Formula XIV and R$^7$CO-L can be monitored by analytical methods known in the art such as TLC, LC, LC/MS, HPLC, NMR, etc. A compound of Formula XV can be isolated and purified by any means known in the art such normal- and reverse-phase column chromatography (e.g., column chromatography on silica gel or reverse-phase HPLC), crystallization, extraction, etc. The product thus isolated can be subjected to further purification (e.g., recrystallization) until the desired level of purity is achieved. In one embodiment, a compound of Formula XV has a purity of 90%, 91%, 92%, 93%, 94%, 95%, 96%, 97%, 98%, 99% or more.

In another embodiment, the invention pertains to a process for the preparation of a compound of Formula XVII

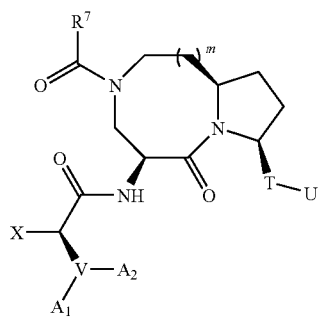

XVII comprising condensing a compound of Formula XVIII

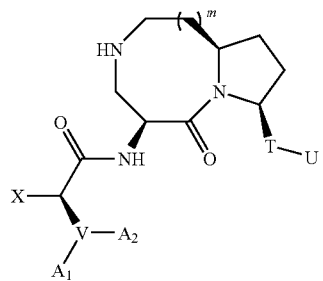

XVIII with R$^7$CO-L, wherein A$_1$, A$_2$, V, X, T, U and R$^7$ have the meanings as described above for Formula I, m is 1 or 2, and L is a leaving group. In one embodiment, L is Cl, OH or OBt. In one embodiment, m is 1.

In one embodiment, the condensation reaction is conducted in an inert organic solvent such as acetonitrile, benzene, chloroform, 1,2-dichloroethane, 1,2-dimethoxyethane, dimethylformamide, dimethylsulfoxide, dioxane, dichloromethane, N-methyl-2-pyrrolidinone or tetrahydrofuran. In another embodiment, the condensation reaction is carried out in tetrahydrofuran. In another embodiment, the condensation reaction is carried out in dichloromethane. In one embodiment, the condensation reaction is carried out at about −20° C. to about 25° C. In another embodiment, the condensation reaction is carried out at about 20° C. In one embodiment, the condensation reaction is complete in about 1 hour to about 48 hours. In another embodiment, the condensation reaction is complete in about 12 hours.

In one embodiment, L is —OH or —OBt. In another embodiment, the condensation reaction is carried out in the presence of an activating agent. In another embodiment, the activating agent is dicyclohexylcarbodiimide, 1-ethyl-3-(3-dimethylaminopropyl)carbodiimide or benzotriazol-1-yloxy)tripyrrolidinophosphonium hexafluorophosphate. In another embodiment, the activating agent is 1-ethyl-3-(3-dimethylaminopropyl)carbodiimide. In another embodiment, the condensation reaction is carried out in the presence of an activating agent and an additive that optimize reaction parameters such as purity and yield. In another embodiment, the additive is N-hydroxybenzotriazole.

The progress of the condensation reaction between a compound of Formula XVIII and R$^7$CO-L can be monitored by analytical methods known in the art such as TLC, LC, LC/MS, HPLC, NMR, etc. A compound of Formula XVII can be isolated and purified by any means known in the art such normal- and reverse-phase column chromatography (e.g., column chromatography on silica gel or reverse-phase HPLC), crystallization, extraction, etc. The product thus isolated can be subjected to further purification (e.g., recrystallization) until the desired level of purity is achieved. In one embodiment, a compound of Formula XVII has a purity of 90%, 91%, 92%, 93%, 94%, 95%, 96%, 97%, 98%, 99% or more.

The present invention also pertains to the preparation of a compound of Formula XIX

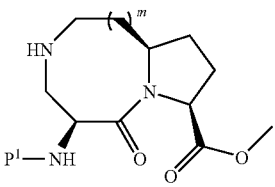

XIX wherein m is 1 or 2, and P$^1$ is an amine protecting group comprising:
a) condensing a compound of Formula XX

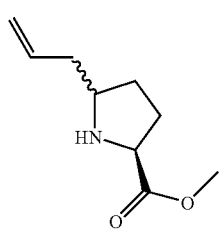

XX with a compound of formula XXI,

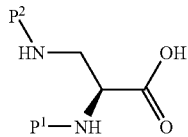

XXI wherein P¹ and P² are amine protecting groups, and P¹ does not equal P², to give a compound of Formula XXII

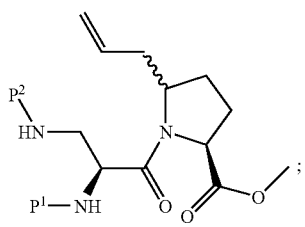

b) converting the alkene of Formula XXII to an aldehyde, to give a compound of Formula XXIII;

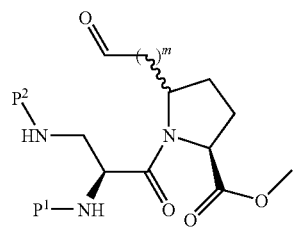

c) removing the P² amine protecting group of a compound of Formula XXIII to give a compound of Formula XXIV;

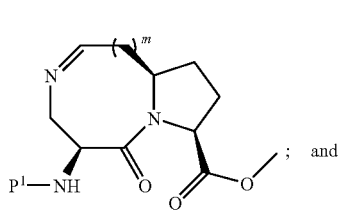

d) reducing the C=N double bond of a compound of Formula XXIV, to give a compound of Formula XIX.

In one embodiment, a compound of Formula XXI is N-α-(tert-butoxylcarbonyl)-N-β-(benzoxylcarbonyl)-L-diaminopropionic acid (Boc-Dap(Z)—OH). In one embodiment, the condensation of a compound of Formula XX with a compound of Formula XXI is carried out in the presence of an activating agent. In another embodiment, the activating agent is dicyclohexylcarbodiimide, 1-ethyl-3-(3-dimethylaminopropyl)carbodiimide or benzotriazol-1-yloxy)tripyrrolidinophosphonium hexafluorophosphate. In another embodiment, the activating agent is 1-ethyl-3-(3-dimethylaminopropyl) carbodiimide. In another embodiment, the condensation reaction is carried out in the presence of an activating agent and an additive that optimize reaction parameters such as purity and yield. In another embodiment, the additive is N-hydroxybenzotriazole.

Amine protecting groups P¹ and P² that are suitable for use in the processes of the present invention are well known, such as but not limited to trifluoroacetyl, t-butoxycarbonyl (Boc), benzyloxycarbonyl (CBz), allyloxycarbonyl (Alloc), trityl (triphenylmethyl), 9-fluorenylmethylenoxycarbonyl (Fmoc) and the like. Such groups are generally able to be selectively introduced and removed using mild reaction conditions that do not interfere with other portions of the subject compounds.

These protecting groups may be introduced or removed at a convenient stage using methods known from the art. The chemical properties of such protecting groups, methods for their introduction and their removal are known in the art and can be found for example in Greene and Wuts, "Protective Groups in Organic Synthesis," 3rd Ed., pp. 17-245 (J. Wiley & Sons, 1999), herein incorporated by reference in its entirety.

In one embodiment, P¹ and P² are selected from the group consisting of trifluoroacetyl, t-butoxycarbonyl (Boc), benzyloxycarbonyl (CBz), allyloxycarbonyl (Alloc), trityl (triphenylmethyl) and 9-fluorenylmethylenoxycarbonyl (Fmoc) such that P¹ does not equal P². In one embodiment, P¹ and P² are orthogonal protecting groups, i.e., the P¹ protecting group is capable of being selectively removed in the presence of the P² protecting group or the P² protecting group is capable of being selectively removed in the presence of the P¹ protecting group. Orthogonal protecting group strategies are known from the art. In one embodiment, P¹ is t-butoxycarbonyl (Boc). In one embodiment, P² is benzyloxycarbonyl (CBz). In one embodiment, P¹ is t-butoxycarbonyl (Boc) and P² is benzyloxycarbonyl (CBz).

In one embodiment, the condensation of a compound of Formula XX with a compound of Formula XXI is conducted in an inert organic solvent such as acetonitrile, benzene, chloroform, 1,2-dichloroethane, 1,2-dimethoxyethane, dimethylformamide, dimethylsulfoxide, dioxane, dichloromethane, N-methyl-2-pyrrolidinone or tetrahydrofuran. In another embodiment, the condensation of a compound of Formula XX with a compound of Formula XXI is carried out in tetrahydrofuran. In another embodiment, the condensation of a compound of Formula XX with a compound of Formula XXI is carried out in dichloromethane.

In one embodiment, the condensation of a compound of Formula XX with a compound of Formula XXI is carried out at about −20° C. to about 30° C. In another embodiment, the condensation reaction is carried out at about 20 to about 30° C. In one embodiment, the condensation reaction is complete in about 1 hour to about 48 hours. In another embodiment, the condensation reaction is complete in about 12 hours.

In another embodiment, the alkene of Formula XXII is treated with ozone to give the aldehyde of Formula XXIII, and m is 1. In one embodiment, the reaction with ozone is carried out in an inert organic solvent such as chloroform, 1,2-dichloroethane, dioxane, dichloromethane or tetrahydrofuran. In another embodiment, the reaction with ozone is carried out in dichloromethane. In one embodiment, the reaction with ozone is carried out at about −100° C. to about 0° C. In another embodiment, the reaction with ozone is carried at about −78° C. In one embodiment, the reaction with ozone is complete when the color of the reaction mixture turns blue, indicating an excessive amount of ozone in solution.

In one embodiment, the alkene of Formula XXII is first converted to a primary alcohol and the alcohol is oxidized to give an aldehyde of Formula XXIII, and m is 2. In one embodiment, the alkene of Formula XXII converted to a primary alcohol via hydroboration. In one embodiment, the hydroboration is carried out in an inert organic solvent such acetonitrile, benzene, 1,2-dimethoxyethane, dioxane, or tetrahydrofuran. In another embodiment, the hydroboration is carried out in tetrahydrofuran. In another embodiment, the hydroboration is carried out using 9-borabicyclo[3.3.1] nonane (9-BBN). In one embodiment, the primary alcohol is oxidized to the aldehyde with Dess-Martin periodinane to give an aldehyde of Formula XXIII, and m is 2. In one embodiment, the oxidation is carried out in an inert organic solvent such as dichloromethane. In one embodiment, the oxidation is carried out at about −20° C. to about 25° C. In another embodiment, the oxidation is carried out at about 20° C. In one embodiment, the oxidation is complete in about 1 hour to about 48 hours. In another embodiment, the oxidation is complete in about 12 hours.

In one embodiment, $P^2$ is a Cbz group. In another embodiment, $P^2$ is CBz and is cleaved by hydrogenation over palladium on carbon. In one embodiment, the hydrogenation is carried out in methanol, ethanol, 1-butanol, 2-butanol, 3-butanol, tert-butanol, 1-propanol or 2-propanol. In another embodiment, the hydrogenation is carried out in 2-propanol. In one embodiment, the hydrogenation is carried out at about 0° C. to about 40° C. In another embodiment, the hydrogenation is carried out at about 20° C. to about 30° C. In one embodiment, the hydrogenation is complete in about 1 hour to about 24 hours. In another embodiment, the hydrogenation is complete in about 12 hours.

In one embodiment, a compound of Formula XXIV is isolated prior to reduction of the C═N double bond. In one embodiment, a compound of Formula XXIV is isolated by filtration through celite. In one embodiment, a compound of Formula XXIV is isolated by filtration through celite followed by evaporation of the solvent(s).

In one embodiment, the C═N double bond of a compound of Formula XXIV is reduced with $H_2$ and palladium on carbon, $Na(CN)BH_3$ or $NaBH(OAc)_3$. In another embodiment, the reducing agent is $NaBH(OAc)_3$. In one embodiment, the reduction is carried out in an inert organic solvent such as methanol, ethanol, 1-butanol, 2-butanol, 3-butanol, tert-butanol, 1-propanol, 2-propanol, acetonitrile, benzene, chloroform, 1,2-dichloroethane, 1,2-dimethoxyethane, dimethylformamide, dimethylsulfoxide, dioxane, dichloromethane, N-methyl-2-pyrrolidinone or tetrahydrofuran. In another embodiment, the reduction is carried out in tetrahydrofuran. In one embodiment, the reduction is carried out at about 0° C. to about 25° C. In another embodiment, the reduction is carried out at about 20° C. to about 30° C. In one embodiment, the reduction is complete in about 1 hour to about 24 hours. In another embodiment, the reaction with ozone is complete in about 12 hours.

The progress of the any of the above reactions for the preparation of a compound of Formula XIX can be monitored by analytical methods known in the art such as TLC, LC, LC/MS, HPLC, NMR, etc. A compound of Formula XIX can be isolated and purified by any means known in the art such normal- and reverse-phase column chromatography (e.g., column chromatography on silica gel or reverse-phase HPLC), crystallization, extraction, etc. The product thus isolated can be subjected to further purification (e.g., recrystallization) until the desired level of purity is achieved. In one embodiment, a compound of Formula XIX has a purity of 90%, 91%, 92%, 93%, 94%, 95%, 96%, 97%, 98%, 99% or more.

The compounds of this invention may be prepared using methods known to those of skill in the art. Specifically, compounds of Formulae I-XXIII can be prepared as illustrated by the exemplary reactions in the Examples.

An important aspect of the present invention is that compounds of Formulae I-X induce apoptosis and also potentiate the induction of apoptosis in response to apoptosis induction signals. Therefore, it is contemplated that these compounds sensitize cells to inducers of apoptosis, including cells that are resistant to such inducers. The IAP inhibitors of the present invention can be used to induce apoptosis in any disorder that can be treated, ameliorated, or prevented by the induction of apoptosis. Thus, the present invention provides compositions and methods for targeting animals characterized as overexpressing an IAP protein. In some of the embodiments, the cells (e.g., cancer cells) show elevated expression levels of IAP proteins as compared to non-pathological samples (e.g., non-cancerous cells). In other embodiments, the cells operationally manifest elevated expression levels of IAP proteins by virtue of executing the apoptosis program and dying in response to an inhibiting effective amount of a compound of Formulae I-X, said response occurring, at least in part, due to the dependence in such cells on IAP protein function for their survival.

In another embodiment, the invention pertains to modulating an apoptosis-associated state which is associated with one or more apoptosis-modulating agents. Examples of apoptosis-modulating agents include, but are not limited to, Fas/CD95, TRAMP, TNF RI, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Akt, CAD, PI3 kinase, PP1, and caspase proteins. Other agents involved in the initiation, decision and degradation phase of apoptosis are also included. Examples of apoptosis-modulating agents include agents, the activity, presence, or change in concentration of which, can modulate apoptosis in a subject. Preferred apoptosis-modulating agents are inducers of apoptosis, such as TNF or a TNF-related ligand, particularly a TRAMP ligand, a Fas/CD95 ligand, a TNFR-1 ligand, or TRAIL.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections (e.g., as antiulcerous agents, e.g., in the context of *H. pylori* infection); hyperproliferative diseases; AIDS; degenerative conditions; vascular diseases (e.g., primary varicosis) and the like. The compounds of the present invention may also be useful in the treatment of diseases in which there is a defect in the programmed cell-death or the apoptotic machinery e.g., multiple sclerosis, asthma, atherosclerosis and the like. In some embodiments, the cancer cells being treated are metastatic. In other embodiments, the cancer cells being treated are resistant to anticancer agents.

In some embodiments, infections suitable for treatment with the compositions and methods of the present invention include, but are not limited to, infections caused by viruses, bacteria, fungi, mycoplasma, prions, and the like.

Some embodiments of the present invention provide methods for administering an effective amount of a compound of Formulae I-X and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies).

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTA-SONE, dexamethasone, dexamethasone intensol, DEXONE, HEXADROL, hydroxychloroquine, METICORTEN, ORA-DEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of Formulae I-X and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethyleninines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| Drug | Brand | Company |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of Mycobacterium bovis (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl]benzoic acid) | Targretin | Ligand Pharmaceuticals |
| bexarotene gel | Targretin | Ligand Pharmaceuticals |
| Bleomycin (cytotoxic glycopeptide antibiotics produced by Streptomyces verticillus; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl]benzenesulfonamide) | Celebrex | Searle Pharmaceuticals, England |
| Chlorambucil (4-[bis(2chlor-ethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino]tetra-hydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by Streptomyces parvullus, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanedi-yl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17- | Emcyt | Pharmacia & Upjohn Company |

TABLE 1-continued

| Drug | Brand | Company |
|---|---|---|
| (dihydrogen phosphate), disodium salt, monohydrate) | | |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-methylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl)nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)[6],Azgly[10]LHRH; pyro-Glu-His-Trp-Ser-Tyr-D-Ser(But)-Leu-Arg-Pro-Azgly-NH2 acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexo-pyranosyl)oxy]-7,8,9,10-tetrahydro-6,9,11-trihydroxy-hydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazin-yl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyl-oxy]-1H-pyrano[3',4':6,7]indoli-zino[1,2-b]quinoline-3,14(4H,12H) dione hydrochloride trihydrate) | Camptosar | Pharmacia & Upjohn Company |
| Lenalidomide 3-(4-amino-1-oxo 1,3-dihydro-2H-isoindol-2-yl)piperidine-2,6-dione | Revlimid | Celgene |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8-hexa-hydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5,6-tetrahydro-6-phenylimidazo [2,1-b] thiazole monohydrochloride $C_{11}H_{12}N_2S$•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methyl-amino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl)ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexane-diamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase | Adagen | Enzon |

TABLE 1-continued

| | | |
|---|---|---|
| ((monomethoxypolyethylene glycol succinimidyl) 11-17-adenosine deaminase) | (Pegademase Bovine) | Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbon-yl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethyl-ethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyl-adriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexo-pyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity but are not currently approved by the U.S. Food and Drug Administration or other counterpart agencies or are undergoing evaluation for new uses. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

In one embodiment, the anticancer agent is selected from the group consisting of taxotere, gemcitabine, lapatinib (Tykerb®) and etoposide.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of Formulae I-X with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitro aniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotetrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to an animal preferably is about 0.01 Gray (Gy) to about 100 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, a compound of Formulae I-X and one or more therapeutic agents or anticancer agents are administered to an animal under one or more of the following conditions: at different periodicities, at different durations, at different concentrations, by different administration routes, in a single composition, in separate compositions, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. For example, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, e.g., from about 0.01 to about 5 mg/kg.

The unit oral dose may comprise from about 0.01 to about 1000 mg, e.g., about 0.1 to about 100 mg of the compound. The unit dose may be administered one or more times daily as one or more tablets or capsules each containing from about 0.1 to about 10, conveniently about 0.25 to 50 mg of the compound or its solvates.

In a topical formulation, the compound may be present at a concentration of about 0.01 to 100 mg per gram of carrier. In one embodiment, the compound is present at a concentration of about 0.07-1.0 mg/ml, e.g., about 0.1-0.5 mg/ml, e.g., about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, e.g., from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by dissolving the active ingredient, in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Synthesis of Covalently Constrained Smac Mimetics

General Methods: NMR spectra were acquired at a proton frequency of 300 MHz. $^1$H chemical shifts are reported with Me$_4$Si (0.00 ppm), CHCl$_3$ (7.26 ppm), CD$_2$HOD (3.31 ppm), or DHO (4.79 ppm) as internal standards. $^{13}$C chemical shifts are reported with CDCl$_3$ (77.00 ppm), CD$_3$OD (49.00 ppm), or 1,4-dioxane (67.16 ppm) as internal standards. Optical rotations were measured at room temperature. Compounds of the invention may be purified by reverse phase HPLC (0.1% TFA in water and 0.1% TFA in acetonitrile as the eluent) and isolated as the TFA salt.

General Procedure A (Condensation Between Carboxylic Acid and Amine):

To a solution of the two substrates in CH$_2$Cl$_2$ (20 mg/mL for the minor substrate) was added EDC (1.1 eq per amino group), HOBt (1.1 eq per amino group) and N,N-diisopropylethyl amine (4 eq per amino group) at 0° C. with stirring. The mixture was stirred at room temperature for eight hours and then concentrated. The residue was purified by chromatography to give the product.

General Procedure B (Deprotection of Boc):

To a solution of the substrate in methanol (20 mg/mL) was added a solution of HCl in 1,4-dioxane (4 M, 10-20 eq per Boc). The solution was stirred at room temperature overnight and then condensed to give the product.

EXAMPLE 2

Synthesis of Smac Mimetic Intermediates

Intermediates in the synthetic pathway for conformationally constrained Smac mimetics may be synthesized using methodology described in Schemes 1-7.

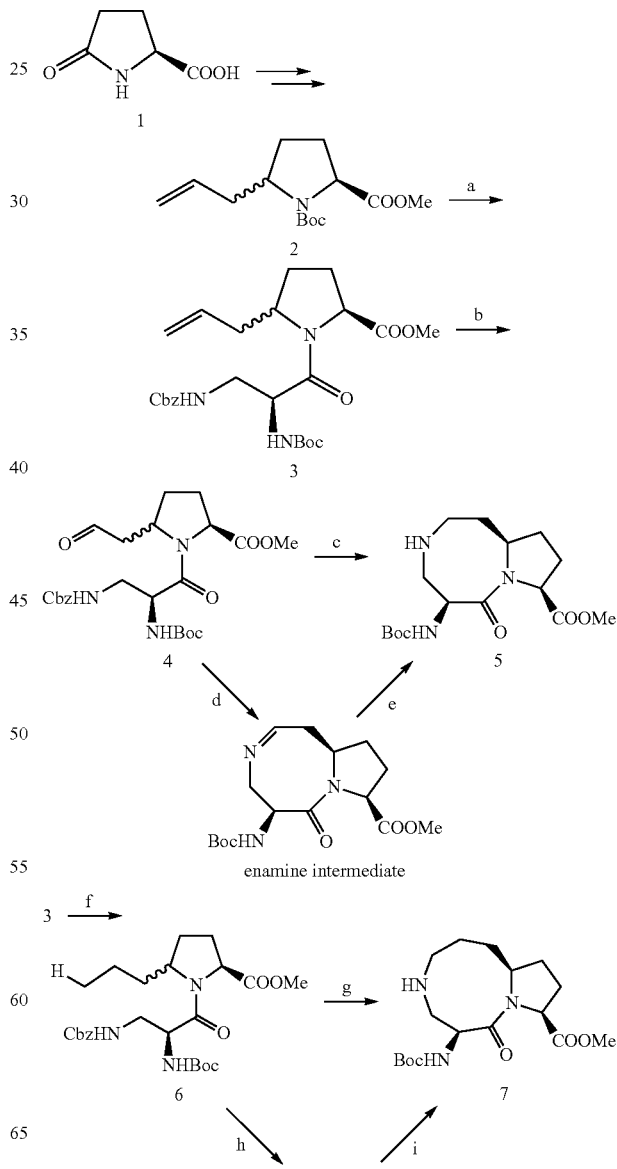

Scheme 1

-continued

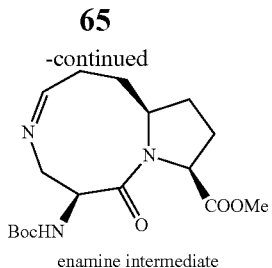

enamine intermediate

Reagents and conditions:(a) i. 4N HCl in 1,4-dioxane, methanol; ii. Boc-Dap(Z)-OH, EDC, HOBt, N,N-diisopropylethylamine, CH$_2$Cl$_2$, 52% over two steps; (b) O$_3$, then PPh$_3$, CH$_2$Cl$_2$, 90%; (c) H$_2$, 10% Pd—C, i-PrOH, 41%; (d) H$_2$, 10% Pd—C, i-PrOH; (e) NaBH(OAc)$_3$, THF; (f) 9-BBN (2 eq), THF, reflux, 12 h, then 3N NaOH (2 eq), 35% H$_2$O$_2$ (2.5 eq), 0° C.-rt, 85%; (f) i. Dess-Martin periodinane, CH$_2$Cl$_2$; ii. H$_2$, 10% Pd—C, i-PrOH, 50% over two steps; (h) H$_2$, 10% Pd—C, i-PrOH; (i) NaBH(OAc)$_3$, THF.

The synthesis of intermediates 5 and 7 is shown in Scheme 1. Compound 2 may be prepared in five steps from pyroglutamic acid 1 according to reported methods (see: (1) Zhang, J.; Xiong, C.; Wang, W.; Ying, J.; Hruby, V., J. *Org. Lett.*, 2002, 4 (23), 4029-4032, (2) Polyak, F. and Lubell, W. D. *J. Org, Chem.* 1998, 63, 5937-5949, and (3) *Tetrahedron Letters* 2005, 46, 945-947) as a mixture of two diastereoisomers with the R form isomer as the major product (ratio is about 4:1). Removal of the Boc group in 2 followed by condensation with N-α-(tert-butoxylcarbonyl)-N-β-(benzoxylcarbonyl)-L-diamino-propionic acid (Boc-Dap(Z)—OH) gave amide 3. Ozone oxidation of the C—C double bond in 3 yielded aldehyde 4. Cleavage of the Cbz group in 4, intramolecular condensation of the resulting amine with the aldehyde group and subsequent reduction of the enamine were realized in one pot to give compound 5 under prolonged reaction times. Alternatively, deprotection of the CBz group of 4, intramolecular cyclization, isolation of the enamine intermediate and reduction provides 5. In this transformation only compound 5 was obtained and there was no detectable formation of its isomer, suggesting that the amino aldehyde from the minor isomer does not cyclize under these conditions.

To a solution of compound 2 (540 mg, 2 mmol) in 20 mL of methanol was added 4 ml, of a solution of 4 N HCl in 1,4-dioxane. The solution was stirred at room temperature overnight and then concentrated to give an ammonium salt. To a mixture of this salt in 15 mL of dichloromethane were added 1.17 g (2.4 eq) of Boc-Dap(Z)—OH.DCHA, 460 mg (2.4 mmol) of EDC, 320 mg (2.4 mmol) of HOBt, and 3 mL of N,N-diisopropylethyl amine. The mixture was stirred at room temperature overnight and then condensed. The residue was purified by chromatography to afford compound 3 (YP-348) (580 mg, 59%). $^1$H NMR (300 MHz, CDCl$_3$, TMS) (major isomer) δ 7.34-7.28 (m, 5H), 5.80-5.77 (m, 1H), 5.59 (m, 1H), 5.36-5.33 (d, J=10.0 Hz, 2H), 5.19-5.01 (m, 4H), 4.67-4.62 (m, 1H), 4.47-4.44 (m, 1H), 3.76-3.74 (s, 1H), 3.74-3.71 (s, 2H), 2.32-2.30 (m, 1H), 2.16-2.12 (m, 1H), 1.99-1.95 (m, 2H), 1.42 (s, 9H); $^{13}$C NMR (75 MHz, CDCl$_3$) δ 172.4, 170.5, 156.5, 155.2, 136.4, 134.6, 133.8, 128.3, 127.9, 118.5, 117.1, 80.0, 66.6, 59.7, 58.2, 52.6, 43.4, 29.2, 28.1, 26.6.

O$_3$ was bubbled through a solution of compound 3 (490 mg, 1 mmol) in 20 mL of CH$_2$Cl$_2$ at −78° C. until the color turned to pale blue. O$_3$ was bubbled for 15 min more before air was bubbled to get rid of excessive O$_3$. After adding 3 mL of Et$_3$N, the mixture was warmed to room temperature and stirred for 1 h. The solvent was evaporated and the residue was purified by chromatography to give aldehyde 4 (YP-367) (340 mg, 69%). $^1$H NMR (300 MHz, CDCl$_3$, TMS) (major isomer) δ 9.78-9.67 (m, 1H), 7.53-7.32 (m, 5H), 5.44 (s, 1/2 H), 5.32 (s, 1/2 H), 5.15-5.06 (m, 2H), 4.64 (m, 1H), 4.40-4.39 (m, 1H), 3.78-3.76 (s, 3/2 H), 3.76-3.74 (s, 3/2 H), 3.48-3.42 (m, 3H), 2.78-2.52 (m, 1H), 2.40-2.20 (m, 1H), 2.16 (m, 2H), 2.06-1.89 (m, 1H), 1.44-1.43 (m, 9H); $^{13}$C NMR (75 MHz, CDCl$_3$) δ 200.3, 199.5, 172.6, 172.2, 170.3, 156.5, 136.4, 128.4, 128.0, 66.7, 59.7, 59.1, 54.3, 52.4, 52.3, 48.4, 43.3, 29.6, 28.2, 21.0.

To a solution of compound 4 (290 mg, 0.6 mmol) in 20 mL of isopropanol was added 0.2 g of 10% Pd/C. The mixture was stirred at room temperature under H$_2$ overnight, filtered through celite and concentrated. The residue was dissolved in dry THF. To this solution was added NaBH(OAc)$_3$ (380 mg, 1.8 mmol). The mixture was stirred at room temperature overnight, diluted with CH$_2$Cl$_2$, washed with brine, dried over Na$_2$SO$_4$ and concentrated. The residue was purified by chromatography to give compound 5 (72 mg, 35%). $[\alpha]^{20}_D$ −30.2 (c=1.7, CHCl$_3$); $^1$H NMR (300 MHz, CDCl$_3$, TMS) δ 5.45 (brd, J=8.0 Hz, 1H), 4.67 (m, 1H), 4.52 (t, J=9.0 Hz, 1H), 4.23 (m, 1H), 3.74 (s, 3H), 3.20 (m, 2H), 2.94 (m, 1H), 2.74 (dd, J=13.6, 10.9 Hz, 1), 2.35 (m, 1H), 2.14 (m, 1H), 1.99 (m, 1H), 1.86-1.74 (m, 3H), 1.66 (m, 1H), 1.43 (brs, 9H); 13C NMR (75 MHz, CDCl$_3$, TMS) δ 173.42, 170.60, 155.16, 79.68, 59.46, 58.39, 54.92, 52.44, 46.72, 37.45, 32.15, 29.64, 28.29, 26.98.

Hydroboration of the C—C double bond in 3 with 9-BBN followed by alkaline oxidation of the resulted borane afforded alcohol 6. Oxidation of 6 with Dess-Martin periodinane furnished a mixture of two aldehydes, which was cyclized in the same procedure as that for compound 5 to give compound 7. Similar to 5, during this transformation only one isomer was obtained.

Analytical data for compound 7: $[\alpha]^{20}_D$ −23.2 (c=1.0, CHCl$_3$); $^1$H NMR (300 MHz, CDCl$_3$, TMS) δ 5.23 (brd, J=8.0 Hz, 1H), 4.79 (m, 1H), 4.65 (dd, J=9.7, 8.2 Hz), 4.22 (m, 1H), 3.74 (s, 3H), 3.02-2.80 (m, 4H), 2.38-1.70 (m, 9H), 1.43 (brs, 9H); $^{13}$C NMR (75 MHz, CDCl$_3$, TMS) δ 173.38, 171.59, 155.09, 79.68, 62.03, 59.82, 53.72, 53.15, 52.48, 50.09, 34.66, 34.55, 29.47, 28.31, 27.33.

Scheme 2

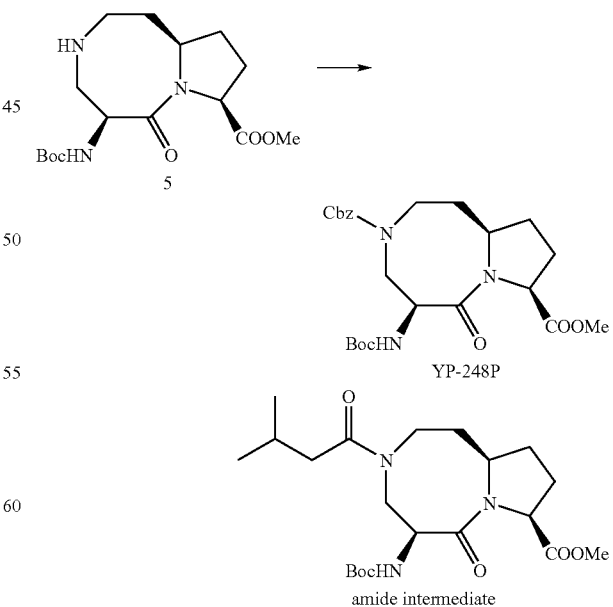

Analytical data for YP-248P: $^1$H NMR shows that this compound has two rotamers with a ratio of 2:1. $^1$H NMR (300

MHz, CDCl₃, TMS) δ 7.47-7.44 (m, 1H), 7.38-7.32 (m, 4H), 5.65-5.62 (d, J=8 Hz, 1H), 5.31-5.16 (m, 2H), 4.64-4.60 (m, 1H), 4.51-4.46 (t, J=8 Hz, 1H), 4.24-4.23 (m, 1H), 4.23-4.21 (m, 1H), 3.75 (s, 1H), 3.73 (s, 2H), 3.66-3.63 (m, 1H), 3.63-3.61 (m, 1H), 3.61-3.31 (m, 1H), 2.36-2.34 (m, 1H), 2.11-1.76 (m, 6H), 1.44-1.45 (s, 9H).

Analytical data for amide intermediate: $^1$H NMR (300 MHz, CDCl₃, TMS) δ 5.79 (brd, J=7.0 Hz, 1H), 4.50-4.35 (m, 2H), 4.05 (m, 1H), 3.98-3.85 (m, 2H), 3.70 (s, 3H), 3.32-3.04 (m, 2H), 2.54 (m, 1H), 2.40-2.26 (m, 2H), 2.25-1.60 (m, 6H), 1.39 (s, 9H), 0.98-0.89 (m, 6H); $^{13}$C NMR (75 MHz, CDCl₃) δ 173.12, 172.52, 168.85, 154.69, 79.80, 59.51, 56.11, 54.38, 53.51, 52.23, 46.18, 42.02, 32.51, 31.12, 28.12, 26.54, 25.81, 22.69, 22.40.

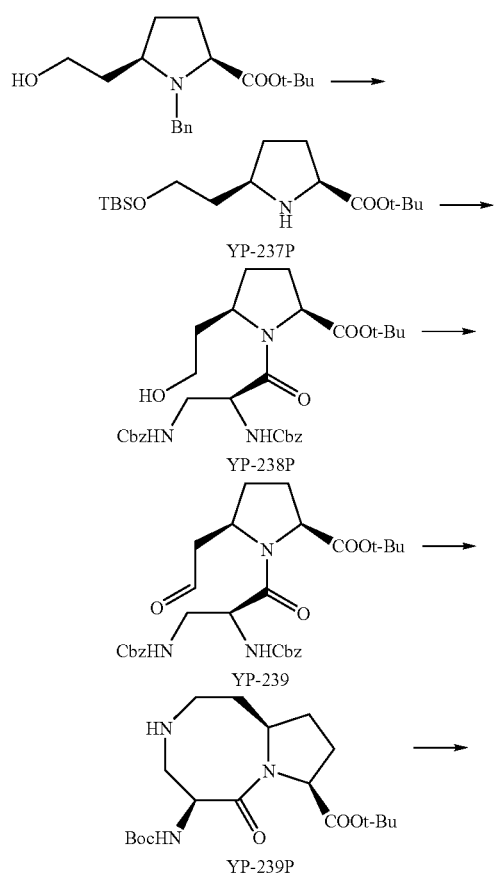

Analytical data for YP-237P: $[\alpha]^{20}_D$ −21.5° (c=1.0, CHCl₃); $^1$H NMR (300 MHz, CDCl₃, TMS) δ 3.71 (t, J=6.5 Hz, 3H), 3.60 (dd, J=9.0, 5.4 Hz, 1H), 3.11 (m, 1H), 2.05 (m, 1H), 1.95-1.63 (m, 3H), 1.46 (s, 9H), 1.25 (m, 1H), 0.89 (s, 9H), 0.05 (s, 6H); $^{13}$C NMR (75 MHz, CDCl₃) δ 174.5, 80.8, 61.5, 60.6, 57.5, 38.8, 31.8, 30.4, 28.0, 25.9, 18.2, −5.4; HRMS: calcd. m/z for [M+H]⁺ 330.2464; found 330.2466.

Analytical data for YP-238P: $[\alpha]^{20}_D$ −90.0° (c=1.67, CHCl₃); $^1$H NMR shows this compound has two rotamers with a ratio of 1:1. $^1$H NMR (300 MHz, CDCl₃, TMS) δ 7.28 (m, 5H), 5.59 (m, 1H), 5.35 (m, 1H), 5.20-5.05 (m, 2H), 4.85 (m, 1/2 H), 4.65 (m, 1/2 H), 4.46 (m, 1H), 4.35 (m, 1H), 3.80 (m, 1/2 H), 3.70-3.50 (m, 2H), 3.40 (m, 1H), 3.25 (m, 1/2 H), 2.32 (m, 1H), 2.20-1.50 (m, 4H), 1.46 (s, 4.5H), 1.44 (s, 4.5H), 1.43 (s, 4.5H), 1.41 (s, 4.5H); HRMS: calcd m/z 558.2791 for [M+Na]⁺; found 558.2794.

Analytical data for YP-239: $[\alpha]^{20}_D$ −51.6° (c=1.67, CHCl₃); $^1$H NMR shows that this compound has two rotamers with a ratio of 2:1. $^1$H NMR (300 MHz, CDCl₃, TMS) δ 9.76 (s, 2/3 H), 9.71 (s, 1/3 H), 7.40-7.28 (m, 5H), 5.72-5.30 (m, 2H), 5.20-4.95 (m, 2H), 4.90-4.25 (m, 3H), 3.52-3.05 (m, 3H), 2.90-1.60 (m, 4H), 1.50-1.35 (m, 18H); HRMS: calcd m/z 556.2635 for [M+Na]⁺; found 556.2629.

Analytical data for YP-239P: $[\alpha]^{20}_D$ −8.4° (c=0.65, CHCl₃); $^1$H NMR (300 MHz, CDCl₃, TMS) δ 5.49 (brd, J=8.1 Hz, 1H), 4.70 (m, 1H), 4.41 (t, J=9.3 Hz, 1H), 4.30 (m, 1H), 3.25-3.18 (m, 2H), 2.89 (m, 1H), 2.75 (dd, J=13.5, 11.1 Hz, 1H), 2.34 (m, 1H), 2.18-1.60 (m, 6H), 1.49 (s, 9H), 1.44 (s, 9H); $^{13}$C NMR (75 MHz, CDCl₃) δ 171.8, 170.4, 155.2, 81.7, 79.5, 60.6, 58.5, 54.9, 52.3, 46.9, 37.5, 32.1, 28.3, 28.0, 27.0; HRMS: calcd m/z 406.2318 for [M+Na]⁺; found 406.2317.

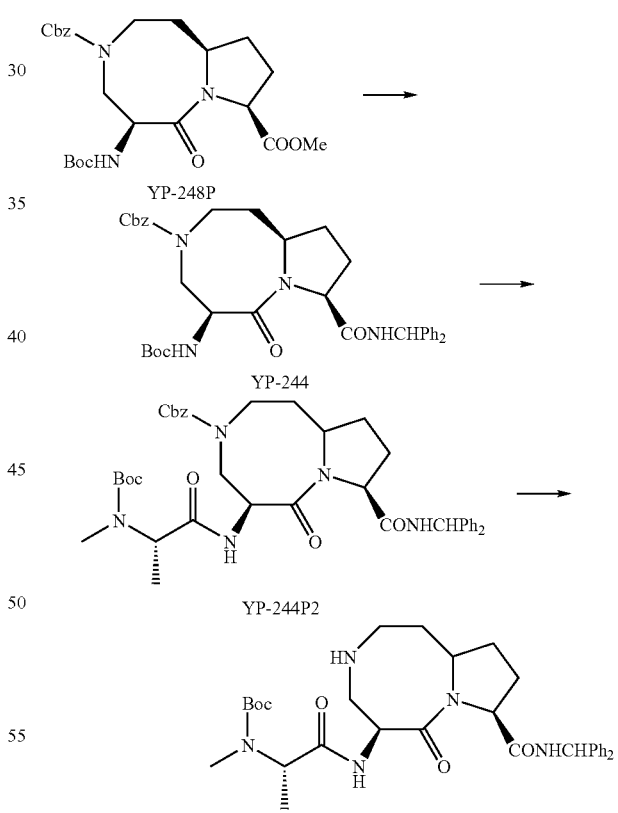

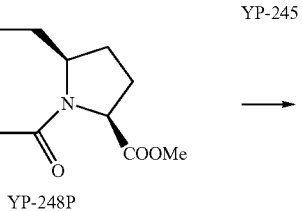

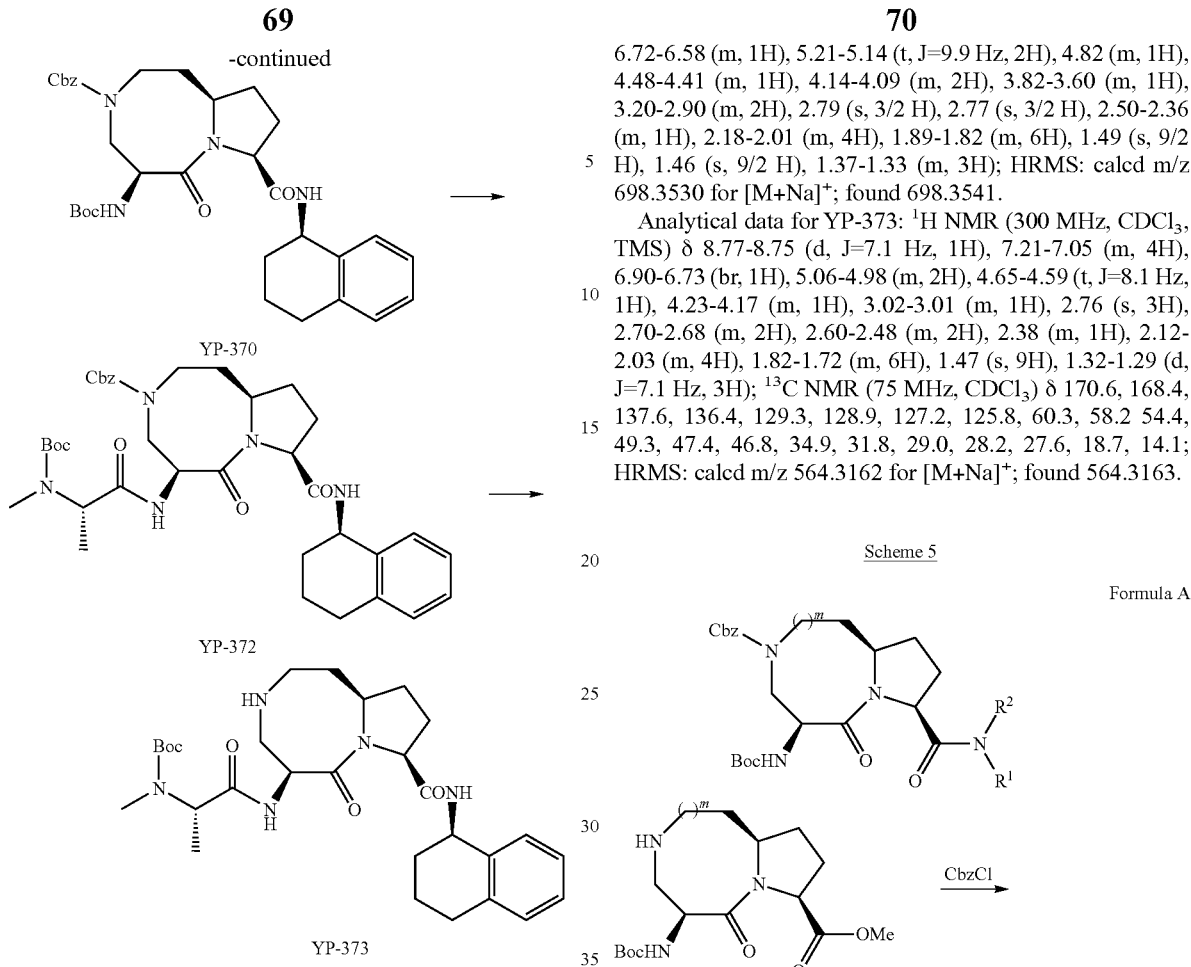

YP-370

YP-372

YP-373

Analytical data for YP-244: ¹H NMR (300 MHz, CDCl₃, TMS) δ 7.92-7.75 (m, 1H), 7.48-7.46 (m, 1H), 7.37-7.24 (m, 15H), 6.24-6.18 (t, J=8.3 Hz, 1H), 5.76-5.70 (t, J=7.3 Hz, 1H), 5.15 (s, 2H), 4.70-4.65 (m, 1H), 4.57-4.54 (m, 1H), 4.15-4.10 (m, 2H), 3.60-3.40 (m, 1H), 2.67-2.61 (m, 2H), 2.12-2.01 (m, 2H), 1.82-1.76 (m, 2H), 1.48-1.47 (s, 9H).

Analytical data for YP-244P2: ¹H NMR shows that this compound has two rotamers with a ratio of 1:1. ¹H NMR (300 MHz, CDCl₃, TMS) δ 7.83-7.69 (m, 1H), 7.47-7.45 (m, 1H), 7.36-7.26 (m, 15H), 6.24-6.18 (t, J=8.2 Hz, 1H), 5.15 (s, 2H), 4.89-4.79 (m, 1H), 4.70-4.62 (q, J=6.9 Hz, 1H), 4.23-4.07 (m, 2H), 3.60-3.47 (1H), 2.82 (s, 3/2 H), 2.79 (s, 3/2 H), 2.62-2.59 (m, 2H), 2.48-2.30 (m, 1H), 2.13-2.03 (m, 2H), 1.86-1.79 (m, 2H), 1.51 (s, 9/2 H), 1.49 (s, 9/2 H), 1.38-1.35 (d, J=7.0 Hz, 3H).

Analytical data for YP-245: ¹H NMR (300 MHz, CDCl₃, TMS) δ 9.09-9.07 (d, J=7.2 Hz, 1H), 7.32-7.18 (m, 10H), 6.99-6.80 (br, 1H), 6.23-6.20 (d, J=7.3 Hz, 1H), 5.08-5.04 (m, 1H), 4.72-4.67 (t, J=8.5 Hz, 1H), 4.33-4.18 (m,1H), 307-2.94 (m, 1H), 2.80 (s, 3H), 2.73-2.54 (m, 1H), 2.53-2.38 (m, 1H), 2.31-2.24 (t, J=11 Hz, 1H), 2.18-2.00 (m, 2H), 1.75-1.74 (m, 2H), 1.53 (s, 9H), 1.35-1.26 (d, J=7.1 Hz, 3H).

Analytical data for YP-370: ¹H NMR (300 MHz, CDCl₃, TMS) δ 7.60-7.05 (m, 9H), 5.78-5.50 (m, 1H), 5.20-5.11 (m, 2H), 4.65-4.30 (m, 2H), 4.28-4.22 (m, 1H), 3.60-3.48 (m, 1H), 3.42-3.38 (m, 1H), 2.93-2.68 (m, 2H), 2.58-2.40 (m, 1H), 2.28-1.98 (m, 4H), 1.98-1.70 (m, 6H), 1.44 (s, 9H).

Analytical data for YP-372: ¹H NMR shows that this compound has two rotamers with a ratio of 1:1. ¹H NMR (300 MHz, CDCl₃, TMS) δ 7.45 (m, 1H), 7.36-7.10 (m, 9H), 6.72-6.58 (m, 1H), 5.21-5.14 (t, J=9.9 Hz, 2H), 4.82 (m, 1H), 4.48-4.41 (m, 1H), 4.14-4.09 (m, 2H), 3.82-3.60 (m, 1H), 3.20-2.90 (m, 2H), 2.79 (s, 3/2 H), 2.77 (s, 3/2 H), 2.50-2.36 (m, 1H), 2.18-2.01 (m, 4H), 1.89-1.82 (m, 6H), 1.49 (s, 9/2 H), 1.46 (s, 9/2 H), 1.37-1.33 (m, 3H); HRMS: calcd m/z 698.3530 for [M+Na]⁺; found 698.3541.

Analytical data for YP-373: ¹H NMR (300 MHz, CDCl₃, TMS) δ 8.77-8.75 (d, J=7.1 Hz, 1H), 7.21-7.05 (m, 4H), 6.90-6.73 (br, 1H), 5.06-4.98 (m, 2H), 4.65-4.59 (t, J=8.1 Hz, 1H), 4.23-4.17 (m, 1H), 3.02-3.01 (m, 1H), 2.76 (s, 3H), 2.70-2.68 (m, 2H), 2.60-2.48 (m, 2H), 2.38 (m, 1H), 2.12-2.03 (m, 4H), 1.82-1.72 (m, 6H), 1.47 (s, 9H), 1.32-1.29 (d, J=7.1 Hz, 3H); ¹³C NMR (75 MHz, CDCl₃) δ 170.6, 168.4, 137.6, 136.4, 129.3, 128.9, 127.2, 125.8, 60.3, 58.2 54.4, 49.3, 47.4, 46.8, 34.9, 31.8, 29.0, 28.2, 27.6, 18.7, 14.1; HRMS: calcd m/z 564.3162 for [M+Na]⁺; found 564.3163.

Scheme 5

Formula A

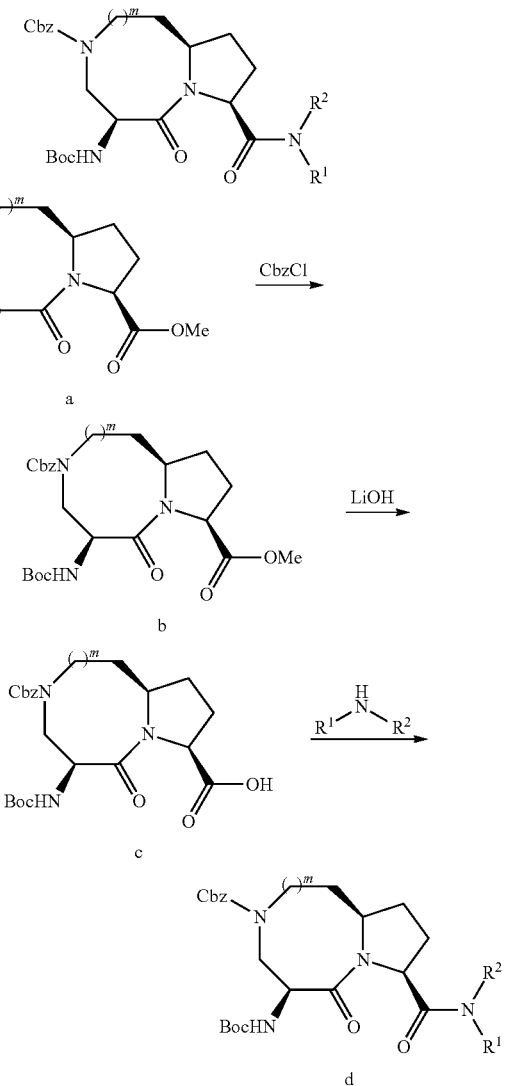

A compound represented by formula A, wherein m is 1-2, and R¹ and R² are independently selected from the group consisting of hydrogen, optionally substituted alkyl, optionally substituted carbocyclic, optionally substituted heterocyclic, optionally substituted aryl and optionally substituted heteroaryl, may be prepared by the method shown in Scheme 5. Briefly, protection of the amino group in intermediate a with the Cbz protecting group gives intermediate b. Hydrolysis of the ester group of b yields acid c. Condensation of c with amine $NR^1R^2$ furnishes a compound of Formula A.

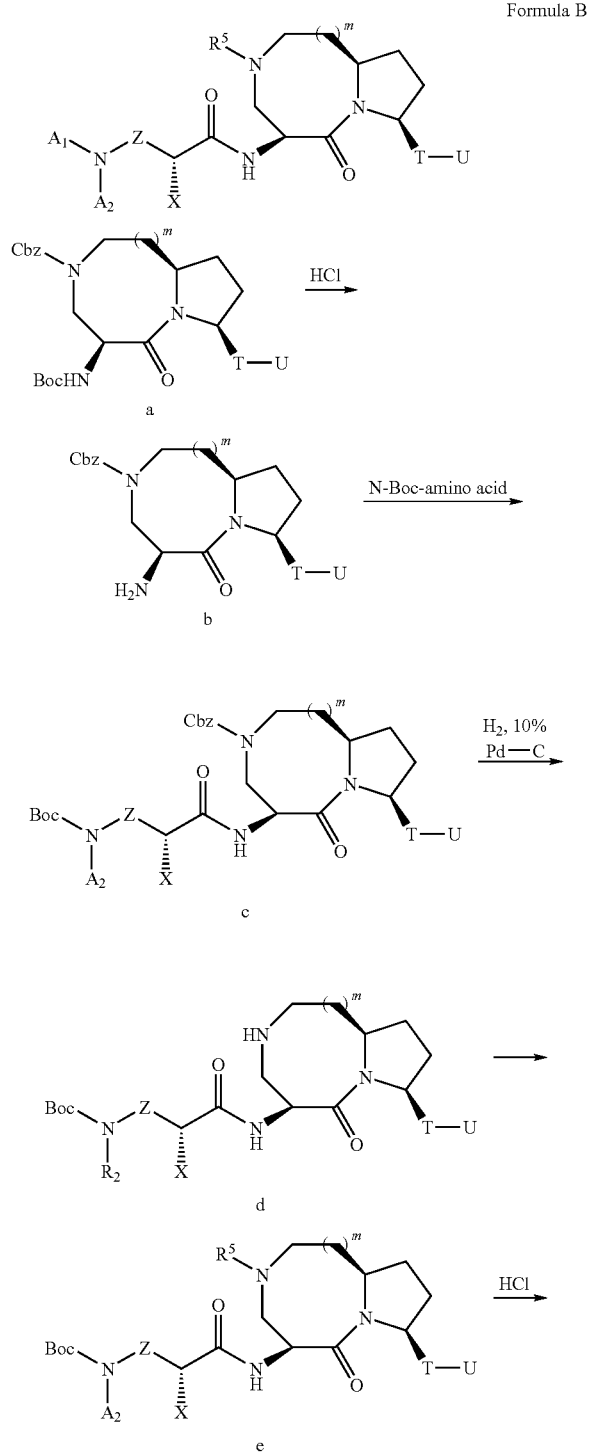

A compound represented by Formula B wherein $A_1$, $A_2$, Z, X, T, U, m and $R^5$ have the meanings as described above for Formula I, may be prepared as shown in Scheme 6. Briefly, removal of the Boc protecting group in a provides amine b. Condensation of b with corresponding Boc-protected amino acid gives amide c. Removal of the Cbz protecting group in c furnishes amine d. Introduction of $R^5$ to the amino group in d yielded e. $R^5$ can be introduced by substitution of d with corresponding alkyl halide (e.g., MeI) or by other nucleophilic displacement reactions with suitable electrophiles. When $R^5$ is $COR^7$, $COR^7$ can be introduced by condensation of d with $R^7$CO-L wherein L is a leaving group. For example, $R^7$CO-L can be the corresponding carboxylic acid (i.e., $R^7CO_2H$) or acid chloride (i.e., $R^7COCl$). Removal of the Boc protecting group in e affords f. Introduction of the $A_1$ group by substitution of f with an alkyl halide or reductive amination of f with the corresponding aldehyde provides Smac mimetic represented by Formula B.

In one embodiment, $COR^7$ is introduced by condensation of d with the corresponding carboxylic acid (i.e., $R^7CO_2H$). In another embodiment, the condensation of $R^7CO_2H$ with d is carried out in the presence of an activating agent (e.g., dicyclohexylcarbodiimide, 1-ethyl-3-(3-dimethylaminopropyl)carbodiimide, benzotriazol-1-yloxy)tripyrrolidinophosphonium hexafluorophosphate). In another embodiment, the activating agent is 1-ethyl-3-(3-dimethylaminopropyl)carbodiimide. In another embodiment, the condensation of $R^7CO_2H$ with d is carried out in the presence of an activating agent and one or more additional additives (e.g., N-hydroxybenzotriazole) to optimize reaction parameters such as yield. In one embodiment, the reaction is complete in about 1 hours to about 24 hours. In one embodiment, the reaction is carried out at a temperature of about −20° C. to about 25° C. In one embodiment, the reaction is carried out in an inert organic solvent such as acetonitrile, benzene, chloroform, 1,2-dichloroethane, 1,2-dimethoxyethane, dimethylformamide, dimethylsulfoxide, dioxane, dichloromethane, N-methyl-2-pyrrolidinone or tetrahydrofuran.

Scheme 7

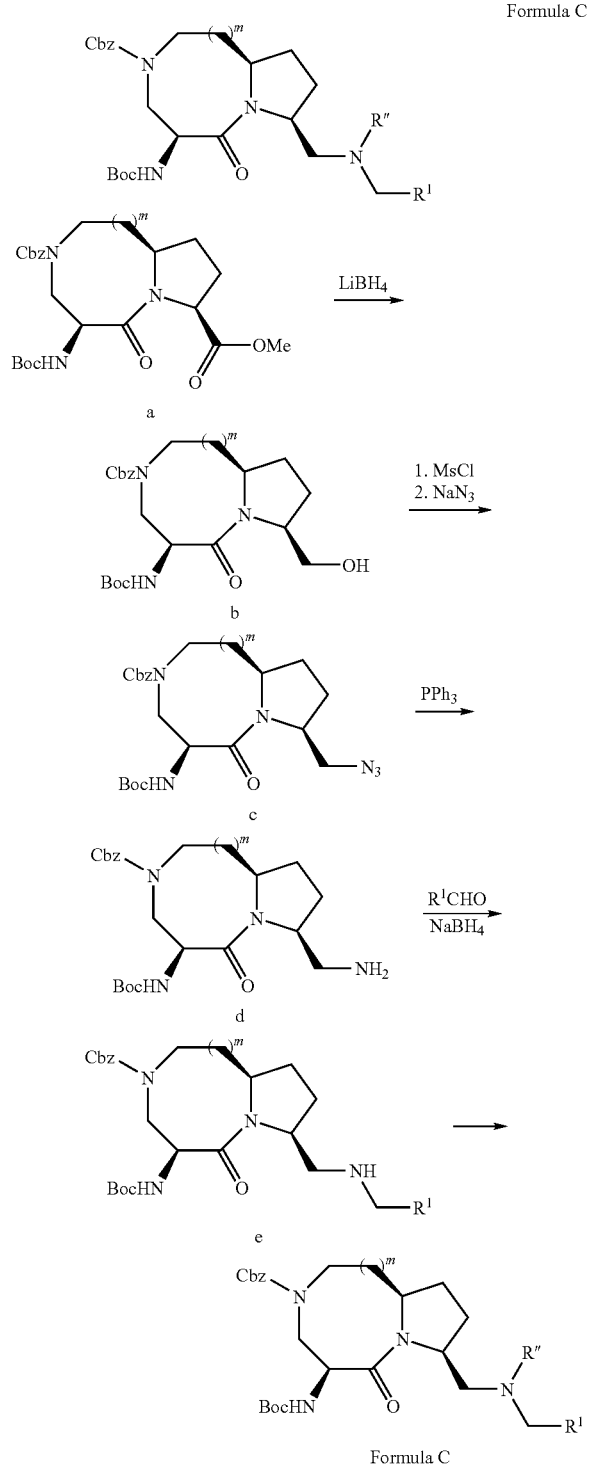

Formula C

R" = R² or COR⁷

A compound represent by Formula C wherein m is 1 or 2, and $R^1$, $R^2$ and $R^7$ have the meanings described above for Formula I, can be synthesized in the method shown in Scheme 7. Reduction of the ester group in a yields an alcohol b. Mesylation of the hydroxyl group in b followed by substitution of the resulted mesylate with sodium azide furnishes azide c. Reduction of the azide with $PPh_3$ in $THF-H_2O$ provides amine d. Reductive amination of d with an aldehyde $R^1CHO$ gives amine e. Introduction of R" to the amino group in e affords a compound of Formula C. When R" is $R^2$, it can be attached to the amino group by either substitution with alkyl halide or other suitable electrophile, or reductive amination of an aldehyde. When R" is $COR^7$, it can be introduced by condensation of e with $R^7CO-L$ wherein L is a leaving group. In one embodiment, $R^7CO-L$ is an acid (i.e., $R^7CO_2H$) or acid chloride (i.e., $R^7COCl$).

EXAMPLE 3

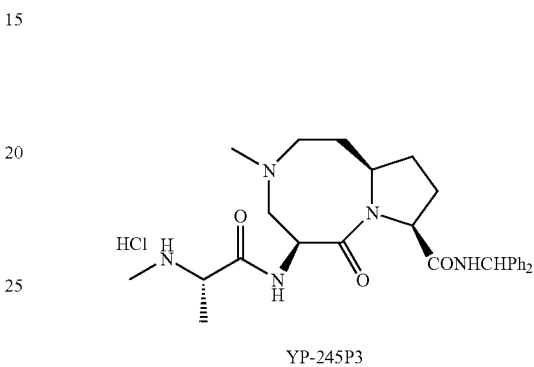

YP-245P3

Analytical data for YP-245P3: $^1H$ NMR (300 MHz, $D_2O$, TMS) δ 7.28-7.20 (m, 10H), 5.97 (s, 1H), 5.25 (br, 1H), 4.51 (br, 1H), 3.91-3.84 (q, J=7.1 Hz, 1H), 3.82-3.70 (m, 1H), 3.58-3.55 (m, 1H), 3.48-3.43 (m, 1H), 3.23-3.19 (t, J=12 Hz, 1H), 2.90 (s, 3H), 2.56 (s, 3H), 2.40-2.36 (m, 1H), 2.13-1.73 (m, 5H), 1.41-1.38 (d, J=7.1 Hz, 3H); HRMS: calcd. m/z for $[M+H]^+$ 492.2975; found 492.2971.

EXAMPLE 4

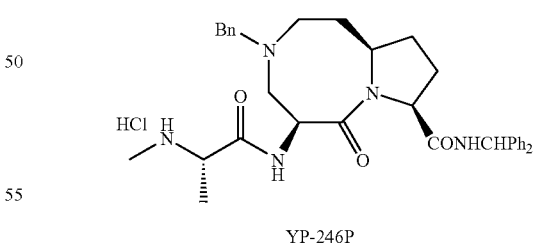

YP-246P

Analytical data for YP-246P: $^1H$ NMR (300 MHz, $D_2O$, TMS) δ 7.33-7.13 (m, 15H), 6.03-6.01 (m, 1H), 5.32-5.30 (m, 1H), 4.64-4.61 (m, 1H), 4.31 (s, 2H), 3.85-3.83 (q, J=7.1 Hz, 1H), 3.69 (m, 1H), 3.59-3.51 (m, 1H), 3.12-3.08 (t, J=11.6 Hz, 1H), 2.55 (s, 3H), 2.40-2.28 (m, 1H), 2.09-2.04 (m, 1H), 1.81-1.66 (m, 4H), 1.37-1.35 (d, J=7.1 Hz, 3H); HRMS: calcd. m/z for [M+H]+ 568.3288; found 568.3284.

EXAMPLE 5

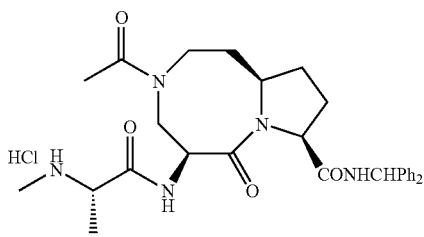

SM-330

Analytical data for SM-330: $^1$H NMR (300 MHz, D$_2$O, TMS) δ 8.88-8.76 (m, 1H), 7.30-7.18 (m, 10H), 5.95-5.93 (d, J=4.7 Hz, 1H), 4.93-4.91 (m, 1H), 4.38-4.26 (m, 1H), 4.24 (m, 1H), 3.90-3.86 (m, 1H), 3.69-3.65 (m, 1H), 3.50-3.38 (m, 2H), 2.58 (s, 3H), 2.23-2.18 (m, 1H), 2.04 (s, 3H), 1.93 (s, 2H), 1.81-1.74 (m, 4H), 1.43-1.41 (d, J=7.0 Hz, 3H); $^{13}$C NMR (75 MHz, D$_2$O) δ 175.3, 173.3, 172.9, 170.2, 141.2, 129.2, 128.1, 127.7, 62.3, 62.1 58.5, 57.8, 57.3, 52.6, 51.8, 32.2, 31.3, 27.5, 21.5, 20.7, 15.5; HRMS: calcd. m/z for [M+H]+ 520.2924; found 520.2924.

EXAMPLE 6

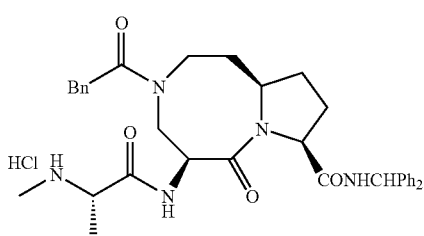

SM-337

Analytical data for SM-337: $^1$H NMR (300 MHz, CD$_3$OD, TMS) δ 7.34-7.27 (m, 15H), 6.18-6.15 (d, J=8.0 Hz, 1H), 4.60-4.57 (m, 1H), 4.28 (m, 1H), 4.12-4.07 (m, 1H), 3.99-3.82 (m, 4H), 3.50-3.40 (m, 1H), 2.67 (s, 3/2 H), 2.66 (s, 3/2 H), 2.34 (m, 1H), 2.07-2.00 (m, 3H), 1.88-1.81 (m, 2H), 1.56-1.52 (d, J=6.8 Hz, 3H); $^{13}$C NMR (75 MHz, CD$_3$OD) δ 174.6, 174.0, 169.6, 169.4, 143.1, 136.4, 130.3, 129.5, 128.6, 128.2, 127.8, 62.7, 58.3, 54.2, 41.6, 33.3, 31.9, 28.2, 16.3.

EXAMPLE 7

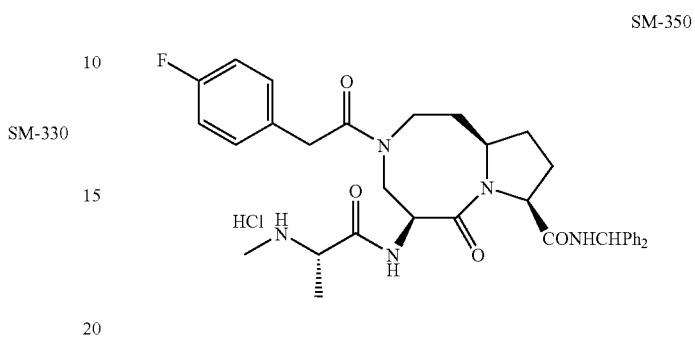

SM-350

Analytical data for SM-350: $^1$H NMR (300 MHz, CD$_3$OD, TMS) δ 8.94-8.92 (d, J=7.9 Hz, 1H), 7.34-7.26 (m, 12H), 7.04-6.98 (m, 2H), 6.18-6.15 (d, J=7.9 Hz, 1H), 4.60-4.57 (m, 1H), 4.31 (br, 1H), 4.02-3.76 (m, 4H), 3.50 (m, 1H), 2.68 (s, 3H), 2.34 (m, 1H), 2.11-1.82 (m, 5H), 1.55-1.53 (d, J=7.0 Hz, 3H); $^{13}$C NMR (75 MHz, CD$_3$OD) δ 173.2, 170.2, 169.7, 164.8, 161.5, 143.1, 132.5, 131.9, 129.6, 128.6, 128.1, 116.2, 62.7, 58.4, 53.9, 40.5, 33.3, 32.3, 31.8, 28.3, 16.3; HRMS: calcd. m/z for [M+Na]+ 636.2962; found 636.2974.

EXAMPLE 8

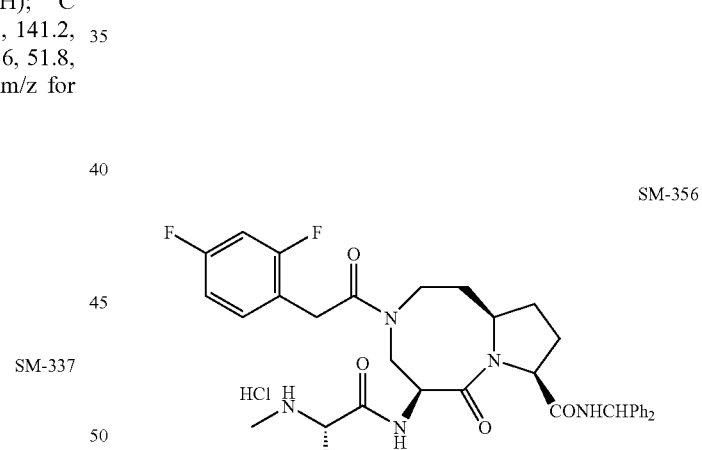

SM-356

Analytical data for SM-356: $^1$H NMR (300 MHz, CD$_3$OD, TMS) δ 8.93-8.91 (d, J=8.0 Hz, 1H), 7.38-7.26 (m, 11H), 6.90-6.86 (m, 2H), 6.18-6.16 (d, J=7.9 Hz, 1H), 5.10-5.00 (m, 1H), 4.61-4.58 (m, 1H), 4.40-4.28 (m, 1H), 4.15-3.91 (m, 4H), 3.36 (m, 2H), 2.69 (s, 2H), 2.67 (s, 1H), 2.42-2.28 (m, 1H), 2.02-1.95 (m, 5H), 1.55-1.53 (d, J=7.0 Hz, 3H); $^{13}$C NMR (75 MHz, CD$_3$OD) δ 173.2, 172.4, 170.2, 169.7, 169.4, 143.2, 134.1, 129.6, 128.4, 128.1, 120.1, 112.0, 104.1, 62.7, 58.4, 53.9, 34.2, 33.3, 32.3, 31.7, 28.3, 16.2; HRMS: calcd. m/z for [M+Na]$^+$ 654.2868; found 654.2866.

EXAMPLE 9

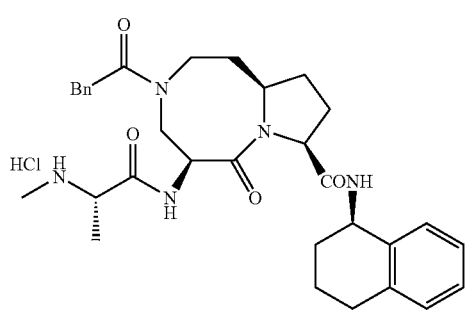

SM-376

Analytical data for SM-376: $^1$H NMR (300 MHz, CD$_3$OD, TMS) δ 8.50-8.43 (m, 1H), 7.46-7.44 (m, 1H), 7.32-7.31 (m, 4H), 7.26-7.24 (m, 1H), 7.15-7.11 (m, 3H), 5.09 (m, 2H), 4.43 (m, 1H), 4.20 (m, 1H), 4.01-3.92 (m, 4H), 3.58-3.42 (m, 1H), 2.83-2.81 (m, 2H), 2.70 (s, 1H), 2.68 (s, 2H), 2.38-2.25 (m, 1H), 2.09-1.82 (m, 8H), 1.27-1.53 (d, J=7.0 Hz, 3H); $^{13}$C NMR (75 MHz, CD$_3$OD) δ 174.1, 173.6, 169.6, 169.3, 138.5, 137.9, 136.5, 130.2, 129.8, 128.0, 127.0, 62.9, 58.3, 54.4, 41.6, 32.1, 31.9, 31.4, 30.2, 28.4, 21.7, 16.4; HRMS: calcd. m/z for [M+Na]$^+$ 582.3056; found 582.3080.

EXAMPLE 10

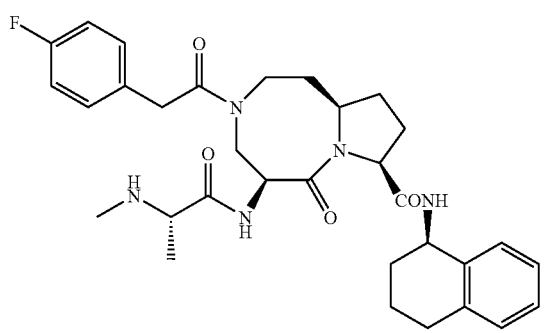

SM-377

Analytical data for SM-377: $^1$H NMR (300 MHz, CD$_3$OD, TMS) δ 8.50-8.40 (m, 1H), 7.47-7.44 (m, 1H), 7.36-7.31 (m, 2H), 7.15-7.01 (m, 5H), 5.09 (m, 2H), 4.43 (m, 1H), 4.38-4.28 (m, 1H), 4.12 (m, 1H), 4.02-3.93 (m, 4H), 2.83-2.81 (m, 2H), 2.70 (s, 3H), 2.38-2.28 (m, 1H), 2.12-1.82 (m, 8H), 1.56-1.53 (d, J=7.0 Hz, 3H); $^{13}$C NMR (75 MHz, CD$_3$OD) δ 173.8, 173.5, 169.7, 169.3, 138.5, 132.5, 131.8, 129.9, 126.9, 116.3, 62.9, 58.3, 57.8, 54.1, 40.6, 33.4, 32.2, 31.7, 30.2, 28.4, 21.7, 16.3; HRMS: calcd. m/z for [M+H]$^+$ 578.3143; found 578.3147.

EXAMPLE 11

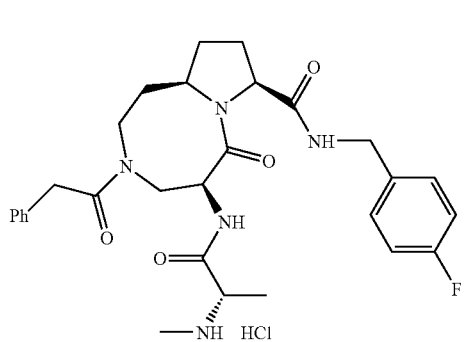

SM-401

Analytical data for SM-401: $^1$H NMR (MeOH-d$_4$, 300 M Hz) δ 7.37 (m, 2H), 7.30 (m, 5H), 7.05 (m, 2H), 4.46 (m, 2H), 4.33 (m, 2H), 3.92-3.81 (m, 6H), 3.54 (m, 1H), 3.32 (m, 1H), 2.74 (s, 3H), 2.34 (m, 1H), 2.16-1.78 (m, 5H), 1.54 (d, J=6.3 Hz, 3H). $^{13}$C NMR (MeOH-d$_4$, 300 M Hz) δ 173.2, 168.8, 168.5, 164.0, 160.8, 135.3, 129.4, 129.2, 128.8, 126.9, 115.3, 115.0, 62.0, 61.2, 57.3, 57.1, 53.2, 53.0, 42.9, 42.3, 40.7, 32.5, 31.3, 27.5, 15.5.

EXAMPLE 12

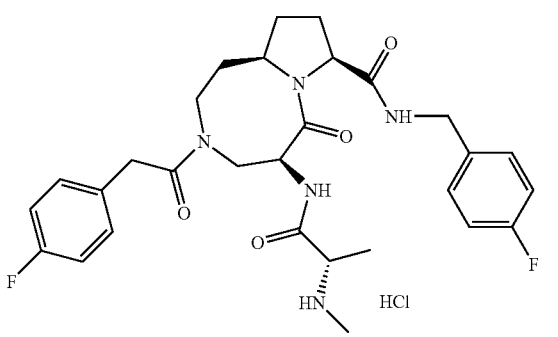

SM-402

Analytical data for SM-402: $^1$H NMR (MeOH-d$_4$, 300 M Hz) δ 8.60 (m, 1H), 7.40 (m, 4H), 7.02 (m, 4H), 4.52-4.43 (m, 2H), 4.35-4.29 (m, 2H), 4.08-3.80 (m, 6H), 3.54 (m, 1H), 3.38 (m, 1H), 2.70 (s, 3H), 2.33 (m, 1H), 2.13-1.82 (m, 5H), 1.54 (d, J=6.9 Hz, 3H). $^{13}$C NMR (MeOH-d$_4$, 300 M Hz) δ 173.1, 172.8, 168.8, 168.5, 164.1, 135.1, 131.5, 131.0, 129.2, 115.3, 115.0, 61.9, 57.3, 52.9, 42.3, 39.6, 32.4, 31.3, 30.9, 27.3, 15.3

EXAMPLE 13

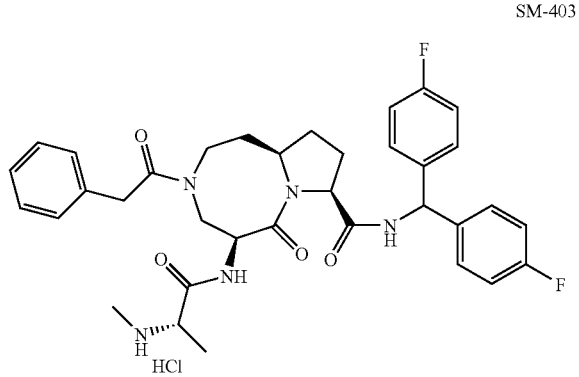

SM-403

Analytical data for SM-403: $^1$H NMR (MeOH-d$_4$, 300 MHz) δ 7.39-7.22 (m, 9H), 7.08-7.02 (m, 4H), 6.15 (d, J=6.0, 1H), 4.97 (m, 1H), 4.54 (m, 1H), 4.30 (m, 1H), 4.02-3.66 (m, 6H), 3.59-3.54 (m, 1H), 2.66 (s, 3H), 2.33 (m, 1H), 2.11-1.80 (m, 5H), 1.53 (d, J=6.6 Hz, 3H). $^{13}$C NMR (MeOH-d$_4$, 300 MHz) δ 173.4, 172.4, 168.8, 168.4, 164.2, 160.9, 138.1, 135.3, 129.8, 129.7, 129.6, 129.5, 129.4, 129.0, 128.7, 128.6, 126.9, 115.6, 115.3, 115.0, 72.6, 61.9, 57.3, 56.2, 53.1, 47.0, 40.6, 32.3, 31.5, 31.1, 27.4, 15.5.

EXAMPLE 14

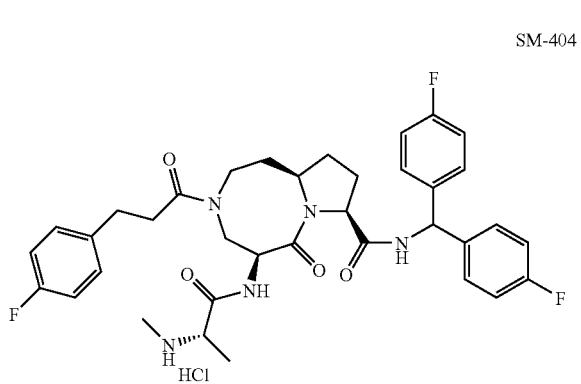

SM-404

Analytical data for SM-404: $^1$H NMR (MeOH-d$_4$, 300 MHz) δ 7.37-7.25 (m, 6H), 7.11-6.91 (m, 6H), 6.15 (d, J=7.5, 1H), 4.83 (m, 1H), 4.54 (m, 1H), 4.30 (m, 1H), 4.02-3.60 (m, 6H), 3.51 (m, 1H), 2.94 (m, 2H), 2.72 (s, 3H), 2.23 (m, 1H), 2.11-1.80 (m, 5H), 1.53 (d, J=6.6 Hz, 3H). $^{13}$C NMR (MeOH-d$_4$, 300 MHz) δ 174.0, 172.4, 168.7, 168.4, 163.7, 160.8, 137.9, 137.4, 130.7, 130.6, 129.9, 129.8, 129.6, 129.5, 115.6, 115.3, 115.1, 115.0, 114.0, 71.5, 67.2, 57.4, 56.0, 55.9, 52.8, 51.7, 35.0, 32.3, 31.5, 31.1, 30.7, 27.4, 15.4.

EXAMPLE 15

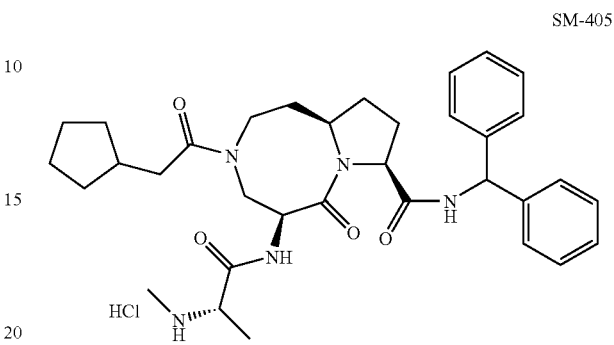

SM-405

Analytical data for SM-405: $^1$H NMR (MeOH-d$_4$, 300 MHz) δ 7.40-7.25 (m, 10H), 6.15 (s, 1H), 4.61-4.55 (m, 1H), 4.28-4.22 (m, 1H), 4.00-3.95 (m, 2H), 3.86-3.81 (m, 1H), 3.68-3.66 (m, 1H), 3.45-3.40 (m, 1H), 2.94-2.92 (m, 1H), 2.72 (s, 3H), 2.68-2.57 (m, 2H), 2.34-2.23 (m, 2H), 2.16-1.79 (m, 7H), 1.66-1.53 (m, 4H), 1.52 (d, J=7.2 Hz, 3H). $^{13}$C NMR (MeOH-d$_4$, 300 MHz) δ 176.1, 172.2, 168.8, 168.3, 142.2, 142.1, 132.2, 132.0, 129.1, 128.7, 128.4, 127.9, 127.8, 127.7, 127.5, 127.2, 61.8, 57.5, 57.3, 53.1, 38.9, 38.7, 37.2, 32.5, 32.2, 31.4, 31.0, 27.4, 24.9, 15.3.

EXAMPLE 16

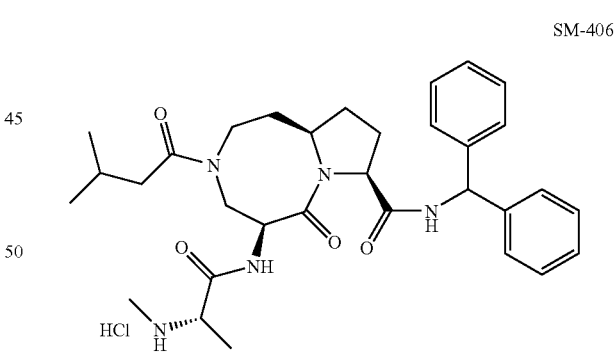

SM-406

Analytical data for SM-406: $^1$H NMR (MeOH-d$_4$, 300 MHz) δ 7.38-7.25 (m, 10H), 6.14 (d, J=7.5 Hz, 1H), 4.62-4.56 (m, 1H), 4.30-4.25 (m, 1H), 4.05-3.96 (m, 2H), 3.87-3.49 (m, 4H), 2.72 (s, 3H), 2.46 (m, 2H), 2.37-2.32 (m, 1H), 2.15-2.00 (m, 5H), 1.84-1.80 (m, 1H), 1.56 (d, J=5.4 Hz, 3H), 1.00 (m, 6H), $^{13}$C NMR (MeOH-d$_4$, 300 MHz) δ 175.7, 172.3, 168.8, 168.3, 142.2, 142.1, 132.2, 132.0, 129.1, 129.0, 128.7, 128.4, 127.8, 127.7, 127.5, 127.2, 61.8, 57.4, 57.3, 53.2, 41.7, 38.6, 37.2, 32.2, 31.4, 31.0, 27.4, 26.3, 22.0, 15.3.

EXAMPLE 17

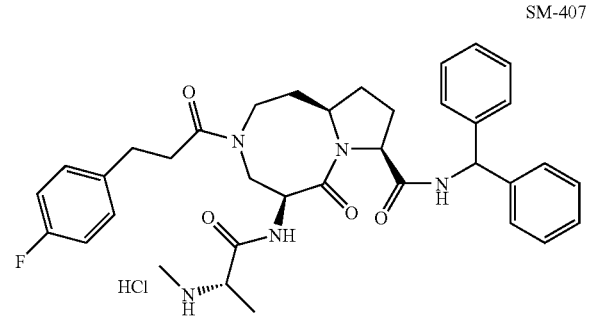

SM-407

Analytical data for SM-407: $^1$H NMR (MeOH-d$_4$, 300 MHz) δ 7.31-7.27 (m, 12H), 6.94 (m, 2H), 6.15 (m, 1H), 4.82-4.70 (m, 1H), 4.53 (m, 1H), 4.09-3.58 (m, 5H), 3.36 (m, 1H), 3.05-2.72 (m, 4H), 2.71 (s, 3H), 2.30 (m, 1H), 2.05-1.81 (m, 5H), 1.56 (m, 3H), $^{13}$C NMR (MeOH-d$_4$, 300 M Hz) δ 173.9, 172.3, 169.4, 168.5, 163.5, 160.2, 142.3, 142.1, 137.5, 132.9, 132.2, 130.8, 130.6, 129.0, 128.6, 127.7, 127.5, 127.3, 115.2, 114.9, 61.9, 57.6, 57.2, 53.1, 52.9, 46.8, 38.2, 35.3, 34.9, 32.4, 31.6, 30.8, 27.5, 15.8.

EXAMPLE 18

SM-408

Analytical data for SM-408: $^1$H NMR (MeOH-d$_4$, 300 M Hz) δ 7.35-7.16 (m, 15H), 6.18 (m, 1H), 4.82-4.70 (m, 1H), 4.53 (m, 1H), 4.09-3.58 (m, 5H), 3.30 (m, 1H), 3.10 (m, 1H), 2.98 (t, J=6.0 Hz, 2H), 2.75 (m, 1H), 2.72 (s, 3H), 2.30 (m, 1H), 2.05-1.81 (m, 5H), 1.56 (m, 3H), $^{13}$C NMR (MeOH-d$_4$, 300 M Hz) δ 174.3, 172.4, 169.0, 168.5, 142.3, 141.8, 132.9, 132.1, 129.1, 128.9, 128.7, 128.5, 127.7, 127.6, 127.3, 126.2, 61.8, 57.4, 57.2, 52.8, 46.6, 34.9, 32.3, 31.7, 30.9, 27.5, 15.4.

EXAMPLE 19

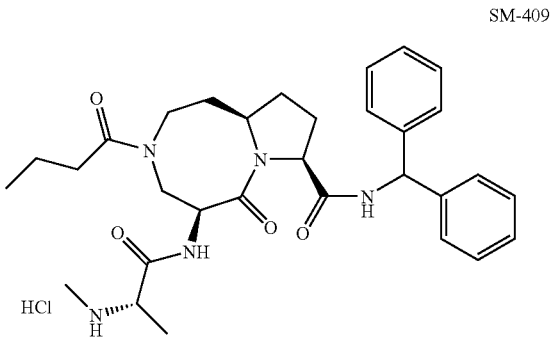

SM-409

Analytical data for SM-409: $^1$H NMR (MeOH-d$_4$, 300 M Hz) δ 7.37-7.26 (m, 10H), 6.16 (s, 1H), 4.60 (m, 1H), 4.26 (m, 1H), 4.06-3.92 (m, 2H), 3.80 (m, 1H), 3.68-3.35 (m, 2H), 2.72 (s, 3H), 2.56 (m, 2H), 2.30 (m, 1H), 2.05-1.81 (m, 5H), 1.64 (q, J=7.5 Hz, 2H), 1.56 (d, J=6.6 Hz, 3H), 0.96 (t, J=7.5 Hz, 3H), $^{13}$C NMR (MeOH-d$_4$, 300 M Hz) δ 175.6, 172.3, 168.7, 168.5, 142.2, 142.1, 132.9, 132.8, 132.2, 132.0, 129.1, 129.0, 128.7, 128.4, 127.7, 127.3, 61.8, 57.4, 57.3, 53.0, 46.9, 35.3, 34.9, 32.4, 31.4, 30.9, 27.3, 18.9, 15.4, 13.3.

EXAMPLE 20

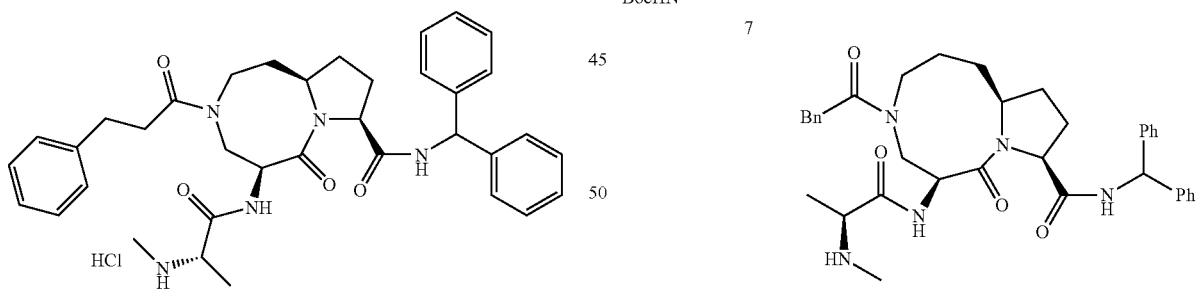

SM-207

Reagents and conditions: i. phenylacetic acid, EDC, HOBt, N,N-diisopropylethylamine, CH2Cl2; ii. 3 N LiOH, 1,4-dioxane, then 1N HCl; iii. aminodiphenylmethane, EDC, HOBt, N,N-diisopropylethylamine, CH2Cl2; iv. 4N HCl in 1,4-dioxane, v. N-Boc-N-methyl alanine, EDC, HOBt, N,N-diisopropylethylamine, CH2Cl2; vi. 4N HCl in 1,4-dioxane, 62% over six steps.

Condensation of 7 with phenylacetic acid followed by hydrolysis of the methyl ester gave an acid which was condensed with aminodiphenylamine yielded the amide. Removal of the Boc protecting group in this amide provided an ammonium salt. Condensation of this salt with N-Boc-N-methyl-alanine followed by removal of the Boc protecting group furnished SH-207.

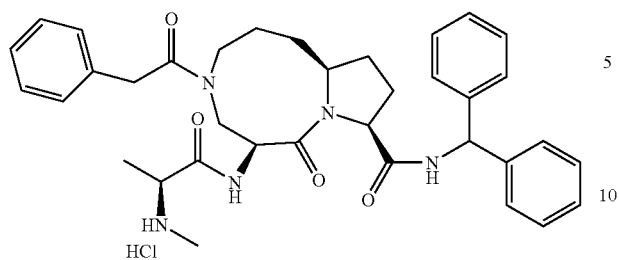

SM-207 · HCl

Analytical data for SM-207: $^1$H NMR (300 MHz, D$_2$O) δ 7.22-6.80 (m, 15H), 5.95 (s, 1H), 4.75 (m, 1H), 4.38 (m, 1H), 4.18-3.45 (m, 5H), 3.42-2.85 (m, 3H), 2.67 (s, 3H), 2.12-0.80 (m, 11H); $^{13}$C NMR (75 MHz, D$_2$O) δ 174.27, 172.09, 170.94, 169.24, 142.01, 141.83, 141.68, 134.86, 129.32, 128.16, 128.99, 127.76, 127.34, 71.92, 61.13, 58.57, 57.31, 49.77, 49.21, 49.05, 41.46, 31.44, 18.06, 15.73, 15.62.

EXAMPLE 21

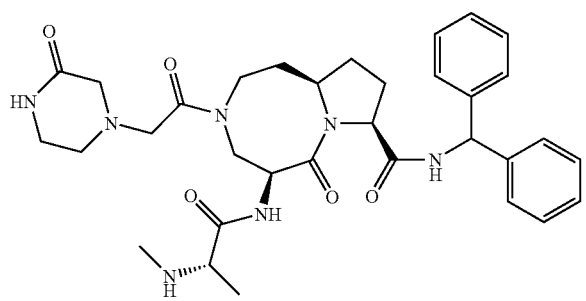

SM-412

Analytical data for SM-412: $^1$H NMR (MeOH-d$_4$, 300 M Hz) δ 8.81 (m, 1H), 7.41-7.26 (m, 10H), 6.06 (m, 1H), 4.56-4.43 (m, 3H), 4.11 (m, 2H), 3.99-3.76 (m, 4H), 3.58-3.47 (m, 4H), 3.32 (m, 1H), 2.72 (m, 3H), 2.34-1.80 (m, 6H), 1.60 (m, 3H), $^{13}$C NMR (MeOH-d$_4$, 300 M Hz) δ 172.1, 169.2, 168.7, 164.1, 163.6, 160.2, 142.3, 142.0, 128.7, 128.2, 127.9, 127.7, 127.5, 127.3, 116.3, 62.2, 58.0, 57.8, 53.5, 50.3, 46.4, 37.3, 32.0, 30.8, 27.9, 15.2.

EXAMPLE 22

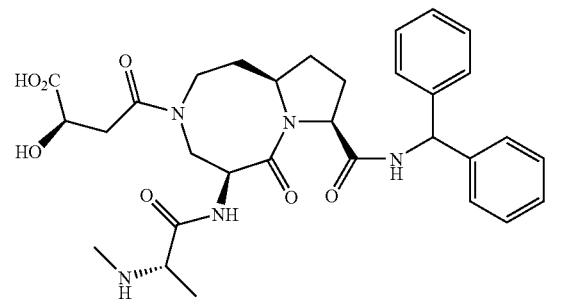

SM-413

Analytical data for SM-413: $^1$H NMR (MeOH-d$_4$, 300 M Hz) δ 9.00 (d, J=8.1 Hz, 1H), 7.41-7.26 (m, 10H), 6.17 (m, 1H), 4.62 (m, 2H), 4.32 (m, 1H), 4.00 (m, 2H), 3.75 (m, 3H), 3.47 (m, 1H), 3.20 (m, 1H), 2.92 (m, 1H), 2.72 (2s, 3H), 2.30 (m, 1H), 2.07-1.80 (m, 5H), 1.54 (d, J=7.2 Hz, 3H), $^{13}$C NMR (MeOH-d$_4$, 300 M Hz) δ 174.8, 172.4, 171.7, 168.8, 168.5, 142.2, 142.0, 128.7, 128.4, 127.8, 127.7, 127.5, 127.3, 68.2, 61.8, 57.3, 51.7, 46.9, 37.7, 32.2, 30.8, 27.4, 15.2.

EXAMPLE 23

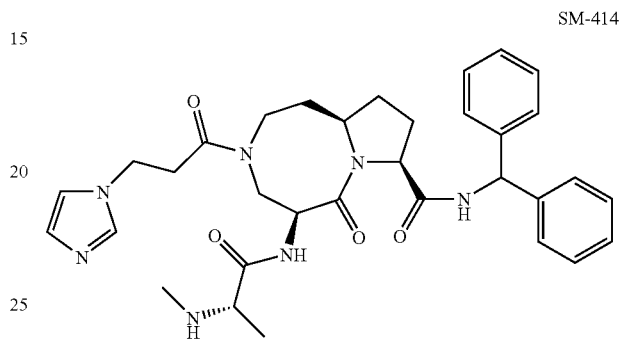

SM-414

Analytical data for SM-414: $^1$H NMR (MeOH-d$_4$, 300 M Hz) δ 8.80 (m, 1H), 7.41-7.26 (m, 12H), 6.09 (m, 1H), 5.12 (m, 1H), 4.56 (m, 2H), 4.32 (m, 1H), 4.18 (m, 1H), 4.03 (m, 2H), 3.75 (m, 2H), 3.46 (m, 1H), 3.16 (m, 1H), 2.72 (s, 3H), 2.30-1.80 (m, 6H), 1.54 (m, 3H), $^{13}$C NMR (MeOH-d$_4$, 300 M Hz) δ 172.2, 171.4, 170.4, 169.1, 168.7, 142.3, 142.2, 136.0, 128.7, 128.4, 128.1, 127.9, 127.6, 127.5, 127.1, 122.4, 119.6, 62.1, 57.6, 57.3, 46.4, 45.4, 33.4, 32.3, 30.8, 27.7, 15.2.

EXAMPLE 24

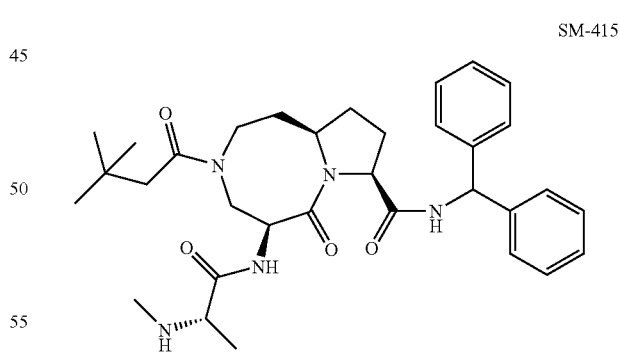

SM-415

Analytical data for SM-415: $^1$H NMR (MeOH-d$_4$, 300 M Hz) δ 8.97 (d, J=8.4 Hz, 1H), 7.38-7.25 (m, 10H), 6.16 (m, 1H), 4.80 (m, 1H), 4.58 (m, 1H), 4.25 (m, 1H), 3.96 (m, 3H), 3.47 (m, 1H), 3.20 (m, 1H), 2.72 (s, 3H), 2.62 (m, 1H), 2.49 (m, 1H), 2.34 (m, 1H), 2.15-1.87 (m, 5H), 1.56 (m, 3H), 1.08 (s, 9H), $^{13}$C NMR (MeOH-d$_4$, 300 M Hz) δ 174.2, 172.5, 169.0, 168.4, 142.1, 142.0, 128.7, 128.5, 127.8, 127.7, 127.5, 127.3, 61.7, 57.4, 57.3, 53.1, 51.9, 46.7, 44.6, 32.5, 31.5, 31.2, 30.8, 29.4, 27.2, 15.3.

EXAMPLE 25

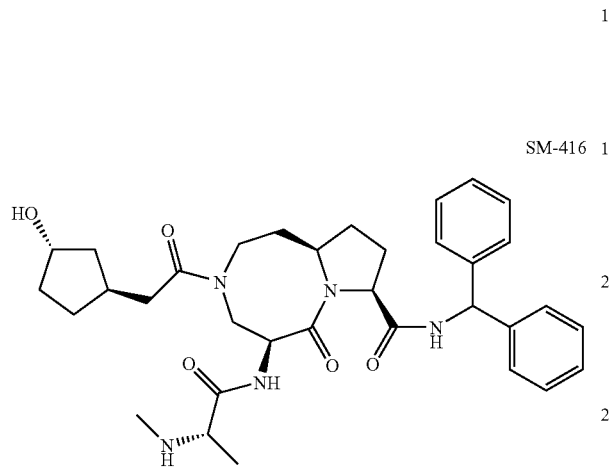

SM-416

Analytical data for SM-416: $^1$H NMR (MeOH-d$_4$, 300 M Hz) δ 8.95 (d, J=8.1 Hz, 1H), 7.38-7.25 (m, 10H), 6.16 (m, 1H), 4.80 (m, 1H), 4.56 (m, 1H), 4.25 (m, 2H), 3.92 (m, 3H), 3.47 (m, 1H), 2.72 (s, 3H), 2.60 (m, 3H), 2.34 (m, 1H), 2.12-1.81 (m, 8H), 1.56 (m, 4H), 1.47 (m, 1H), 1.30 (m, 1H), $^{13}$C NMR (MeOH-d$_4$, 300 M Hz) δ 174.6, 172.4, 169.5, 168.4, 142.2, 142.0, 128.7, 128.4, 127.8, 127.7, 127.5, 127.3, 73.0, 61.7, 57.3, 57.2, 53.1, 51.9, 46.6, 42.0, 39.4, 34.4, 32.5, 31.2, 30.8, 27.2, 15.2.

EXAMPLE 26

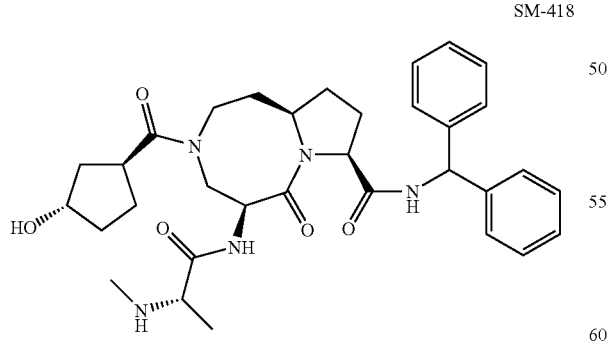

SM-418

Analytical data for SM-418: $^1$H NMR (MeOH-d$_4$, 300 M Hz) δ 7.37-7.25 (m, 10H), 6.16 (m, 1H), 4.89 (m, 1H), 4.58 (m, 1H), 4.40 (m, 1H), 4.26 (m, 1H), 4.03-3.83 (m, 3H), 3.66-3.48 (m, 3H), H), 2.70 (m, 3H), 2.33 (m, 1H), 2.08-1.75 (m, 10H), 1.54 (m, 3H), $^{13}$C NMR (MeOH-d$_4$, 300 M Hz) δ 177.6, 172.4, 169.2, 168.6, 142.2, 142.0, 128.7, 128.5, 128.4, 127.8, 127.7, 127.6, 127.5, 127.3, 73.4, 61.7, 57.3, 57.1, 53.0, 51.9, 46.9, 39.4, 38.9, 34.7, 32.7, 31.3, 30.8, 28.0, 27.3, 15.2.

EXAMPLE 27

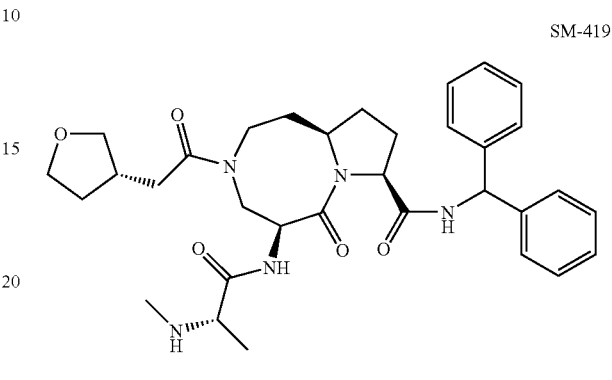

SM-419

Analytical data for SM-419: $^1$H NMR (MeOH-d$_4$, 300 M Hz) δ 7.37-7.25 (m, 10H), 6.16 (m, 1H), 4.89 (m, 1H), 4.58 (m, 2H), 4.26 (m, 1H), 4.03-3.71 (m, 5H), 3.55-3.37 (m, 2H), 2.70 (m, 3H), 2.67 (m, 2H), 2.33 (m, 1H), 2.08-1.75 (m, 6H), 1.54 (m, 3H), $^{13}$C NMR (MeOH-d$_4$, 300 M Hz) δ 173.5, 172.2, 169.2, 168.6, 142.2, 141.9, 128.8, 128.7, 128.5, 128.4, 128.2, 127.8, 127.7, 127.6, 127.5, 127.3, 127.2, 73.1, 67.5, 61.8, 57.3, 46.6, 37.1, 35.9, 32.5, 32.1, 31.4, 30.8, 27.4, 15.2.

EXAMPLE 28

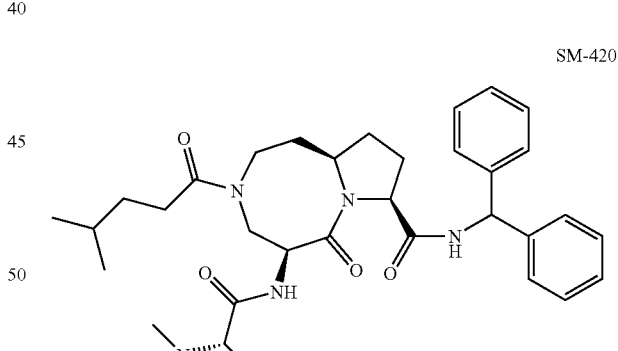

SM-420

Analytical data for SM-420: $^1$H NMR (MeOH-d$_4$, 300 M Hz) δ 7.38-7.25 (m, 10H), 6.16 (s, 1H), 4.87 (m, 1H), 4.58 (m, 1H), 4.24 (m, 1H), 3.98 (m, 2H), 3.75 (m, 1H), 3.42 (m, 1H), 3.24 (m, 1H), 2.68 (s, 3H), 2.49 (m, 2H), 2.37-2.32 (m, 1H), 2.15-2.00 (m, 5H), 1.84-1.80 (m, 1H), 1.56 (m, 6H), 1.00 (2d, J=6.0 Hz, 6H), $^{13}$C NMR (MeOH-d$_4$, 300 M Hz) δ 175.4, 172.4, 168.9, 168.6, 142.2, 142.0, 128.7, 128.5, 127.8, 127.7, 127.5, 127.3, 61.8, 57.3, 53.0, 52.0, 46.6, 34.4, 32.5, 31.5, 30.9, 28.0, 27.3, 22.0, 21.9, 15.3.

EXAMPLE 29

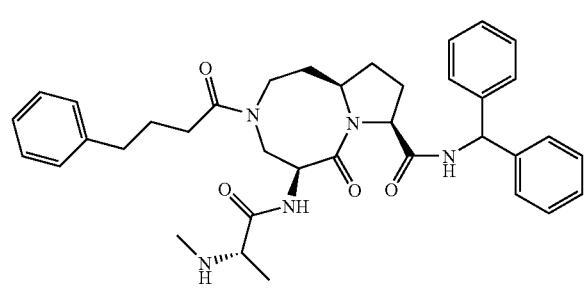

SM-421

Analytical data for SM-421: $^1$H NMR (MeOH-d$_4$, 300 M Hz) δ 8.95 (m, 1H), 7.38-7.14 (m, 15H), 6.17 (m, 1H), 4.85 (m, 1H), 4.56 (m, 1H), 4.23 (m, 1H), 4.04-3.85 (m, 2H), 3.73 (m, 1H), 3.46 (m, 1H), 3.20 (m, 1H), 2.70 (2s, 3H), 2.62 (t, J=7.8 Hz, 2H), 2.45 (m, 2H), 2.30 (m, 1H), 2.05-1.81 (m, 7H), 1.54 (d, J=7.2 Hz, 3H), $^{13}$C NMR (MeOH-d$_4$, 300 M Hz) δ 174.8, 172.3, 169.0, 168.6, 142.2, 142.1, 141.9, 128.7, 128.5, 128.4, 127.8, 127.5, 127.3, 126.0, 61.8, 57.3, 52.8, 52.0, 46.6, 35.2, 32.9, 32.5, 31.8, 31.4, 30.8, 27.2, 15.3.

EXAMPLE 30

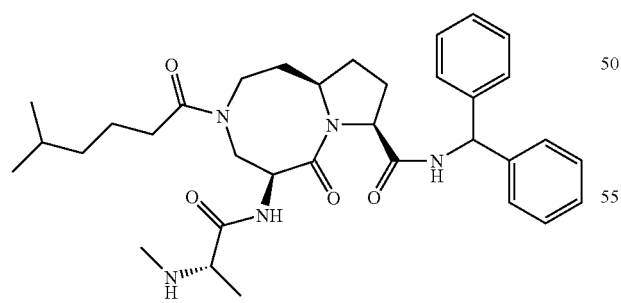

SM-422

Analytical data for SM-422: $^1$H NMR (MeOH-d$_4$, 300 M Hz) δ 7.38-7.25 (m, 10H), 6.18 (s, 1H), 4.87 (m, 1H), 4.57 (m, 1H), 4.22 (m, 1H), 3.98 (m, 2H), 3.76 (m, 1H), 3.42 (m, 1H), 3.24 (m, 1H), 2.70 (2s, 3H), 2.49 (m, 2H), 2.37-2.32 (m, 1H), 2.15-2.00 (m, 4H), 1.78 (m, 1H), 1.68-1.58 (m, 3H), 1.55 (2d, J=7.2 Hz, 3H), 1.27-1.19 (m, 2H), 0.95 (m, 6H), $^{13}$C NMR (MeOH-d$_4$, 300 M Hz) δ 175.3, 172.4, 169.0, 168.6, 142.2, 142.1, 128.7, 128.5, 127.8, 127.7, 127.5, 127.3, 61.8, 57.4, 57.3, 52.9, 51.9, 46.6, 38.7, 32.9, 32.5, 31.3, 30.8, 28.2, 27.3, 23.5, 22.0, 21.9, 15.3.

EXAMPLE 31

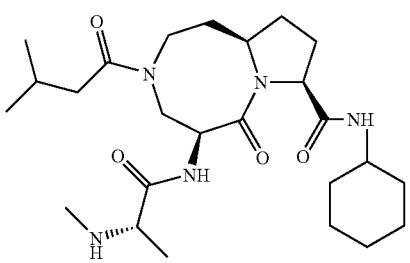

SM-423

Analytical data for SM-423: $^1$H NMR (MeOH-d$_4$, 300 M Hz) δ 4.84 (m, 1H), 4.42 (m, 1H), 4.30 (m, 1H), 3.95 (m, 3H), 3.42 (m, 1H), 3.24 (m, 1H), 2.71 (s, 3H), 2.50 (d, J=7.2 Hz, 2H), 2.34 (m, 1H), 2.15-2.00 (m, 10H), 1.65 (m, 1H), 1.55 (2d, J=7.2 Hz, 3H), 1.16 (m, 6H), 1.00 (m, 6H), $^{13}$C NMR (MeOH-d$_4$, 300 M Hz) δ 174.7, 172.2, 169.1, 168.6, 61.7, 57.3, 57.2, 56.6, 53.2, 50.3, 46.7, 41.8, 32.7, 32.6, 31.3, 30.8, 27.4, 27.2, 26.0, 25.7, 25.1, 22.0, 21.8, 15.2.

EXAMPLE 32

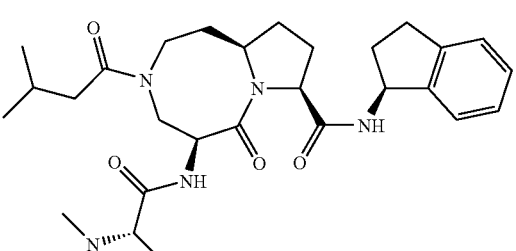

SM-425

Analytical data for SM-425: $^1$H NMR (MeOH-d$_4$, 300 M Hz) δ 7.25-7.18 (m, 4H), 5.36 (t, J=7.5 Hz, 1H), 4.89 (m, 1H), 4.47 (m, 1H), 4.30 (m, 1H), 3.90 (m, 3H), 3.40 (m, 1H), 3.00 (m, 2H), 2.71 (s, 3H), 2.55-2.41 (m, 3H), 2.38 (m, 2H), 2.15-2.00 (m, 6H), 1.81 (m, 1H), 1.54 (m, 3H), 1.00 (m, 6H), $^{13}$C NMR (MeOH-d$_4$, 300 M Hz) δ 174.7, 173.1, 169.1, 168.7, 143.6, 143.4, 128.0, 126.7, 124.7, 124.0, 61.8, 57.3, 56.9, 54.9, 53.1, 51.8, 46.8, 42.1, 41.5, 33.3, 32.7, 31.2, 30.8, 30.0, 27.6, 26.1, 25.9, 22.2, 21.9, 15.2.

EXAMPLE 33

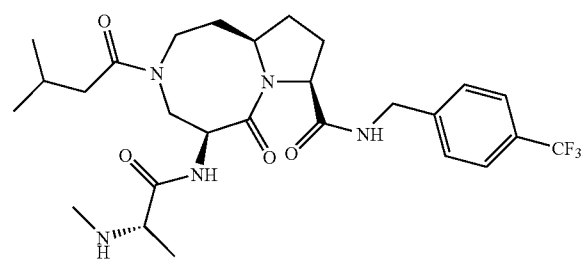

SM-426

Analytical data for SM-426: $^1$H NMR (MeOH-$d_4$, 300 MHz) δ 7.64-7.55 (m, 4H), 4.65 (d, J=16.2 Hz, 1H), 4.55 (m, 1H), 4.39 (d, J=16.2 Hz, 1H), 4.22 (m, 1H), 3.98 (m, 2H), 3.76 (m, 1H), 3.42 (m, 1H), 2.70 (s, 3H), 2.47 (m, 2H), 2.37-2.32 (m, 1H), 2.15-2.00 (m, 6H), 1.83 (m, 1H), 1.54 (m, 3H), 0.95 (m, 6H), $^{13}$C NMR (MeOH-$d_4$, 300 MHz) δ 174.7, 173.5, 169.5, 168.7, 143.6, 143.4, 127.8, 127.5, 125.4, 125.3, 123.0, 61.8, 57.4, 57.2, 56.6, 52.9, 51.8, 46.7, 42.4, 42.1, 41.5, 32.5, 31.3, 30.8, 27.4, 26.2, 23.5, 22.0, 21.9, 15.3.

EXAMPLE 34

SM-427

Analytical data for SM-427: $^1$H NMR (MeOH-$d_4$, 300 MHz) δ 7.45 (m, 1H), 7.20-7.10 (m, 3H), 5.07 (m, 1H), 4.88 (m, 1H), 4.43 (m, 1H), 4.22 (m, 1H), 3.98 (m, 3H), 3.48 (m, 1H), 2.89 (m, 2H), 2.75 (s, 3H), 2.55 (d, J=6.6 Hz, 2H), 2.44 (m, 1H), 2.30-1.78 (m, 11H), 1.55 (m, 3H), 1.00 (m, 6H), $^{13}$C NMR (MeOH-$d_4$, 300 MHz) δ 174.7, 172.7, 169.5, 168.5, 137.6, 136.9, 128.8, 127.1, 126.0, 61.9, 57.3, 56.7, 53.2, 51.9, 46.7, 42.1, 41.5, 32.6, 31.2, 30.8, 29.3, 27.4, 26.1, 22.2, 21.9, 20.8, 15.2.

EXAMPLE 35

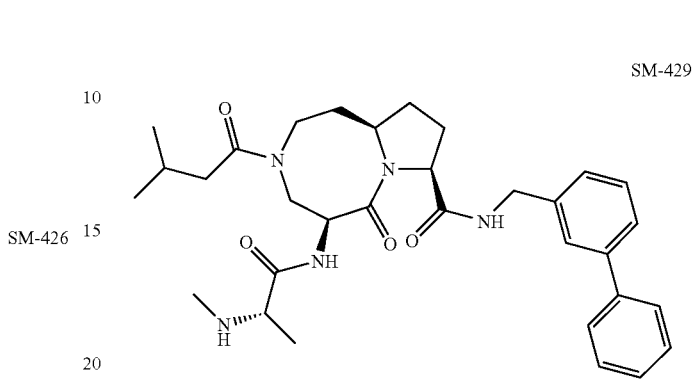

SM-429

Analytical data for SM-429: $^1$H NMR (MeOH-$d_4$, 300 MHz) δ 7.64 (m, 3H), 7.53-7.32 (m, 6H), 4.87 (m, 1H), 4.55-4.40 (m, 3H), 4.23 (m, 1H), 3.98 (m, 2H), 3.82 (m, 1H), 3.38 (m, 1H), 2.71 (s, 3H), 2.46 (d, J=7.2 Hz, 2H), 2.33 (m, 1H), 2.15-1.78 (m, 7H), 1.53 (2d, J=6.9 Hz, 3H), 0.98 (m, 6H), $^{13}$C NMR (MeOH-$d_4$, 300 MHz) δ 174.8, 173.2, 169.6, 168.7, 141.7, 141.2, 139.6, 129.2, 128.9, 127.5, 127.1, 126.1, 125.9, 61.8, 57.2, 56.5, 53.0, 51.8, 46.7, 43.2, 42.1, 41.5, 35.0, 32.6, 31.2, 30.8, 27.3, 26.0, 22.2, 21.9, 15.3.

EXAMPLE 36

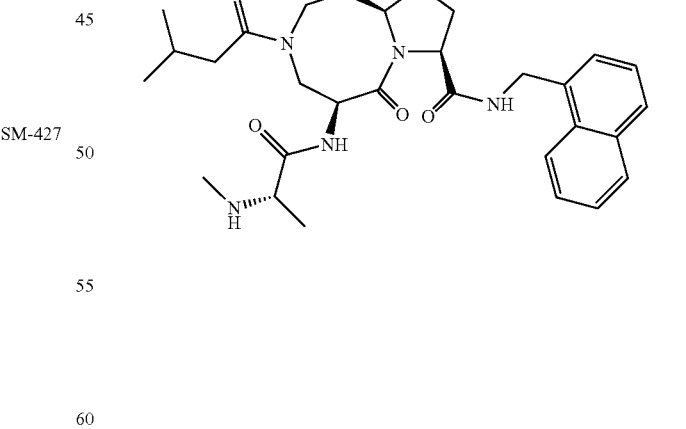

SM-430

Analytical data for SM-430: $^1$H NMR (MeOH-$d_4$, 300 MHz) δ 8.05 (d, J=7.8 Hz, 1H), 7.88 (m, 1H), 7.81 (d, J=8.1 Hz, 1H), 7.57-7.43 (m, 4H), 4.87-4.80 (m, 3H), 4.49 (m, 1H), 4.23 (m, 1H), 3.98 (m, 2H), 3.85 (m, 1H), 3.43 (m, 1H), 2.71 (s, 3H), 2.50 (d, J=6.9 Hz, 2H), 2.33 (m, 1H), 2.15-1.78 (m, 7H), 1.53 (2d, J=7.2 Hz, 3H), 0.99 (m, 6H), $^{13}$C NMR (MeOH-$d_4$, 300 MHz) δ 174.7, 173.0, 169.3, 168.7, 134.3, 133.9, 131.7, 128.8, 128.2, 126.4, 125.8, 125.5, 123.4, 61.8, 57.3, 56.7, 53.1, 51.8, 46.7, 42.1, 41.4, 41.3, 35.0, 32.6, 31.1, 30.8, 27.3, 26.2, 22.2, 21.9, 15.2.

EXAMPLE 37

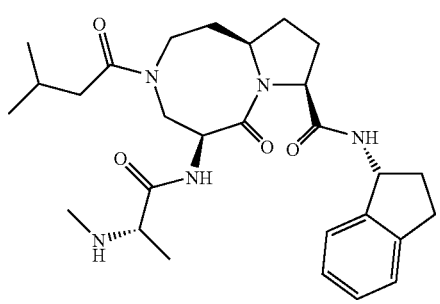

SM-431

Analytical data for SM-431: $^1$H NMR (MeOH-d$_4$, 300 M Hz) δ 7.45 (m, 1H), 7.25-7.17 (m, 3H), 5.40 (t, J=7.8 Hz, 1H), 4.88 (m, 1H), 4.46 (m, 1H), 4.25 (m, 1H), 3.98 (m, 3H), 3.40 (m, 1H), 3.00 (m, 2H), 2.71 (s, 3H), 2.55 (m, 2H), 2.44 (m, 1H), 2.34 (m, 2H), 2.15-2.00 (m, 6H), 1.81 (m, 1H), 1.53 (m, 3H), 1.00 (m, 6H), $^{13}$C NMR (MeOH-d$_4$, 300 M Hz) δ 174.7, 173.1, 169.5, 168.6, 143.6, 143.3, 127.8, 126.5, 124.5, 61.9, 57.3, 56.6, 54.8, 53.2, 51.8, 46.7, 42.1, 41.5, 35.1, 33.4, 32.6, 31.2, 30.8, 30.0, 27.4, 26.1, 22.2, 21.9, 15.2.

EXAMPLE 38

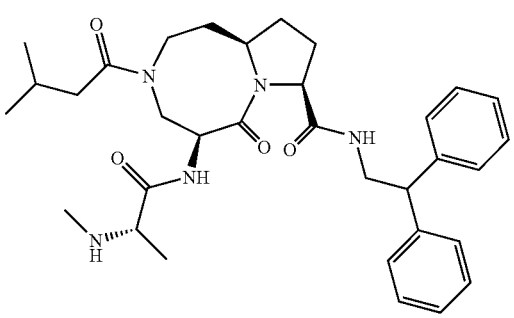

SM-432

Analytical data for SM-432: $^1$H NMR (MeOH-d$_4$, 300 M Hz) δ 7.38-7.25 (m, 10H), 4.80 (m, 1H), 4.32 (m, 2H), 4.18 (m, 1H), 3.98 (m, 2H), 3.87 (m, 1H), 3.63 (m, 1H), 3.49 (m, 1H), 2.70 (s, 3H), 2.50 (d, J=7.2 Hz, 2H), 2.32 (m, 1H), 2.15-1.74 (m, 7H), 1.56 (m, 3H), 1.00 (m, 6H), $^{13}$C NMR (MeOH-d$_4$, 300 M Hz) δ 174.7, 173.0, 169.1, 168.6, 142.8, 128.6, 128.4, 128.1, 126.7, 61.8, 57.2, 56.7, 53.1, 50.9, 46.7, 44.0, 42.0, 41.5, 32.6, 30.8, 27.1, 26.1, 22.2, 21.9, 15.2.

EXAMPLE 39

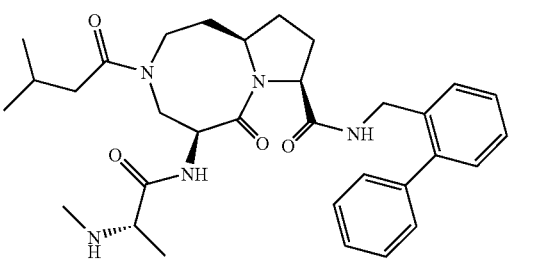

SM-433

Analytical data for SM-433: $^1$H NMR (MeOH-d$_4$, 300 M Hz) δ 7.54-7.22 (m, 9H), 4.86 (m, 1H), 4.48 (m, 1H), 4.4-4.19 (m, 3H), 4.09-3.84 (m, 3H), 3.40 (m, 1H), 2.71 (s, 3H), 2.49 (d, J=6.6 Hz, 2H), 2.33-1.74 (m, 8H), 1.53 (2d, J=6.9 Hz, 3H), 0.98 (m, 6H), $^{13}$C NMR (MeOH-d$_4$, 300 M Hz) δ 174.7, 173.1, 169.3, 168.7, 141.9, 141.2, 135.6, 130.0, 129.2, 128.3, 128.1, 127.8, 127.3, 61.8, 57.3, 56.9, 53.2, 51.8, 46.7, 42.0, 41.5, 41.3, 35.0, 32.6, 31.2, 30.8, 27.3, 26.0, 22.2, 21.9, 15.2.

EXAMPLE 40

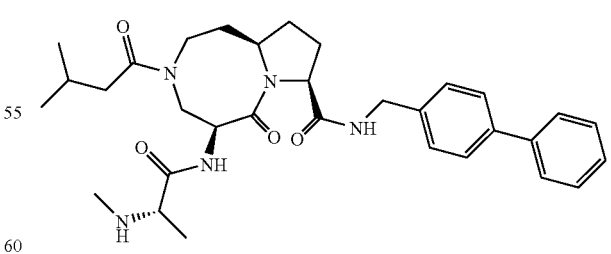

SM-434

Analytical data for SM-434: $^1$H NMR (MeOH-d$_4$, 300 M Hz) δ 7.60 (m, 4H), 7.38 (m, 4H), 7.30 (m, 1H), 4.86 (m, 1H), 4.57-4.36 (m, 3H), 4.22 (m, 1H), 4.04-3.89 (m, 3H), 3.42 (m, 1H), 2.71 (s, 3H), 2.49 (d, J=6.6 Hz, 2H), 2.35-1.79 (m, 8H), 1.53 (2d, J=6.9 Hz, 3H), 0.98 (m, 6H), $^{13}$C NMR (MeOH-d$_4$, 300 M Hz) δ 174.7, 173.2, 169.2, 168.7, 141.1, 140.3, 138.0, 128.9, 128.0, 127.3, 127.1, 126.9, 61.8, 57.3, 56.9, 53.1, 51.8, 46.7, 42.8, 42.1, 41.5, 35.2, 32.6, 31.2, 30.8, 27.4, 26.0, 22.2, 21.9, 15.2.

EXAMPLE 41

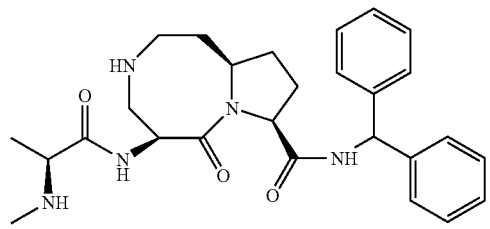

SM-227

Analytical data for SM-227: $^1$H NMR (300 MHz, D$_2$O) δ 7.34-7.12 (m, 10H), 5.92 (brs, 1H), 5.23 (dd, J=12.06, 5.34 Hz, 1H), 4.65 (m, 1H), 4.50 (m, 1H), 3.88 (m, 1H), 3.52 (m, 1H), 3.45 (m, 1H), 3.31 (m, 1H), 3.13 (m, 1H), 2.58 (s, 3H), 2.36 (m, 1H), 2.20-1.72 (m, 5H), 1.41 (d, J=7.05 Hz, 3H); $^{13}$C NMR (75 MHz, D$_2$O) δ 173.93, 170.10, 168.28, 140.81, 140.63, 129.37, 128.33, 128.24, 127.53, 61.31, 59.11, 58.52, 57.15, 48.68, 47.50, 46.10, 31.82, 31.26, 30.94, 27.13, 15.46.

Example 42

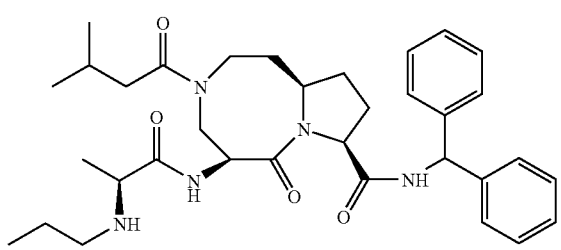

SM-211

Analytical data for SM-211: $^1$H NMR (300 MHz, D$_2$O) δ 7.23-7.02 (m, 10H), 5.85 (s, 1H), 4.70 (m, 1H), 4.32 (m, 1H), 4.01 (m, 1H), 3.85 (m, 1H), 3.65-3.20 (m, 4H), 2.90-2.70 (m, 2H), 2.27-2.03 (m, 3H), 2.01-1.43 (m, 8H), 1.36 (d, J=6.90 Hz, 3H), 0.78 (t, J=7.3 Hz, 3H), 0.76-0.70 (m, 6H); $^{13}$C NMR (75 MHz, D$_2$O) δ 176.89, 173.57, 170.10, 170.06, 142.14, 142.08, 129.86, 129.77, 128.72, 128.62, 128.35, 128.21, 62.77, 58.54, 56.95, 49.58, 49.29, 48.82, 48.72, 48.43, 48.14, 43.00, 31.92, 26.74, 22.83, 22.64, 20.33, 16.55, 11.20.

EXAMPLE 43

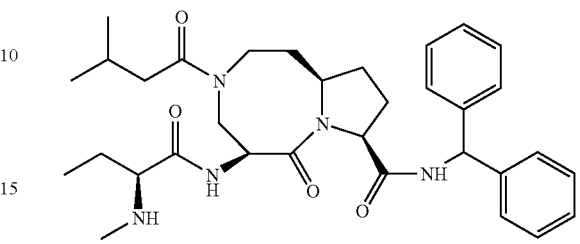

SM-212

Analytical data for SM-212: $^1$H NMR (300 MHz, D$_2$O) δ 7.37-7.16 (m, 10H), 6.12 (m, 1H), 4.82 (m, 1H), 4.56 (m, 1H), 4.20 (m, 1H), 4.08 (m, 1H), 3.96 (m, 1H), 3.87 (m, 1H), 3.42-3.25 (m, 2H), 2.52-1.70 (m, 14H), 1.52 (t, J=7.2 Hz, 3H), 0.98 (t, J=7.5 Hz, 6H); $^{13}$C NMR (75 MHz, D$_2$O) δ 176.45, 173.01, 169.39, 168.33, 141.38, 141.23, 129.27, 129.16, 128.10, 127.73, 127.55, 127.52, 62.77, 62.11, 57.92, 57.01, 52.49, 51.96, 47.58, 46.71, 41.39, 31.82, 27.26, 26.29, 23.69, 22.14, 8.50.

EXAMPLE 44

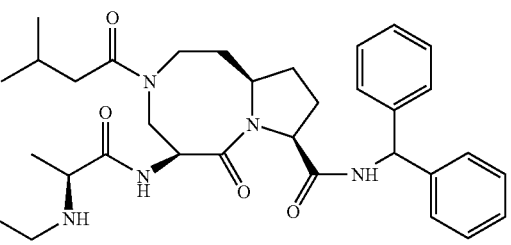

SM-213

Analytical data for SM-213: $^1$H NMR (300 MHz, D$_2$O) δ 7.38-7.20 (m, 10H), 6.05 (s, 1H), 4.89 (m, 1H), 4.62 (m, 1H), 4.53 (m, 1H), 4.36-4.10 (m, 2H), 3.95-3.40 (m, 4H), 3.28-3.10 (m, 1H), 2.50-1.75 (m, 9H), 1.59 (d, J=7.2 Hz, 3H), 1.01-1.85 (m, 6H); $^{13}$C NMR (75 MHz, D$_2$O) δ 177.09, 173.01, 169.46, 167.43, 141.52, 141.39, 129.24, 129.16, 128.11, 127.96, 127.78, 127.64, 61.80, 58.06, 57.17, 56.51, 51.72, 49.30, 48.73, 48.25, 47.87, 41.42, 27.32, 26.29, 22.25, 22.15, 21.88, 15.92.
EXAMPLE 45
SM-209
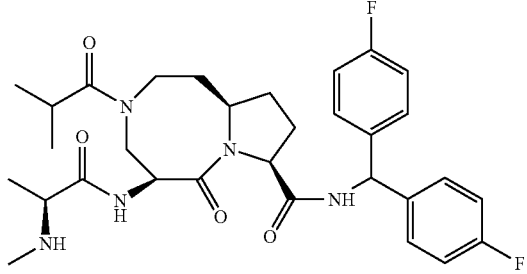
Analytical data for SM-209: $^1$H NMR (300 MHz, D$_2$O) δ 7.22-7.05 (m, 4H), 6.95-6.77 (m, 4H), 5.90 (s, 1H), 4.90 (m, 1H), 4.45 (m, 1H), 4.13 (m, 1H), 3.97 (m, 1H), 3.85-3.60 (m, 1H), 3.50-3.10 (m, 3H), 2.80 (m, 1H), 2.65 (s, 3H), 2.30-1.60 (m, 6H), 1.46 (d, J=7.2 Hz, 3H), 1.12-0.85 (m, 6H); $^{13}$C NMR (75 MHz, D$_2$O) δ 180.27, 172.52, 169.36, 160.48, 137.37, 137.19, 129.55, 129.45, 115.81, 115.53, 61.98, 57.32, 56.43, 51.92, 49.98, 46.81, 35.07, 32.70, 31.30, 30.82, 27.44, 19.18, 18.76, 15.53.
EXAMPLE 46
SM-210
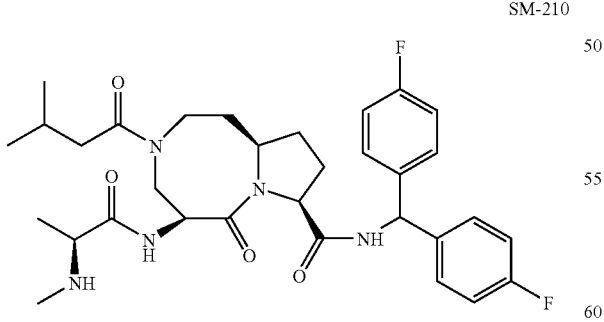
Analytical data for SM-210: $^1$H NMR (300 MHz, D$_2$O) δ 7.22-7.03 (m, 4H), 6.95-6.80 (m, 4H), 5.90 (s, 1H), 4.82 (m, 1H), 4.35 (m, 1H), 4.12 (m, 1H), 3.89 (m, 1H), 3.82-3.15 (m, 4H), 2.60 (s, 3H), 2.30-1.50 (m, 9H), 1.42 (d, J=7.2 Hz, 3H), 0.82-0.65 (m, 6H); $^{13}$C NMR (75 MHz, D$_2$O) δ 176.09, 172.70, 169.50, 160.53, 137.27, 137.14, 129.49, 129.35, 115.92, 115.84, 115.80, 115.62, 62.10, 61.80, 58.07, 56.54, 52.26, 46.59, 42.28, 41.38, 32.40, 31.35, 27.43, 25.98, 22.16, 15.59.
EXAMPLE 47
SM-230
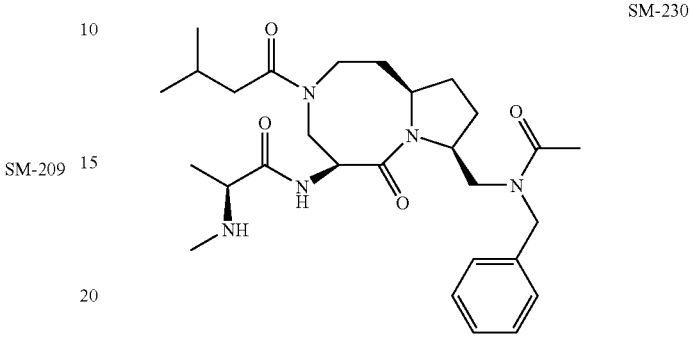
Analytical data for SM-230: $^1$H NMR (300 MHz, D$_2$O) δ 7.32-7.16 (m, 3H), 7.12-7.05 (m, 2H), 5.02 (m, 1H), 4.32-4.12 (m, 3H), 4.02-3.20 (m, 5H), 3.10 (m, 1H), 2.52 (s, 3H), 2.28-1.52 (m, 12H), 1.42-1.39 (m, 3H), 0.82-0.60 (m, 6H).
EXAMPLE 48
SM-428
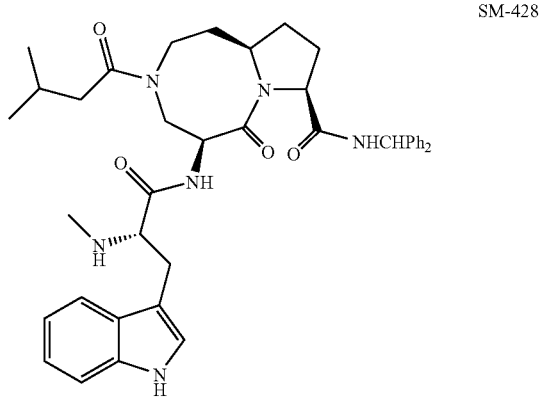
EXAMPLE 49
SM-435
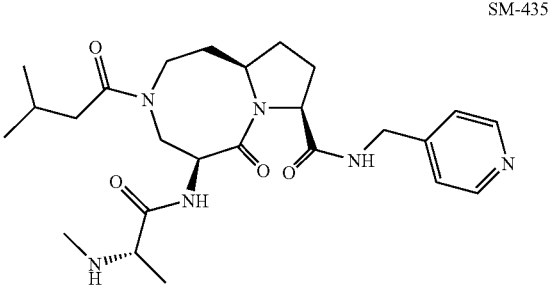

EXAMPLE 50

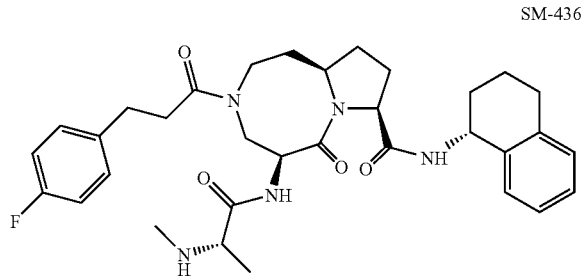

SM-436

EXAMPLE 51

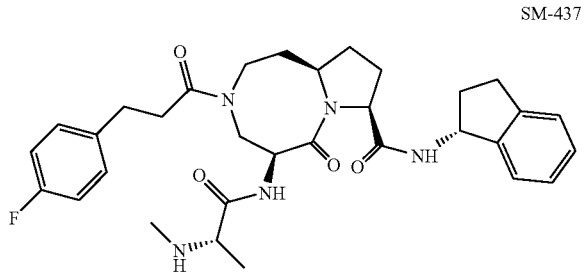

SM-437

Analytical data for SM-437: $^1$H NMR (MeOH-d$_4$, 300 M Hz) δ 7.45 (m, 1H), 7.30 (m, 4H), 7.14 (m, 1H), 7.02-6.84 (m, 2H), 5.43 (t, J=8.1 Hz, 1H), 4.79 (m, 1H), 4.39 (m, 1H), 4.00-3.77 (m, 4H), 3.56 (m, 1H), 3.40 (m, 1H), 3.00 (m, 6H), 2.70 (s, 3H), 2.49 (m, 1H), 2.28 (m, 1H), 2.00-1.75 (m, 6H), 1.54 (d, J=6.6 Hz, 3H), $^{13}$C NMR (MeOH-d$_4$, 300 M Hz) δ 174.1, 173.0, 169.1, 168.5, 143.6, 143.2, 137.4, 130.6, 127.7, 126.5, 124.5, 124.4, 62.1, 57.3, 54.8, 52.6, 51.6, 46.6, 35.1, 33.4, 32.4, 31.4, 30.8, 30.0, 27.5, 15.2.

EXAMPLE 52

Binding of Inhibitors to XIAP

In order to test the binding ability of the conformationally constrained Smac mimetics to IAP proteins, a sensitive and quantitative in vitro binding assay using the fluorescence polarization (FP) based method was developed and used to determine the binding affinity of Smac mimetics to XIAP protein (Nikolovska-Coleska et al., *Anal. Biochem.* 332:261-73 (2004)). For this assay, 5-carboxyfluorescein (5-Fam) was coupled to the lysine side chain of the mutated Smac peptide, AbuRPF-K-(5-Fam)-NH$_2$ (termed SM5F). The K$_d$ value of the binding of SM5F peptide to XIAP BIR3 protein was determined to be 17.92 nM, showing that this peptide binds to the surface pocket of the XIAP protein with high affinity. The recombinant XIAP BIR3 protein of human XIAP (residues 241-356) fused to His-tag was stable and soluble, and was used for the FP based binding assay.

The dose-dependent binding FP experiments were carried out with serial dilutions of the tested compounds in DMSO. A 5 μl sample of the tested samples and preincubated XIAP BIR3 protein (30 nM) and SM5F peptide (5 nM) in the assay buffer (100 mM potassium phosphate, pH 7.5; 100 μg/ml bovine gamma globulin; 0.02% sodium azide, purchased from Invitrogen™ Life Technology), were added in Dynex 96-well, black, round-bottom plates (Fisher Scientific) to produce a final volume of 125 μl. For each assay, the bound peptide control containing recombinant XIAP BIR3 protein and SM5F (equivalent to 0% inhibition) and free peptide control containing only free SM5F (equivalent to 100% inhibition) were included. The polarization values were measured after 3 hrs of incubation when the binding reached equilibrium using an ULTRA READER (Tecan U.S. Inc., Research Triangle Park, N.C.). IC$_{50}$ values, the inhibitor concentration at which 50% of bound peptide is displaced, were determined from a plot using nonlinear least-squares analysis. Curve fitting was performed using GRAPHPAD PRISM software (GraphPad Software, Inc., San Diego, Calif.).

Alternatively, in an optimized procedure, FP experiments were performed in Mucrofluor®, ThermoLabsystems, black, round-bottom plates (Fisher Scientific) using the Ultra plate reader (Tecan, Research Triangle Park, N.C.). The dose-dependent binding experiments were carried out with serial dilutions of active compounds. A 5 μl sample of the tested compound and preincubated XIAP BIR3 (30 nM) and SM5F Smac-Flu peptide (5 nM) in the assay buffer (100 mM potassium phosphate, pH 7.5; 100 ug/ml bovine gamma globulin; 0.02% sodium azide), were added in 96-well to produce a final volume of 125 μl. For each assay, negative controls containing XIAP-BIR3 and SM5F Smac-Flu (equivalent to 0% inhibition) and positive controls containing only free Smac-Flu peptide (equivalent to 100% inhibition) will be included on each assay plate. The plates were mixed on a shaker for 15 min and incubated at room temperature for 1-3 h. Polarization values were measured at excitation wavelength at 485 nm and emission wavelength at 530 nm. The percentage of inhibition were derived from the equation % inhibition=$100[1-(mP-mP_f)/(mP_b-mP_f)]$, where mP$_f$ is the free peptide control (minimal mP) and mP$_b$ is the bound peptide control (maximal mP). IC$_{50}$, the inhibitor concentration at which 50% of bound peptide is displaced, was determined from the plot using nonlinear least-squares analysis, and curve fitting was performed using GraphPad Prism® software. The K$_i$ value for a Smac mimetic was derived from the measured IC$_{50}$ value and the K$_d$ value of SM5F using a mathematical method and software specifically developed for FP-based assays.

When tested in the binding assay, the conformationally constrained Smac mimetics of the present invention exhibited strong binding affinity XIAP BIR3 protein as shown in Table 2. These binding affinities were more than 10-fold better than the binding affinity of the natural Smac peptide AVPI (SEQ ID NO: 1) (1,183±441 nM). These data suggest that conformationally constrained Smac mimetics will act as potent inhibitors of IAP activity.

TABLE 2

| Name | IC$_{50}$ (μM) |
|---|---|
| SM-401 | <1 |
| SM-402 | <1 |
| SM-403 | <1 |
| YP-245P3 | <100 |
| YP-246P | <10 |
| SM-330 | <1 |
| SM-337 | <1 |
| SM-350 | <1 |
| SM-356 | <1 |
| SM-376 | <0.1 |
| SM-377 | <0.1 |
| SM-404 | <1 |
| SM-405 | <1 |

TABLE 2-continued

| Name | IC$_{50}$ (μM) |
|---|---|
| SM-406 | <0.1 |
| SM-407 | <1 |
| SM-408 | <1 |
| SM-409 | <1 |
| SM-412 | <10 |
| SM-413 | <1 |
| SM-414 | <1 |
| SM-415 | <1 |
| SM-416 | <1 |
| SM-418 | <1 |
| SM-419 | <1 |
| SM-420 | <1 |
| SM-421 | <1 |
| SM-422 | <1 |
| SM-423 | <10 |
| SM-424 | <10 |
| SM-425 | <1 |
| SM-426 | <10 |
| SM-427 | <1 |
| SM-428 | >10 |
| SM-429 | <1 |
| SM-430 | <1 |
| SM-431 | <1 |
| SM-432 | <1 |
| SM-433 | <1 |
| SM-434 | <10 |
| SM-207 | <1 |
| SM-209 | <1 |
| SM-210 | <1 |
| SM-211 | <1 |
| SM-212 | <1 |
| SM-213 | <1 |
| SM-222 | <1 |
| SM-230 | <10 |
| SM-227 | <1 |

EXAMPLE 53

Binding of Inhibitors to Other IAP Proteins

In order to test the binding ability of conformationally constrained Smac mimetics to other IAP proteins (ML-IAP, cIAP1, and cIAP2) binding assay conditions were developed and optimized. The recombinant cIAP1 BIR3 domain (residues 253-363), cIAP2 BIR3 domain (residues 238-349), and ML-IAP BIR3 domain (residues 63-179), fused to a His-tag, were used in the binding assays. Competitive binding assays for other IAP proteins were performed similarly as that described for XIAP BIR3. Briefly, the same high-affinity tracer SM5F Smac-Flu peptide was used which binds cIAP1, cIAP2, and ML-IAP with high affinity: 4.1 nM, 6.6 nM, and 160 nM, respectively. The following protein concentration and tracer were used in the competitive assay: 10 nM cIAP1 and 2 nM SM5F, 25 nM cIAP2 and 2 nM SM5F, 300 nM ML-IAP and 5 nM SM5F

EXAMPLE 54

Cell Growth Inhibition by Conformationally Constrained Smac Mimetics

The effect of the compounds of the present invention on the growth of various cancer cell lines was tested. Cells were seeded in 96-well flat bottom cell culture plates at a density of 3000 cells/well with a tested compound and incubated at 37° C. in an atmosphere of 95% air and 5% $CO_2$ for 4 days. The rate of cell growth inhibition after treatment with different concentrations of the compound was determined using a WST-8 kit (2-(2-methoxy-4-nitrophenyl)-3-(4-nitrophenyl)-5-(2, 4 disulfophenyl)-2H-tetrazolium monosodium salt; Dojindo Molecular Technologies, Inc., Gaithersburg, Md.). WST-8 was added at a final concentration of 10% to each well, and then the plates were incubated at 37° C. for 2-3 hrs. The absorbance of the samples was measured at 450 nm using a ULTRA Tecan Reader (Molecular Device). The concentration of the tested compound that inhibited cell growth by 50% (IC$_{50}$) was calculated by comparing absorbance in untreated cells and the cells treated with the tested compound.

When tested against the MDA-MB-2131 human breast cancer cell line, the compounds of the present invention exhibited strong inhibitory activity as shown in Table 3, suggesting that the compounds are potent inhibitors of cancer cell growth. When tested against the SK-OV-3 ovarian cancer cell line, the compounds were even more potent (Table 3).

TABLE 3

| Name | MDA-MB-231 IC$_{50}$ (μM) | SK-OV-3 IC$_{50}$ (μM) |
|---|---|---|
| YP-337 | <1 | <1 |
| YP-376 | <1 | <1 |
| SM-401 | <1 | <1 |
| SM-402 | <1 | <1 |
| SM-403 | <1 | <1 |
| SM-404 | <1 | <1 |
| YP-245P3 | >1 | not tested |
| YP-246P | >1 | not tested |
| SM-330 | <1 | not tested |
| SM-350 | <1 | <1 |
| SM-356 | <1 | not tested |
| SM-377 | <1 | <1 |
| SM-405 | <1 | <1 |
| SM-406 | <1 | <1 |
| SM-407 | <1 | <1 |
| SM-408 | <1 | <1 |
| SM-409 | <1 | <1 |
| SH-207 | <1 | <1 |
| SM-412 | >1 | >1 |
| SM-413 | <100 | <100 |
| SM-414 | <100 | <100 |
| SM-415 | <1 | <1 |
| SM-416 | <10 | <10 |
| SM-418 | <10 | <10 |
| SM-419 | <10 | <10 |
| SM-420 | <1 | <1 |
| SM-421 | <1 | <1 |
| SM-422 | <1 | <1 |
| SM-423 | <100 | <100 |
| SM-424 | >10 | >10 |
| SM-425 | <10 | <10 |
| SM-426 | <10 | <10 |
| SM-427 | <1 | <1 |
| SM-428 | >5 | >5 |
| SM-429 | <10 | <10 |
| SM-430 | <10 | <10 |
| SM-431 | <1 | <1 |
| SM-432 | <10 | <10 |
| SM-433 | <10 | <10 |
| SM-434 | <10 | <10 |
| SM-207 | <10 | <10 |
| SM-209 | <10 | <10 |
| SM-210 | <1 | <1 |
| SM-211 | <10 | <10 |
| SM-212 | <10 | <10 |
| SM-213 | <10 | <10 |
| SM-222 | <1 | <1 |
| SM-230 | <100 | <100 |
| SM-227 | <10 | <10 |

EXAMPLE 55

Induction of Cell Death by YP-337

The ability of YP-337 to induce cell death was tested in the breast cancer MDA-MB-231 and ovarian cancer SK-OV-3 cell lines (Table 4). Cells were treated with YP-337 for 48 hours and cell viability was determined using the trypan blue exclusion assay.

TABLE 4

| | Approximate % of dead cells after 48 h | |
|---|---|---|
| Concentration (nM) | MDA-MB-231 | SK-OV-3 |
| Control | <5% | <5% |
| 0.1 | 10% | 20% |
| 1 | 35% | 40% |
| 10 | 60% | 65% |
| 100 | 75% | 75% |

EXAMPLE 56

Anti-tumor Activity of SM-406 (AT-406) in Breast Cancer Xenograft Model

The ability of SM-406 (AT-406) to act as anti-tumor agent was tested in the MDA-MB-231 breast cancer xenograft (nude mice) model. SM-406 (AT-406) was administered qd×5 per week for two weeks. As illustrated in FIG. 1, SM-406 (AT-406) at doses of 30, 100 and 200 mg/kg of SM-406 (AT-406) displayed anti-tumor activity. Dose-dependent weight loss up to 11% was observed at 100 and 200 mg/kg.

EXAMPLE 57

Figure 2:
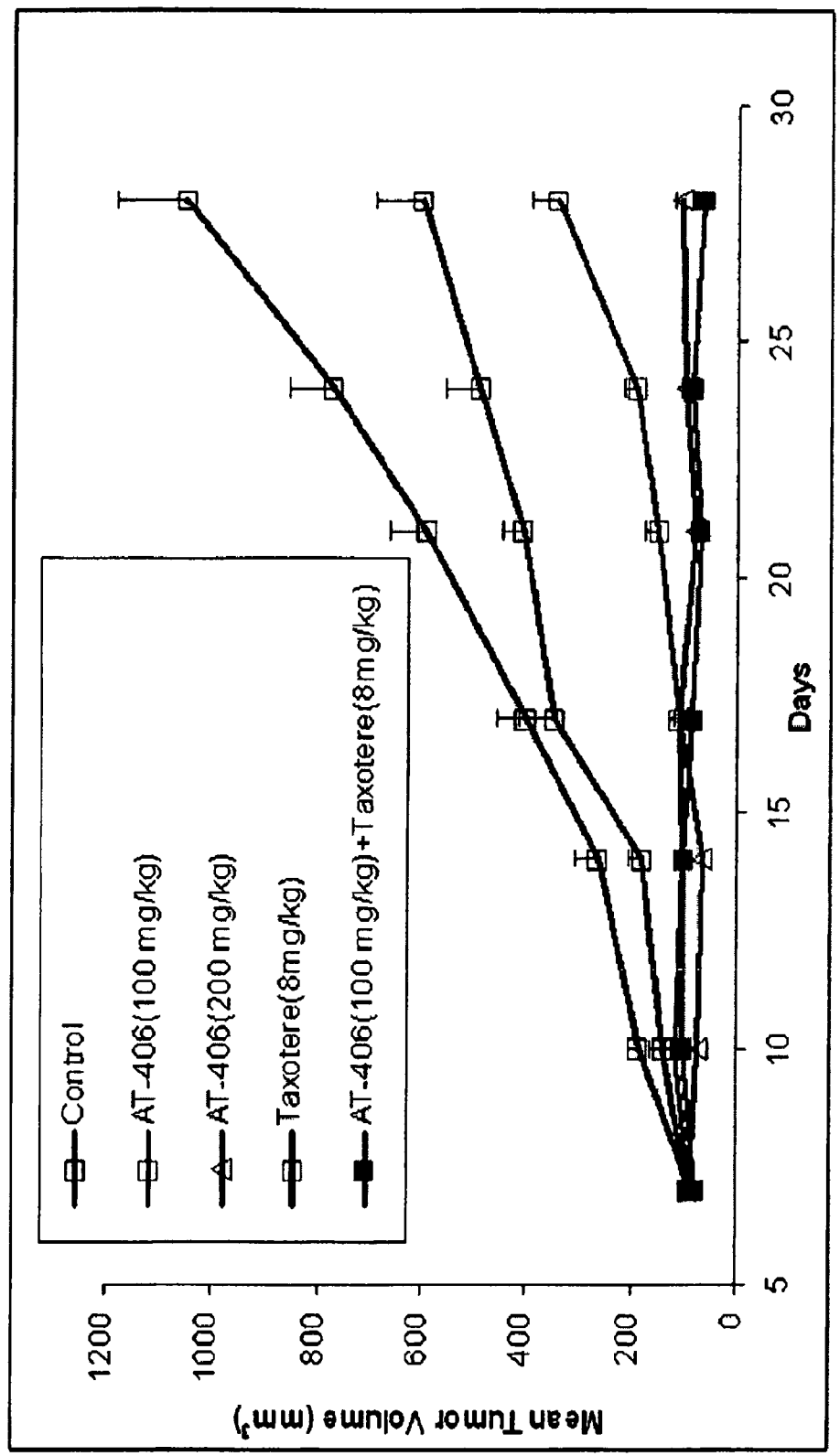
FIG. 2 is a graph illustrating the anti-tumor activity of SM-406 (AT-406) and taxotere in a prostate cancer xenograft model.

Anti-tumor Activity of SM-406 (AT-406) and Taxotere in Prostate Cancer Xenograft Model The ability of SM-406 (AT-406) to act as an anti-tumor agent alone and in combination with taxotere was tested in the PC-3 prostate cancer xenograft (nude mice) model. SM-406 (AT-406) was administered at qd×5 per week, taxotere once a week, for two weeks. As illustrated in FIG. 2, SM-406 (AT-406) at doses of 100 and 200 mg/kg displayed anti-tumor activity. In addition, SM-406 (AT-406) (100 mg/kg) in combination with taxotere (8 mg/kg) displayed enhanced anti-tumor activity.

EXAMPLE 58

Figure 3:
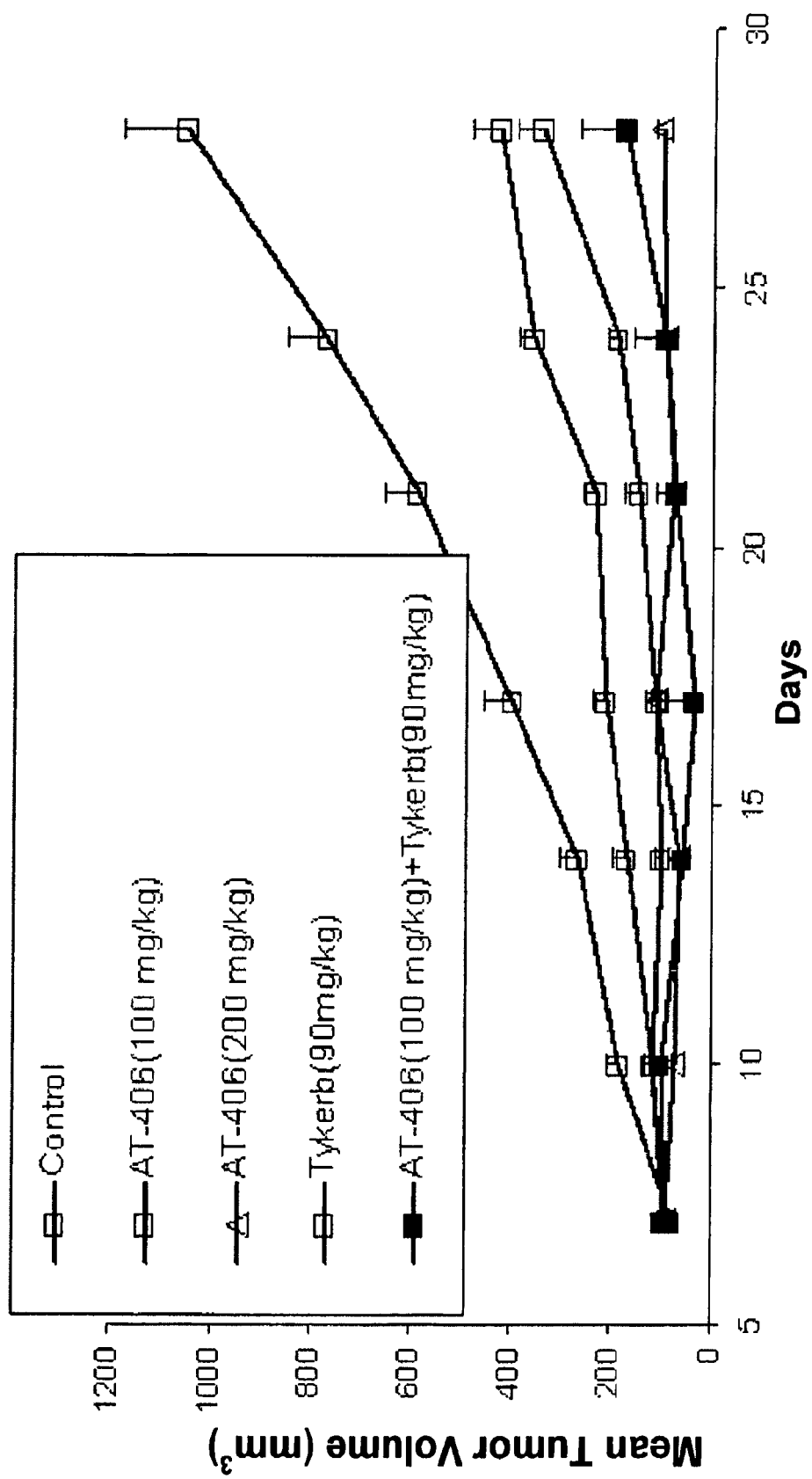
FIG. 3 is a graph illustrating the anti-tumor activity of SM-406 (AT-406) and Tykerb® in a prostate cancer xenograft model.

Anti-tumor Activity of SM-406 (AT-406) and Tykerb in Prostate Cancer Xenograft Model The ability of SM-406 (AT-406) to act as an anti-tumor agent alone and in combination with Tykerb® was tested in the PC-3 prostate cancer xenograft (nude mice) model. SM-406 (AT-406) was administered at qd×5 per week, Tykerb® bid×5 per week for two weeks. As illustrated in FIG. 3, SM-406 (AT-406) at doses of 100 and 200 mg/kg displayed anti-tumor activity. In addition, SM-406 (AT-406) (100 mg/kg) in combination with Tykerb® (90 mg/kg) displayed enhanced anti-tumor activity.

EXAMPLE 59

Figure 4:
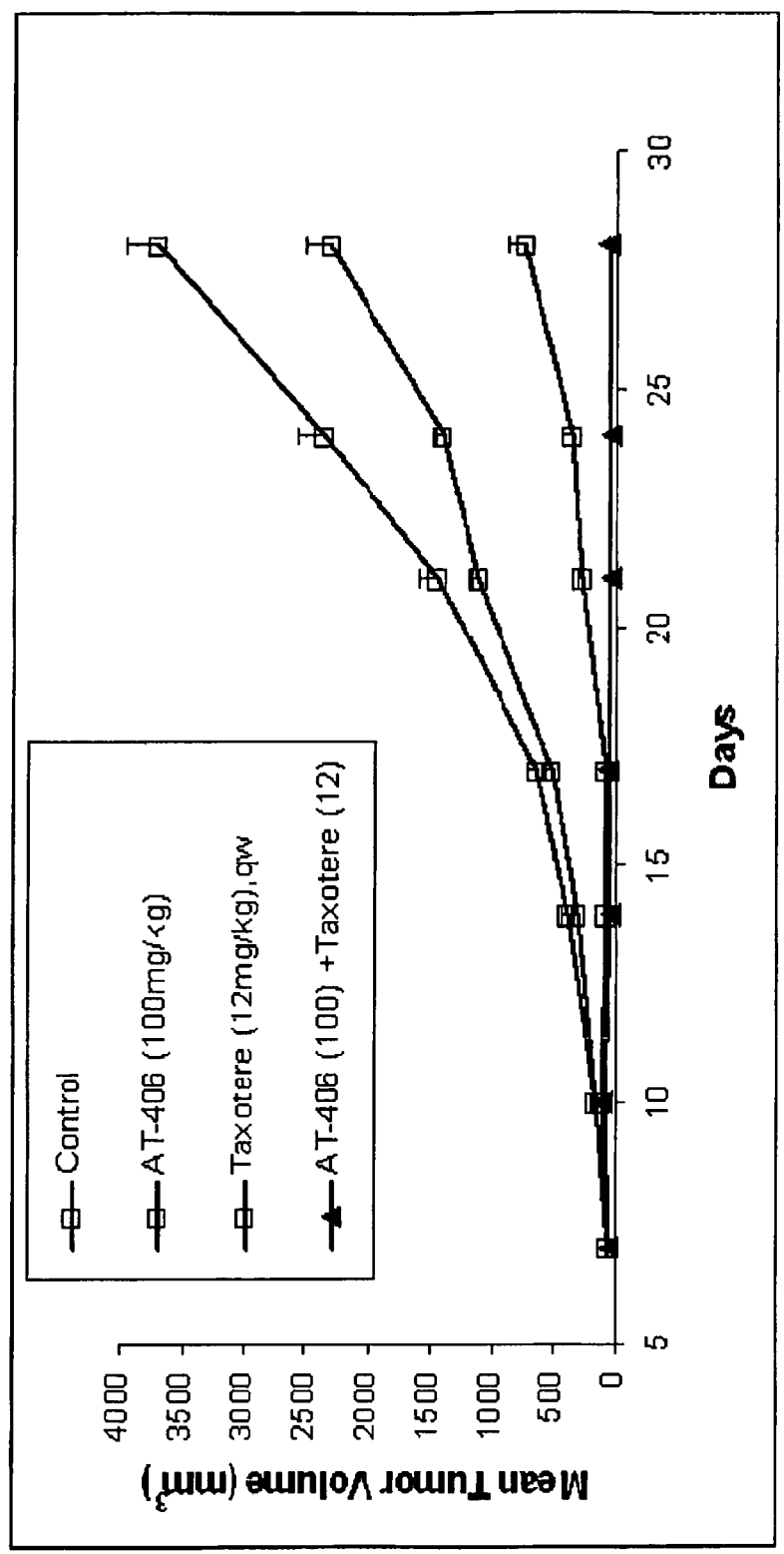
FIG. 4 is a graph illustrating the anti-tumor activity of SM-406 (AT-406) and taxotere in a breast cancer xenograft model.

Anti-tumor Activity of SM-406 (AT-406) and Taxotere in Breast Cancer Xenograft Model The ability of SM-406 (AT-406) to act as an anti-tumor agent alone and in combination with taxotere was tested in the 2LMP breast cancer xenograft model. SM-406 (AT-406) was administered at qd×5 per week, taxotere once a week, for two weeks. As illustrated in FIG. 4, SM-406 (AT-406) at a dose of 100 mg/kg displayed anti-tumor activity. In addition, SM-406 (AT-406) (100 mg/kg) in combination with taxotere (12 mg/kg) displayed anti-tumor activity.

EXAMPLE 60

Figure 5:
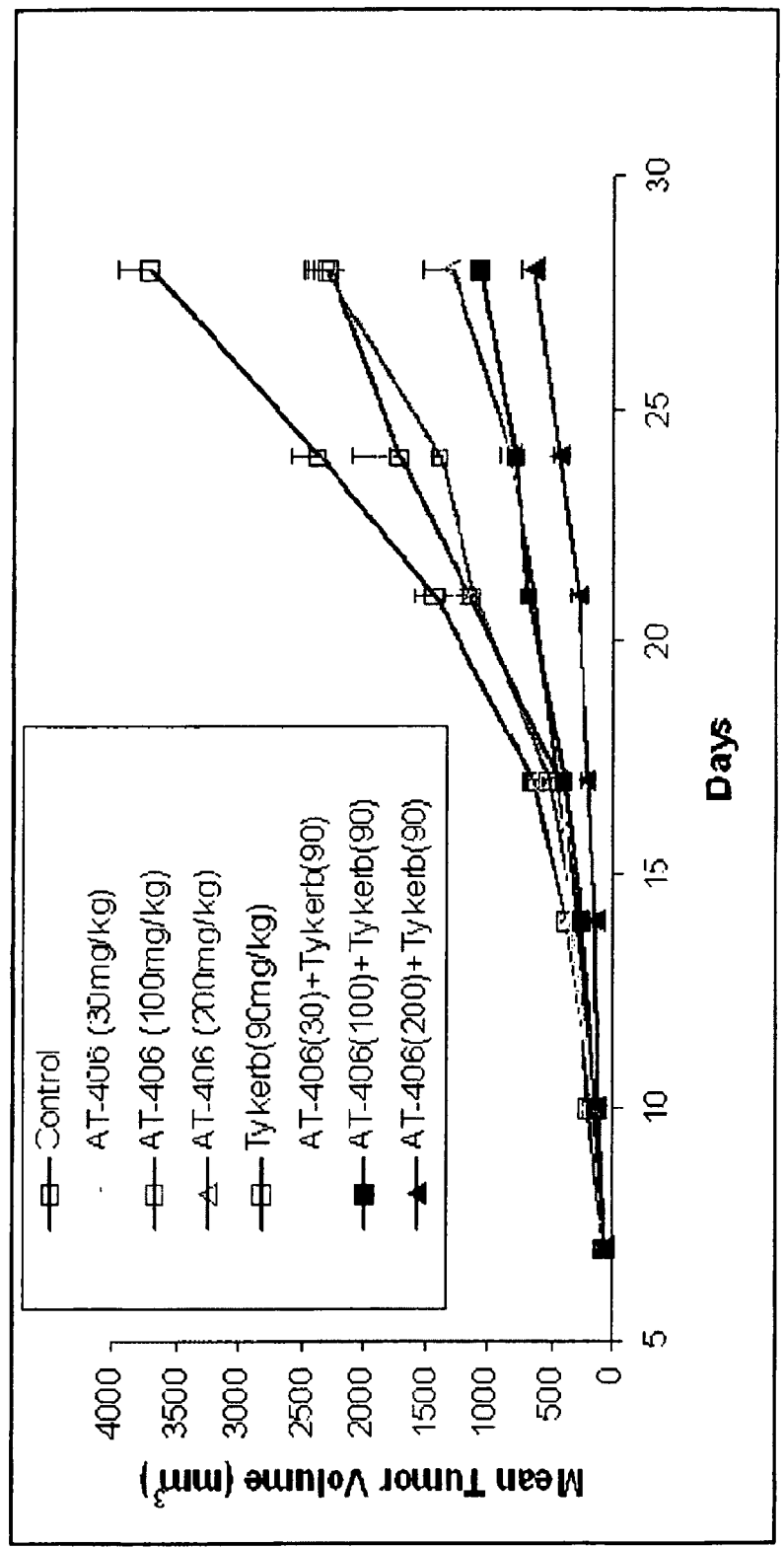
FIG. 5 is a graph illustrating the anti-tumor activity of SM-406 (AT-406) and Tykerb® in a breast cancer xenograft model.

Anti-tumor Activity of SM-406 (AT-406) and Tykerb in Breast Cancer Xenograft Model The ability of SM-406 (AT-406) to act as an anti-tumor agent alone and in combination with Tykerb® was tested in the 2LMP breast cancer xenograft model. SM-406 (AT-406) was administered at qd×5 per week, Tykerb® qd for two weeks. As illustrated in FIG. 5, SM-406 (AT-406) at doses of 30, 100 and 200 mg/kg displayed anti-tumor activity. In addition, SM-406 (AT-406) (30, 100 and 200 mg/kg) in combination with Tykerb® (90 mg/kg) displayed enhanced anti-tumor activity.

EXAMPLE 61

Anti-tumor Activity of SM-406 (AT-406) in Pancreatic Cancer Xenograft Model

Figure 6:
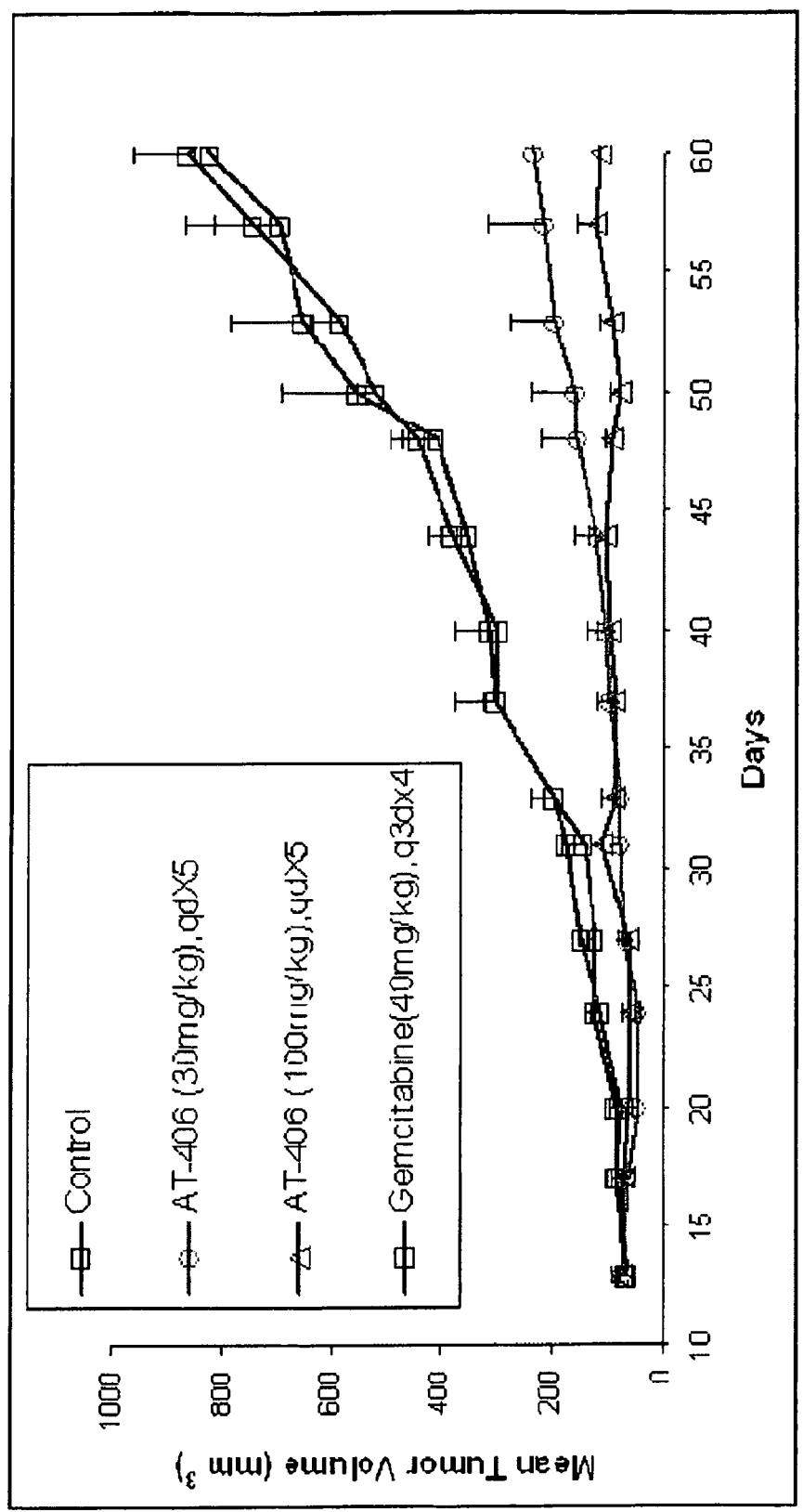
FIG. 6 is a graph illustrating the anti-tumor activity of SM-406 (AT-406) and gemcitabine in a pancreatic cancer xenograft model.

The ability of SM-406 (AT-406) to act as an anti-tumor agent was tested in the Panc-1 pancreatic cancer xenograft model. SM-406 (AT-406) was administered at qd×5 per week. As illustrated in FIG. 6, SM-406 (AT-406) at doses of 30 and 100 mg/kg displayed anti-tumor activity.

EXAMPLE 62

Dose-Schedule Optimization of SM-406 (AT-406) Breast Cancer Xenograft Model

Figure 7:
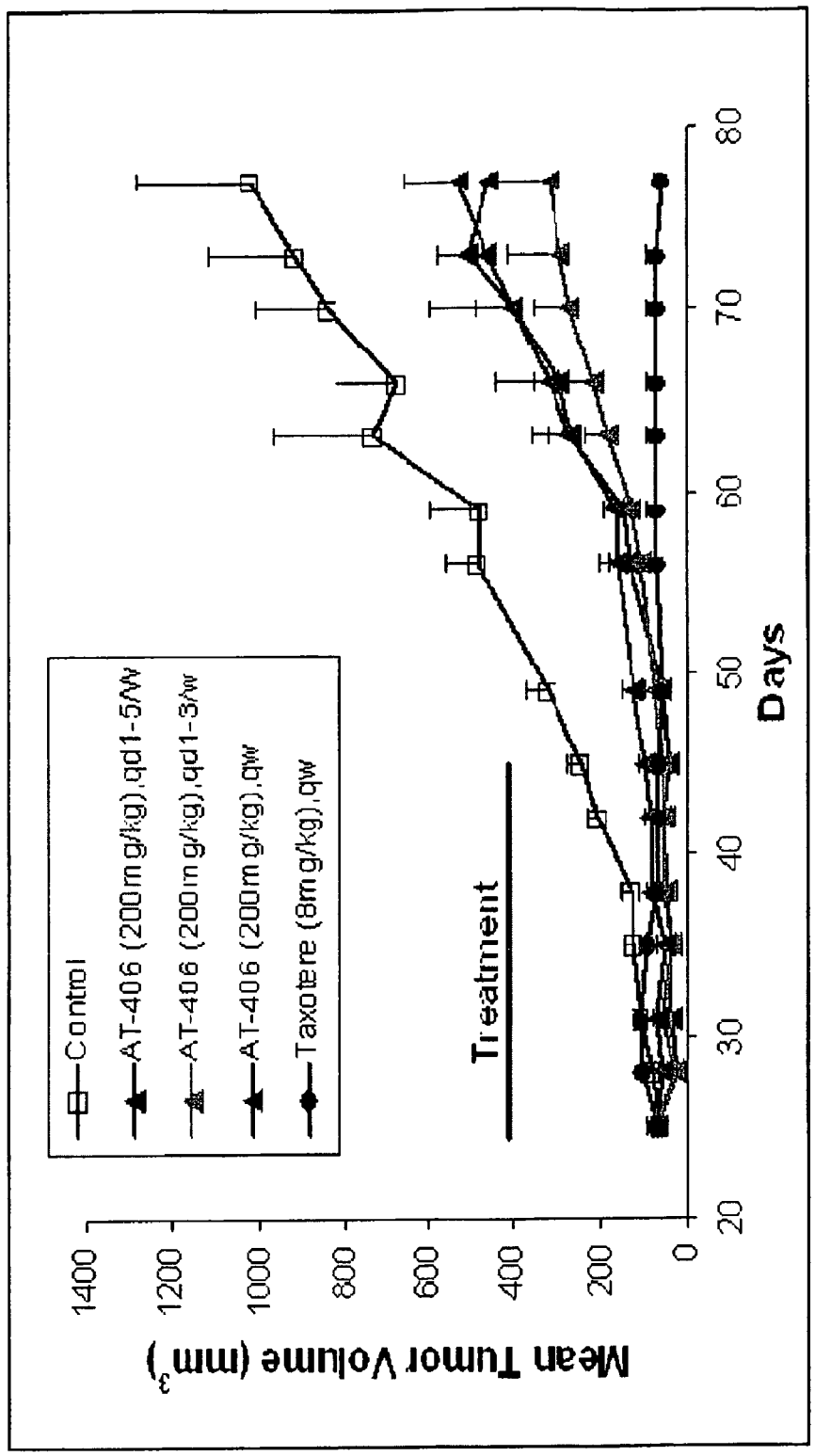
FIG. 7 is a graph illustrating dose schedule optimization studies of SM-406 (AT-406) in a breast cancer xenograft model.

As illustrated in FIG. 7, studies directed toward the optimization of the SM-406 (AT-406) dosing schedule in the MDA-MB-231 breast cancer xenograft (nude mice) model were carried out using 200 mg/kg of SM-406 (AT-406). Administration at qd X 5, day 1-5 per week, qd X 3, day 1-3 per week or once a week produced anti-tumor activity. Body weight loss was less in weekly dosing (<5%) compared to the other dosing schedules.

EXAMPLE 63

In Vitro Activity of SM-406 in Cancer Cell Lines

Figure 8:
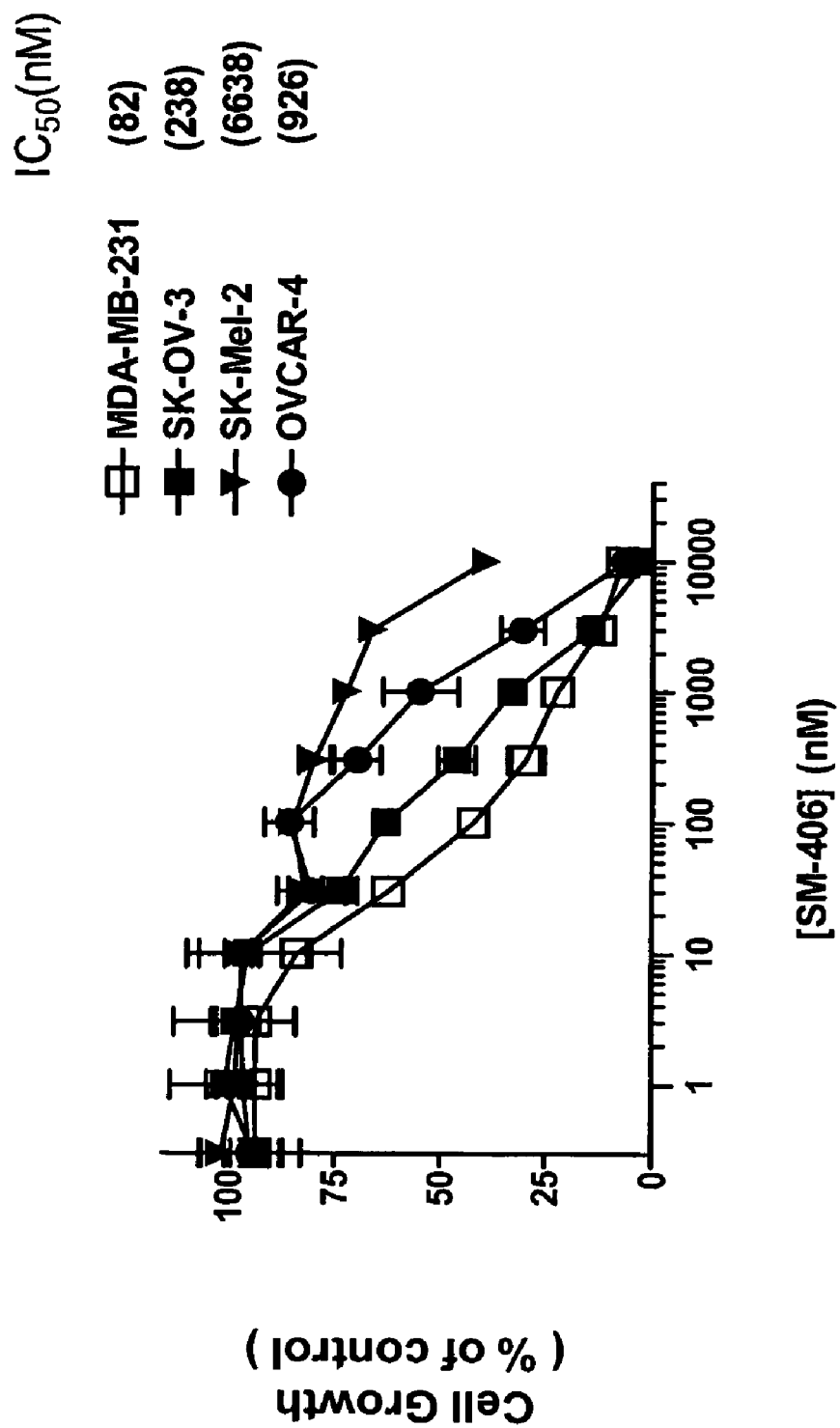
FIG. 8 is a graph illustrating the inhibition of cell growth by SM-406 in the MDA-MB-231 breast cancer cell line, SK-OV-3 and OVCAR-4 ovarian cancer cell lines and SK-Mel-2 melanoma cancer cell line.

The ability of SM-406 to inhibit cell growth as a single agent was tested in the MDA-MB-231 breast cancer cell line, SK-OV-3 and OVCAR-4 ovarian cancer cell lines and SK-Mel-2 melanoma cancer cell line. Cells were treated for 4 days. Cell growth was determined using a WST-based assay. As illustrated in FIG. 8, SM-406 inhibited all four cancer cell lines with $IC_{50}$ values of 82 nM, 238 nM, 6638 nM and 926 nM for MDA-MB-231, SK-OV-3, SK-Mel-2 and OVCAR-4, respectively.

EXAMPLE 64

In Vitro Activity of SM-406 in Cancer Cell Lines

Figure 9:
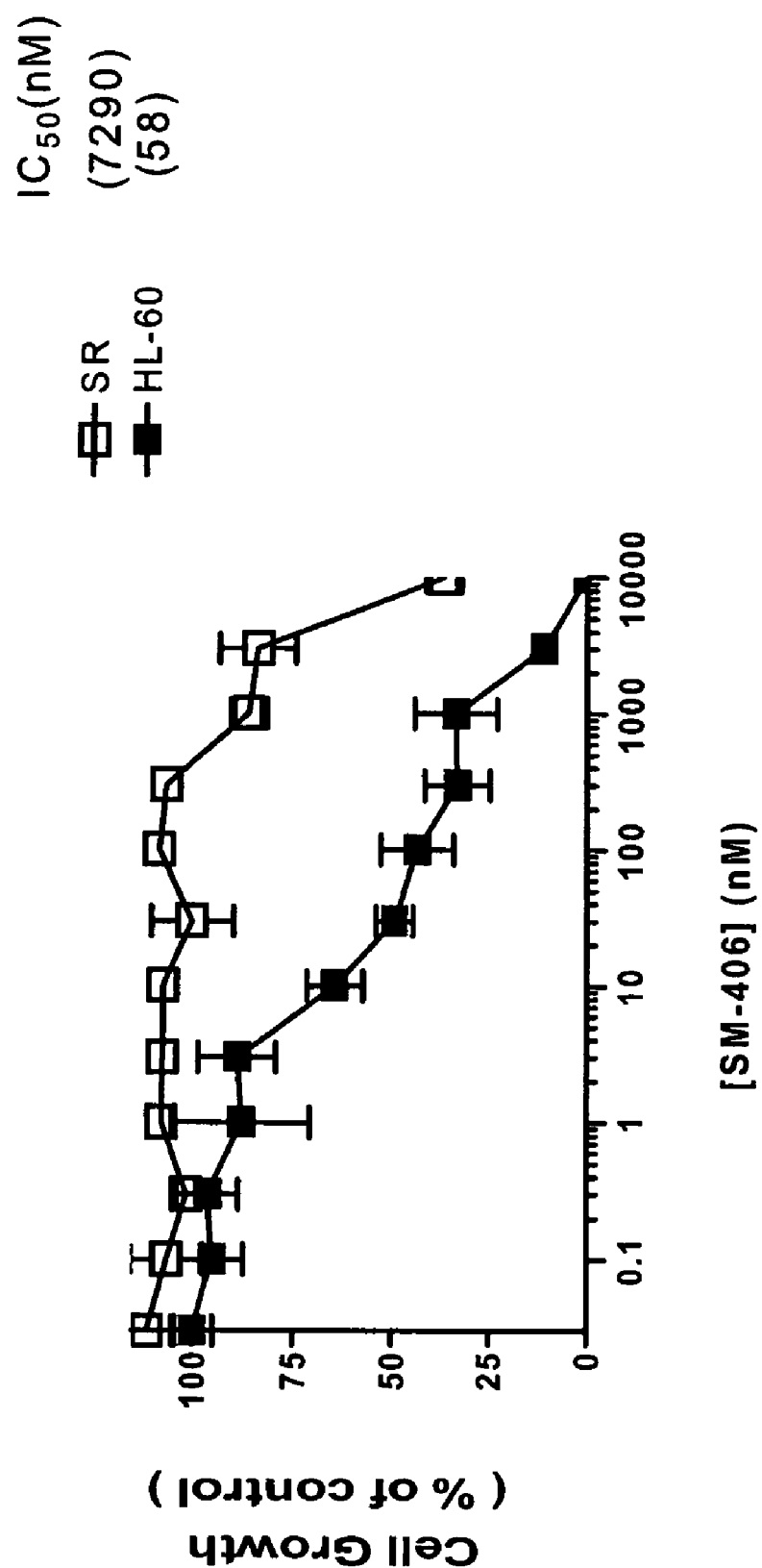
FIG. 9 is a graph illustrating the inhibition of cell growth by SM-406 in HL-60 and SR leukemia cell lines.

The ability of SM-406 to inhibit cell growth as a single agent was tested in the HL-60 and SR leukemia cell lines. Cells were treated for 4 days. Cell growth was determined using a WST-based assay. As illustrated in FIG. 9, SM-406 inhibited both cell lines with $IC_{50}$ values of 58 nM and 7290 nM, respectively.

EXAMPLE 65

In Vitro Activity of SM-406 in Cancer Cell Lines

Figure 10:
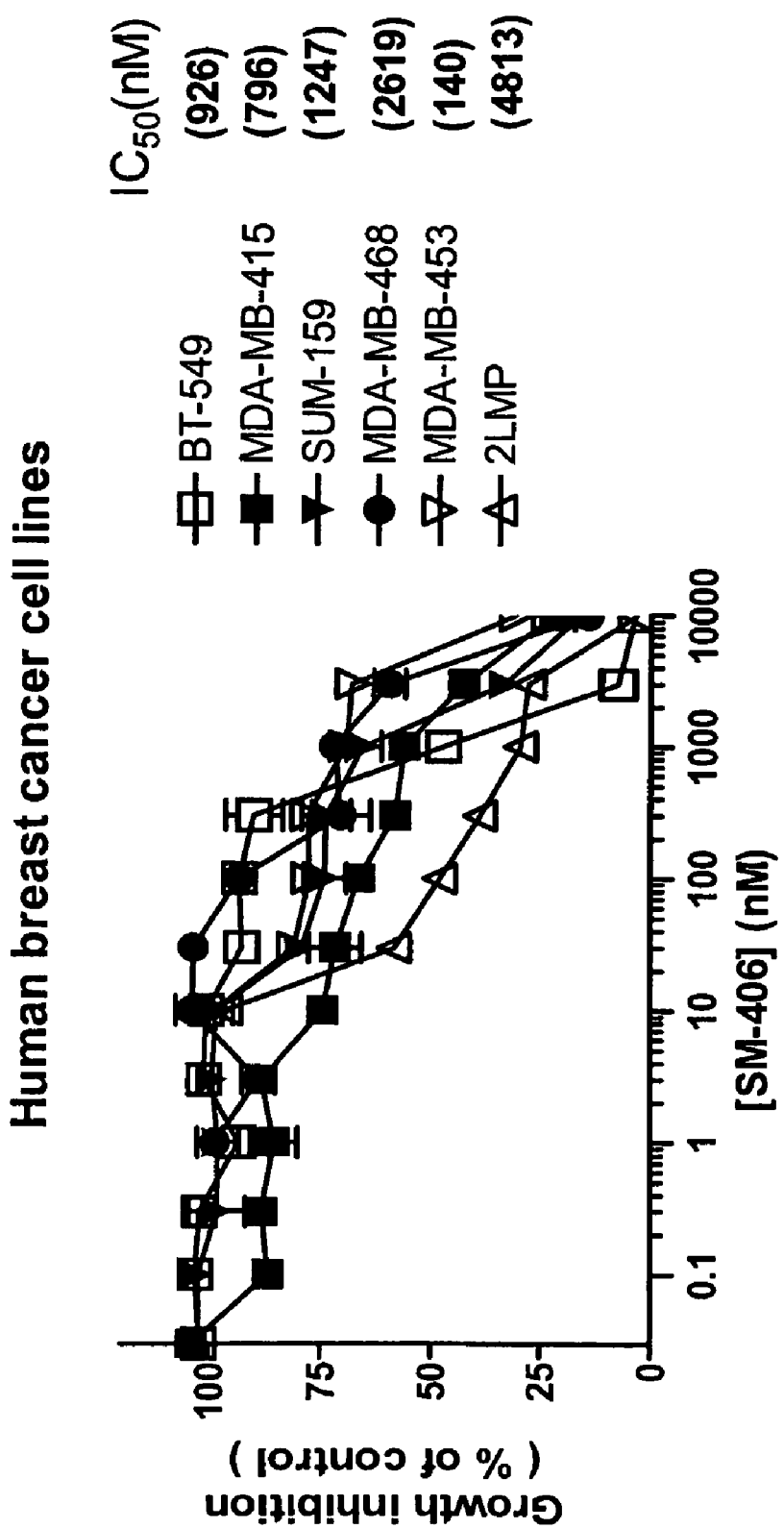
FIG. 10 is a graph illustrating the inhibition of cell growth by SM-406 in BT-549, MDA-MB-415, SUM-159, MDA-MB-468, MDA-MB-453 and 2LMP human breast cancer cell lines.

The ability of SM-406 to inhibit cell growth as a single agent was tested in the BT-549, MDA-MB-415, SUM-159, MDA-MB-468, MDA-MB-453 and 2LMP human breast cancer cell lines. Cells were treated for 4 days. Cell growth was determined using a WST-based assay. As illustrated in FIG. 10, SM-406 inhibited cell growth in all six cell lines.

EXAMPLE 66

In Vitro Activity of SM-406 in Combination with TNFα in MDA-MB-436 Cell Line

Figure 11:
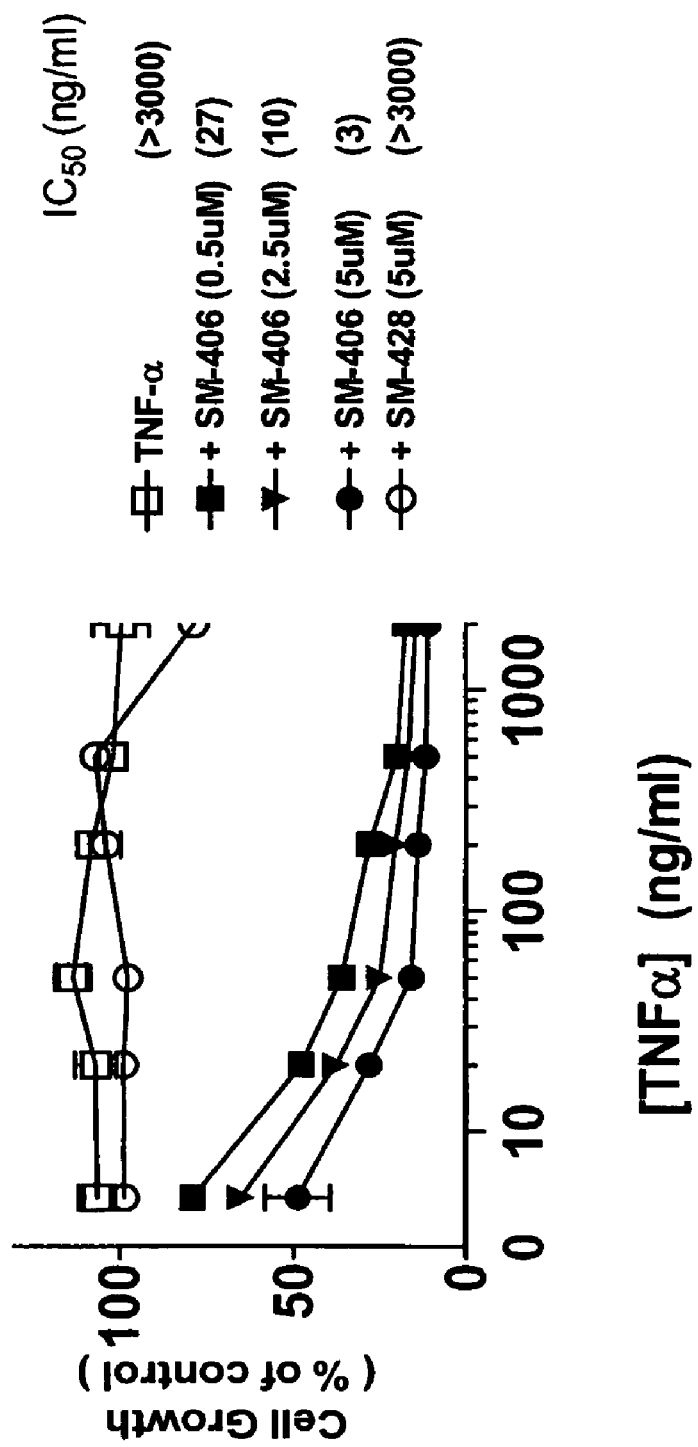
FIG. 11 is a graph illustrating the inhibition of cell growth of TNFα in combination with SM-406 in human breast cancer cell line MDA-MB-436.

The ability of SM-406 in combination with TNFα, and SM-428 as a single agent, to inhibit cell growth was tested in the human breast cancer cell line MDA-MB-436. Cells were treated with TNFα alone or in combination with different concentrations of SM-406, or with SM-428 for 4 days. Cell growth was determined using a WST-based assay. As illustrated in FIG. 11, SM-406 in combination with TNFα displayed enhanced inhibition of cell growth versus treatment with TNFα alone.

EXAMPLE 67

In vitro Activity of SM-406 in Combination with TNFα in SUM-159 Cell Line

Figure 12:
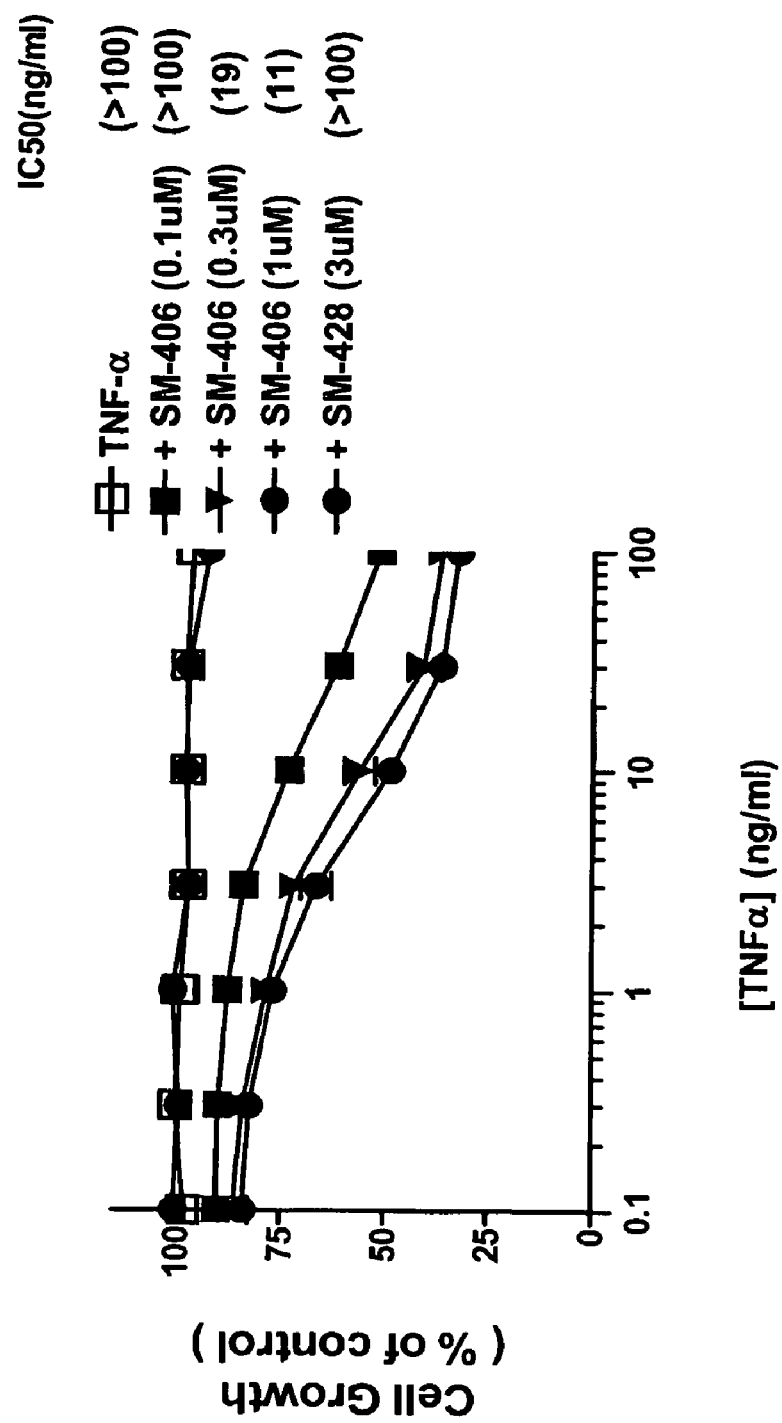
FIG. 12 is a graph illustrating the inhibition of cell growth of TNFα in combination with SM-406 in human breast cancer cell line SUM-159.

The ability of SM-406 in combination with TNFα, and SM-428 as a single agent, to inhibit cell growth was tested in the human breast cancer cell line SUM-159. Cells were treated with TNFα alone or in combination with different concentrations of SM-406, or with SM-428 for 4 days. Cell growth was determined using a WST-based assay. As illustrated in FIG. 12, SM-406 in combination with TNFα displayed enhanced inhibition of cell growth versus treatment with TNFα alone.

EXAMPLE 68

In vitro Activity of SM-406 in Combination with TRAIL in Panc-1 Cell Line

Figure 13:
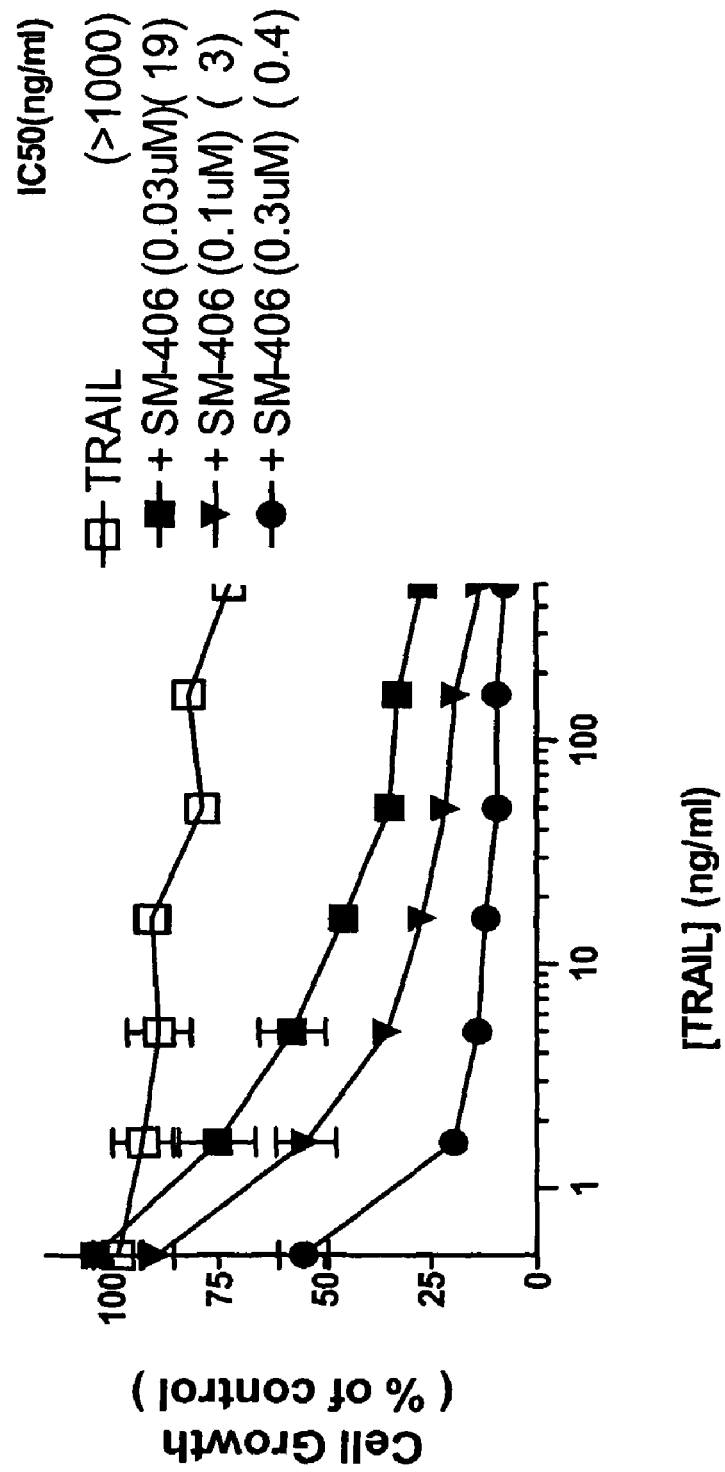
FIG. 13 is a graph illustrating the inhibition of cell growth by TRAIL in combination with SM-406 in human pancreatic cell line Panc-1.

The ability of SM-406 in combination with TRAIL to inhibit cell growth was tested in the human pancreatic cell line Panc-1. Cells were treated with TRAIL alone or in combination with different concentrations of SM-406 for 4 days. Cell growth was determined using a WST-based assay. As illustrated in FIG. 13, SM-406 in combination with TRAIL displayed enhanced inhibition of cell growth versus treatment with TRAIL alone.

EXAMPLE 69

Figure 14:
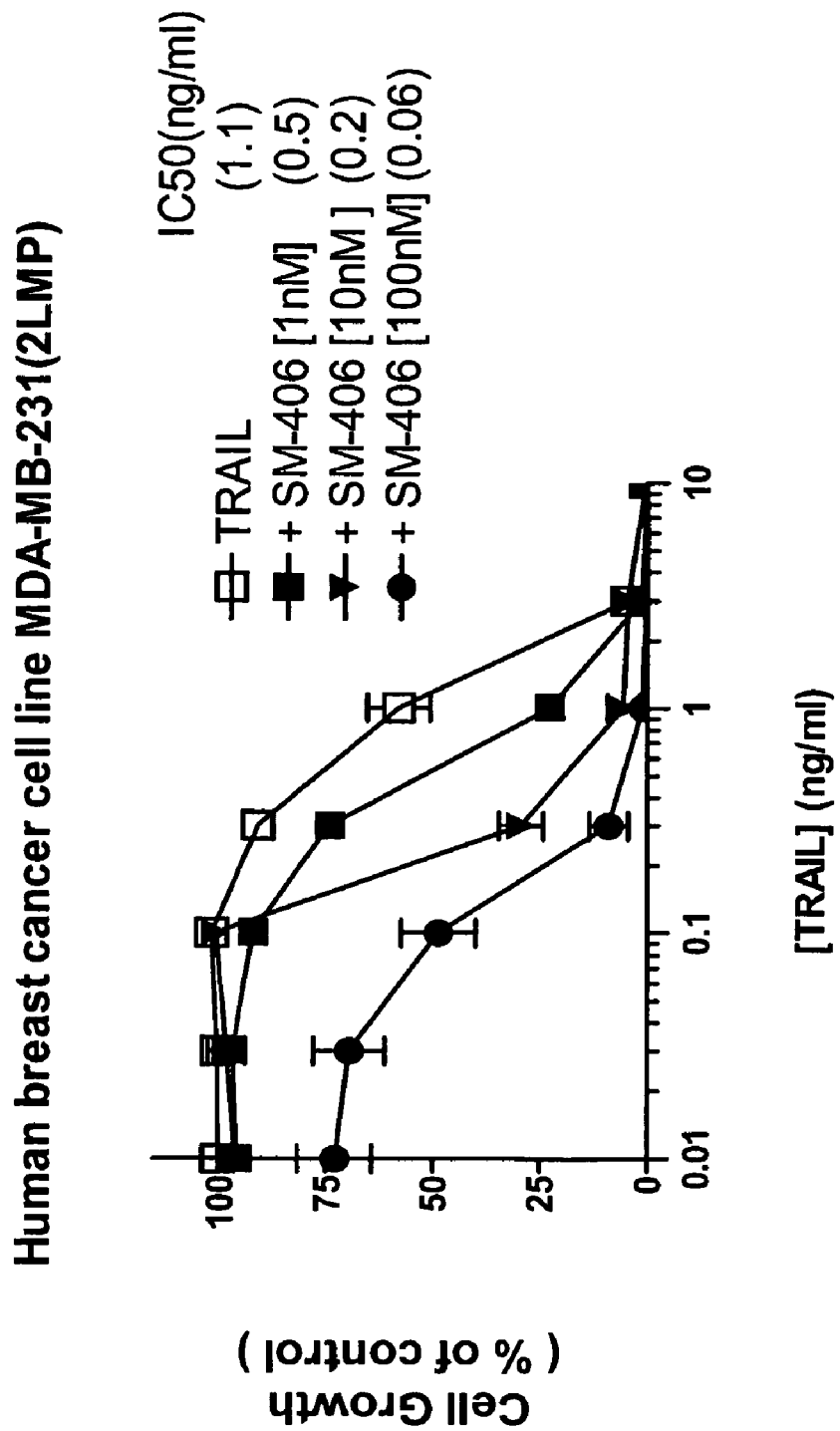
FIG. 14 is a graph illustrating the inhibition of cell growth by TRAIL in combination with SM-406 in human breast cancer cell line MDA-MB-231 (2LMP).

In Vitro Activity of SM-406 in Combination with TRAIL in MDA-231 (2LMP) Cell Line The ability of SM-406 in combination with TRAIL to inhibit cell growth was tested in the human breast cancer cell line MDA-MB-231 (2LMP). Cells were treated with TRAIL alone or in combination with different concentrations of SM-406 for 4 days. Cell growth was determined using a WST-based assay. As illustrated in FIG. 14, SM-406 in combination with TRAIL displayed enhanced inhibition of cell growth versus treatment with TRAIL alone.

EXAMPLE 70

In Vitro Activity of SM-406 in Combination with Gemcitabine in Panc-1 Cell Line

Figure 15:
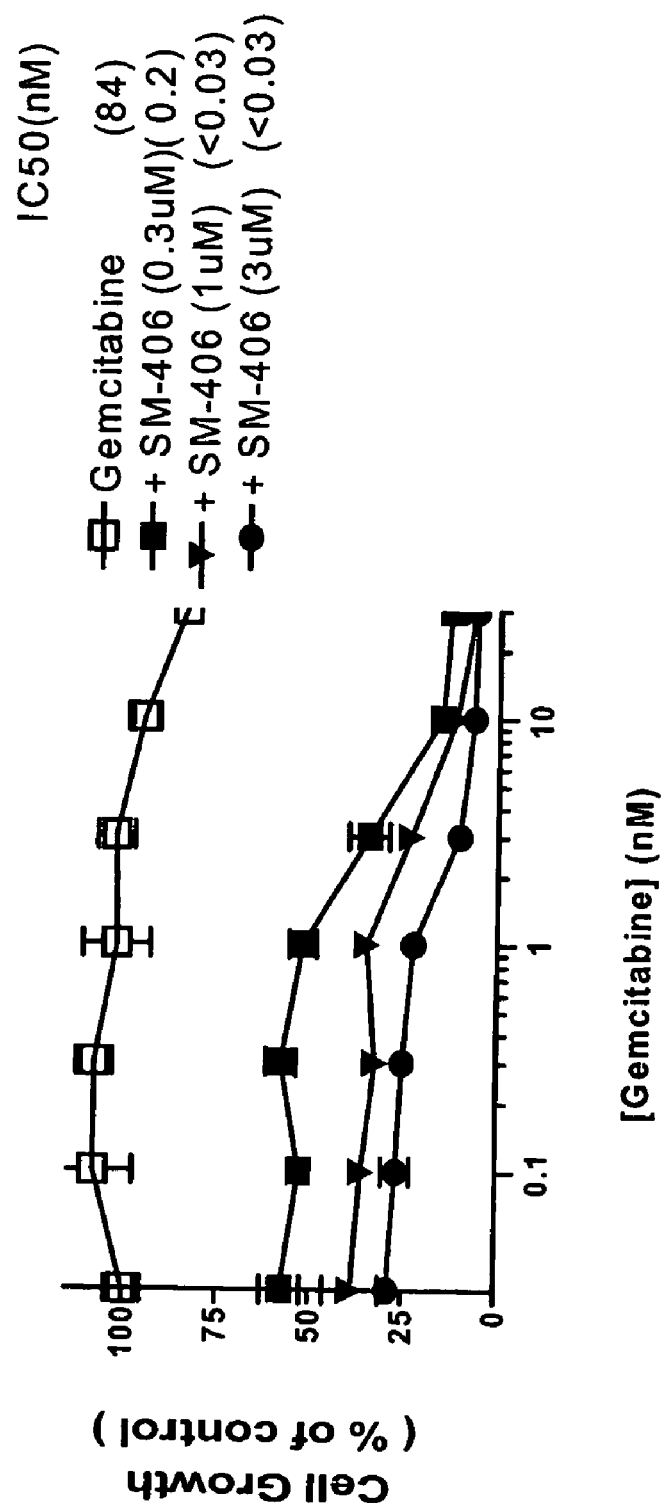
FIG. 15 is a graph illustrating the inhibition of cell growth by gemcitabine in combination with SM-406 in human pancreatic cell line Panc-1.

The ability of SM-406 in combination with gemcitabine to inhibit cell growth was tested in the human pancreatic cell line Panc-1. Cells were treated with gemcitabine alone or in combination with different concentrations of SM-406 for 4 days. Cell growth was determined using a WST-based assay. As illustrated in FIG. 15, SM-406 in combination with gemcitabine displayed enhanced inhibition of cell growth versus treatment with gemcitabine alone.

EXAMPLE 71

Figure 16:
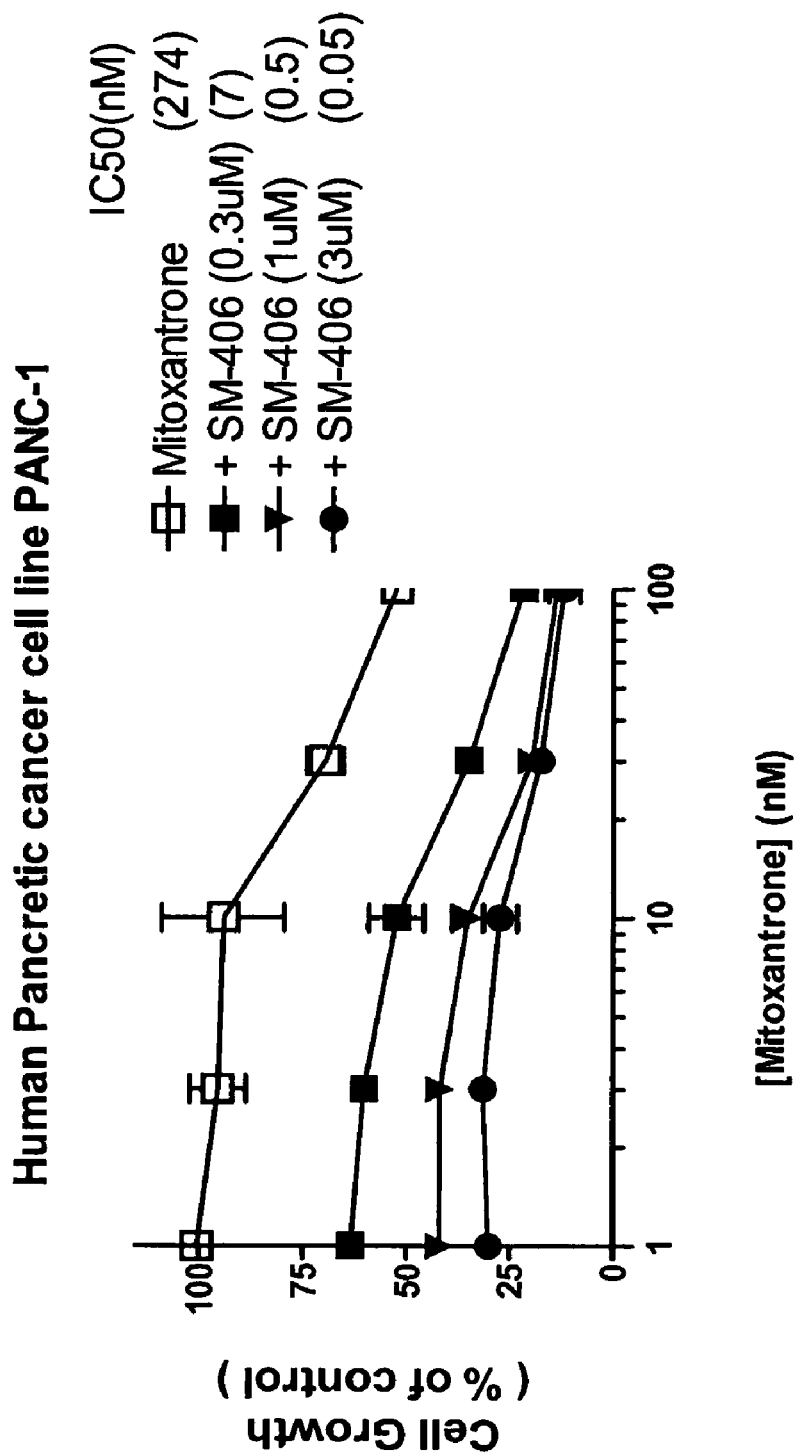
FIG. 16 is a graph illustrating the inhibition of cell growth by mitoxantrone in combination with SM-406 in human pancreatic cell line Panc-1.

In Vitro Activity of SM-406 in Combination with Mitoxantrone in Panc-1 Cell Line The ability of SM-406 in combination with mitoxantrone to inhibit cell growth was tested in the human pancreatic cell line Panc-1. Cells were treated with mitoxantrone alone or in combination with different concentrations of SM-406 for 4 days. Cell growth was determined using a WST-based assay. As illustrated in FIG. 16, SM-406 in combination with mitoxantrone displayed enhanced inhibition of cell growth versus treatment with mitoxantrone alone.

EXAMPLE 72

In Vitro Activity of SM-406 in Combination with Roscovitine in PC3 Cell Line

Figure 17:
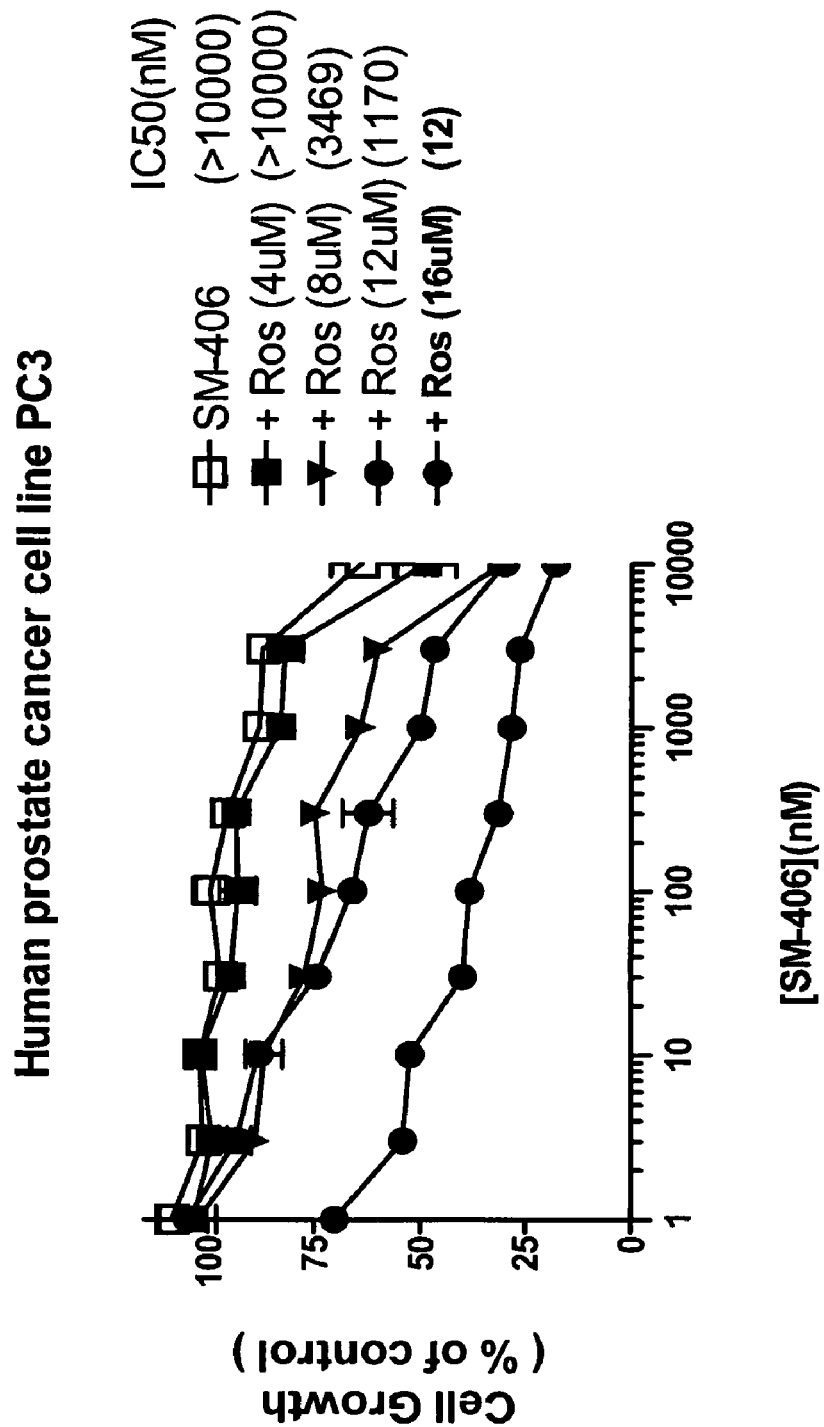
FIG. 17 is a graph illustrating the inhibition of cell growth by SM-406 in combination with roscovitine (Ros) in human prostate cell line PC3.

The ability of SM-406 in combination with roscovitine (Ros) to inhibit cell growth was tested in the human prostate cell line PC3. Cells were treated with SM-406 alone or in combination with different concentrations of roscovitine for 4 days. Cell growth was determined using a WST-based assay. As illustrated in FIG. 17, SM-406 in combination with roscovitine inhibited cell growth.

EXAMPLE 73

Figure 18:
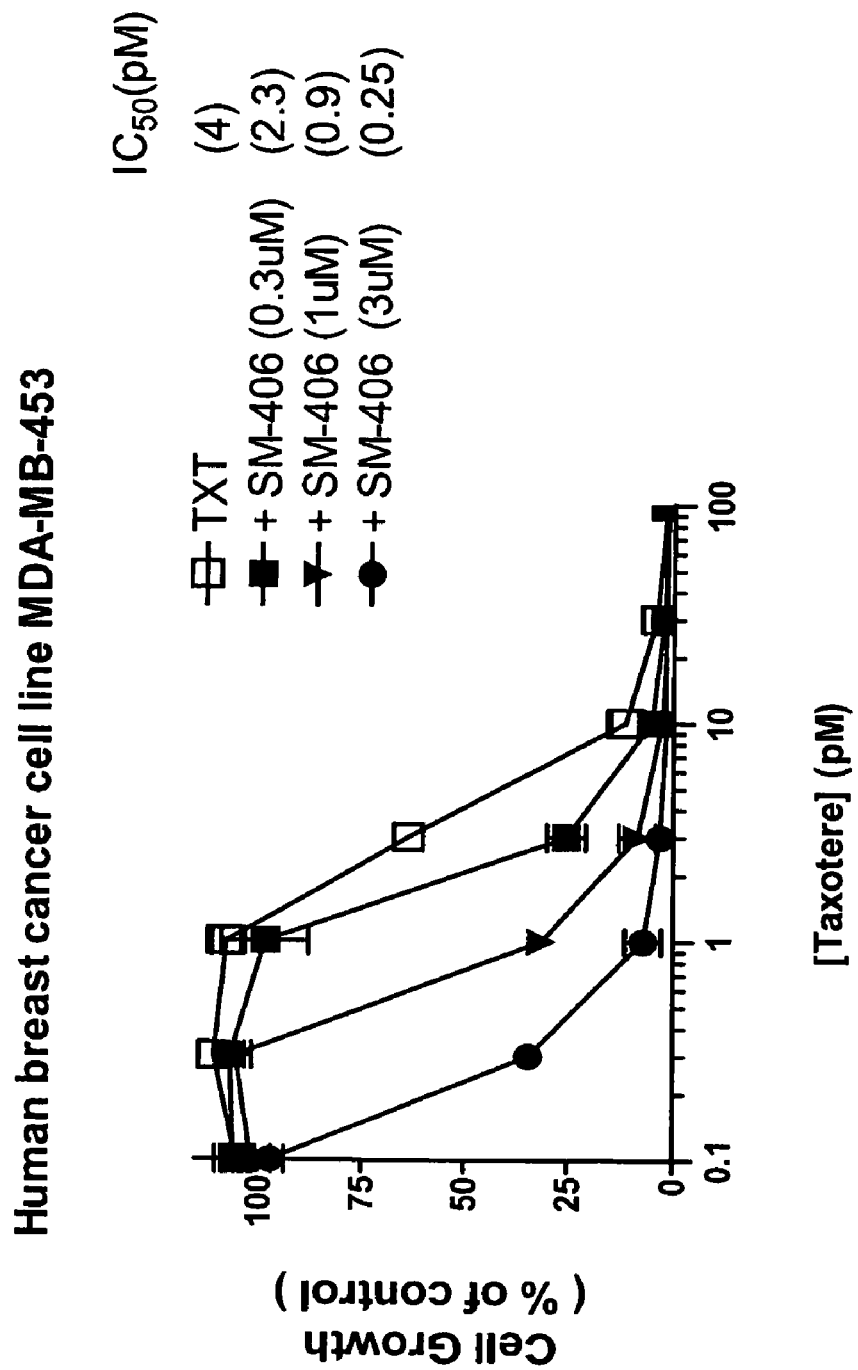
FIG. 18 is a graph illustrating the inhibition of cell growth of taxotere (TXT) in combination with SM-406 in human breast cancer cell line MDA-MB-453.

In Vitro Activity of SM-406 in Combination with Taxotere in MDA-MB-453 Cell Line The ability of SM-406 in combination with taxotere (TXT) to inhibit cell growth was tested in the human breast cancer cell line MDA-MB-453. Cells were treated with TXT alone or in combination with different concentrations of SM-406 for 4 days. Cell growth was determined using a WST-based assay. As illustrated in FIG. 18, SM-406 in combination with taxotere displayed enhanced inhibition of cell growth versus treatment with taxotere alone.

EXAMPLE 74

In Vitro Activity of SM-406 in Combination with VP-16 in Panc-1 Cell Line

Figure 19:
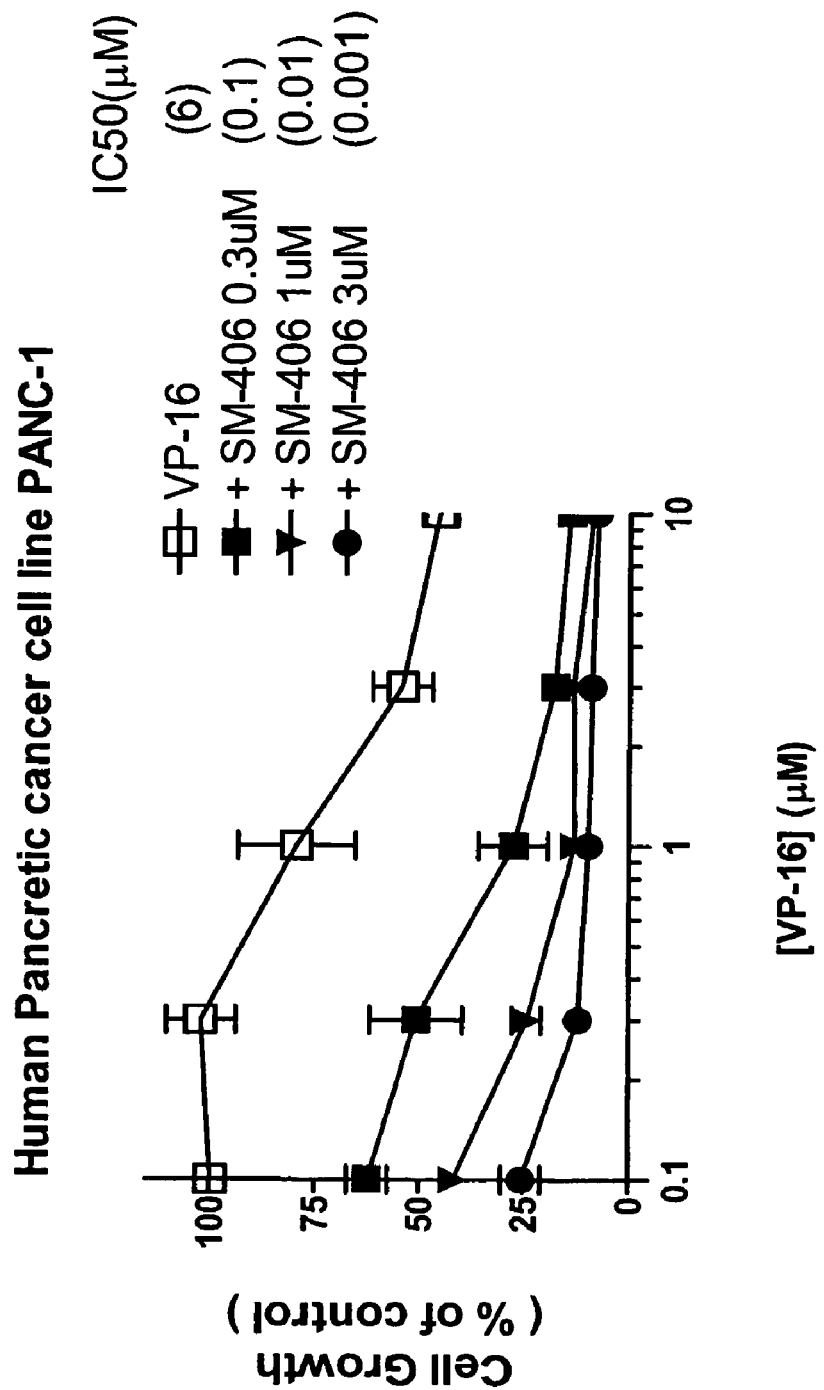
FIG. 19 is a graph illustrating the inhibition of cell growth of VP-16 in combination with SM-406 in human pancreatic cell line Panc-1.

The ability of SM-406 in combination with VP-16 to inhibit cell growth was tested in the human pancreatic cell line Panc-1. Cells were treated with VP-16 alone or in combination with different concentrations of SM-406 for 4 days. Cell growth was determined using a WST-based assay. As illustrated in FIG. 19, SM-406 in combination with VP-16 displayed enhanced inhibition of cell growth versus treatment with VP-16 alone.

EXAMPLE 75

Effect of SM-406 on cIAP-1 Protein in MDA-MB-231 Cells

Figure 20:
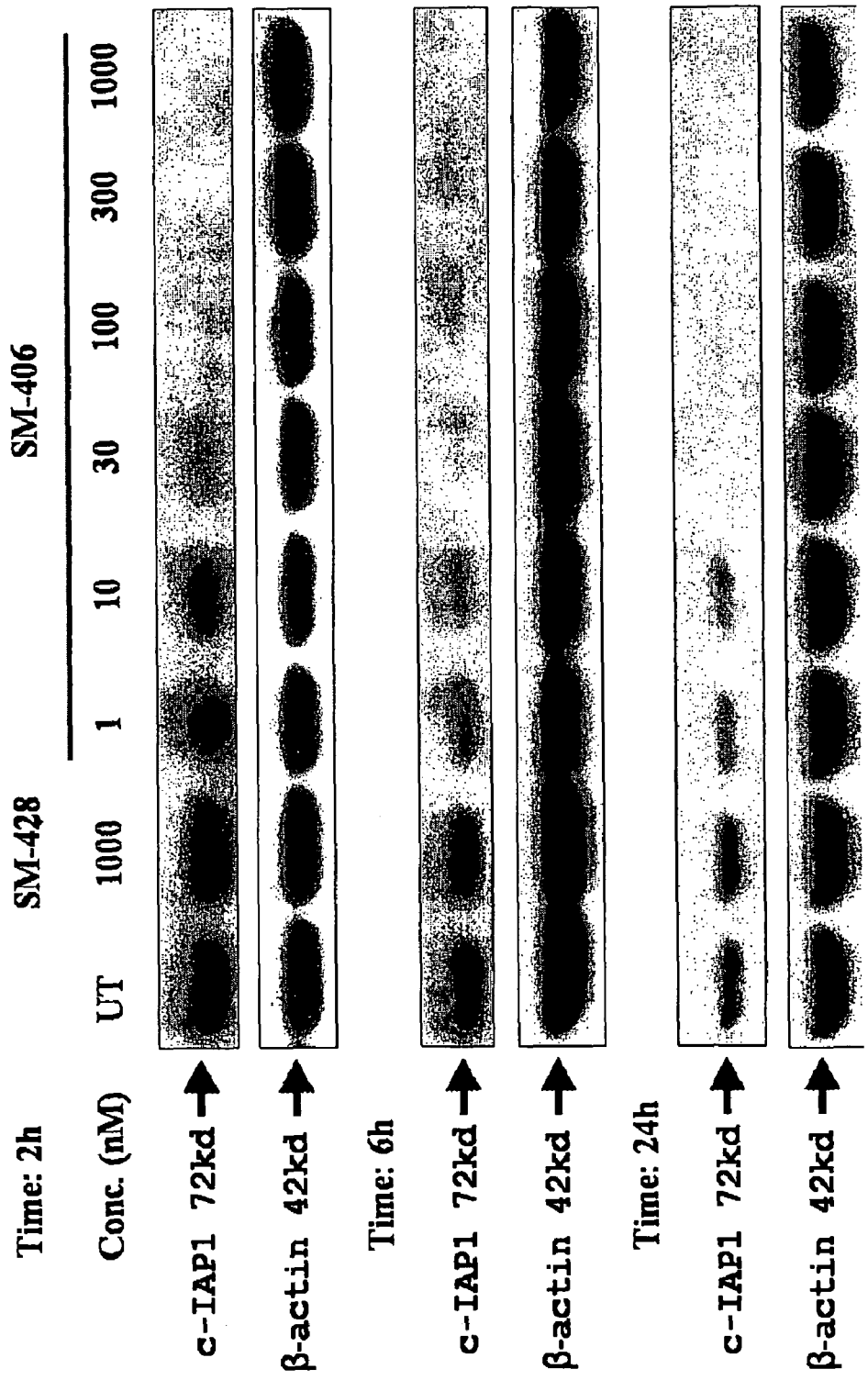
FIG. 20 is a figure illustrating the effect of Smac mimetics on cIAP-1 protein in MDA-MB-231 cancer cells.

The effect of SM-406 and SM-428 was measured on cIAP-1 protein in MDA-MB-231 cancer cells. Cells were treated with SM-406 or SM-428 at different concentrations and time-points. Protein levels were analyzed by Western blottings. As illustrated in FIG. 20, SM-406 reduced cIAP-1 protein levels.

EXAMPLE 76

Effect of SM-406 on cIAP-1 and cIAP-2 Proteins in SK-OV-3 Cells

Figure 21:
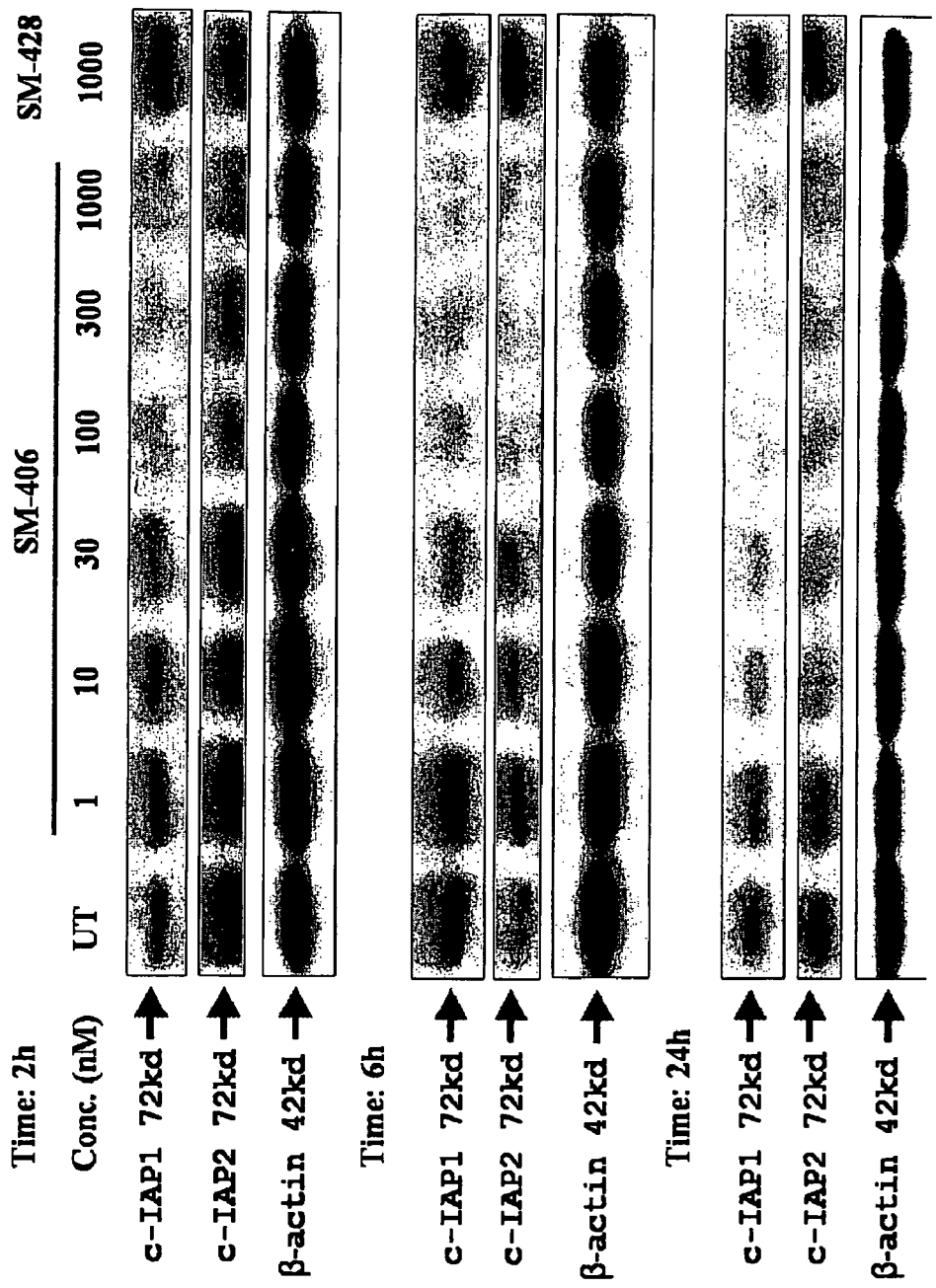
FIG. 21 is a figure illustrating the effect of Smac mimetics on cIAP-1/2 proteins in SK-OV-3 cancer cells.

The effect of SM-406 and SM-428 was measured on cIAP-1 and cIAP-2 proteins in SK-OV-3 cancer cells. Cells were treated with SM-406 or SM-428 at different concentrations and time-points. Protein levels were analyzed by Western blotting. As illustrated in FIG. 21, SM-406 reduced cIAP-1 and cIAP-2 protein levels.

EXAMPLE 77

Induction of Apoptosis by SM-406 in MDA-MB-231 Cells

Figure 22:
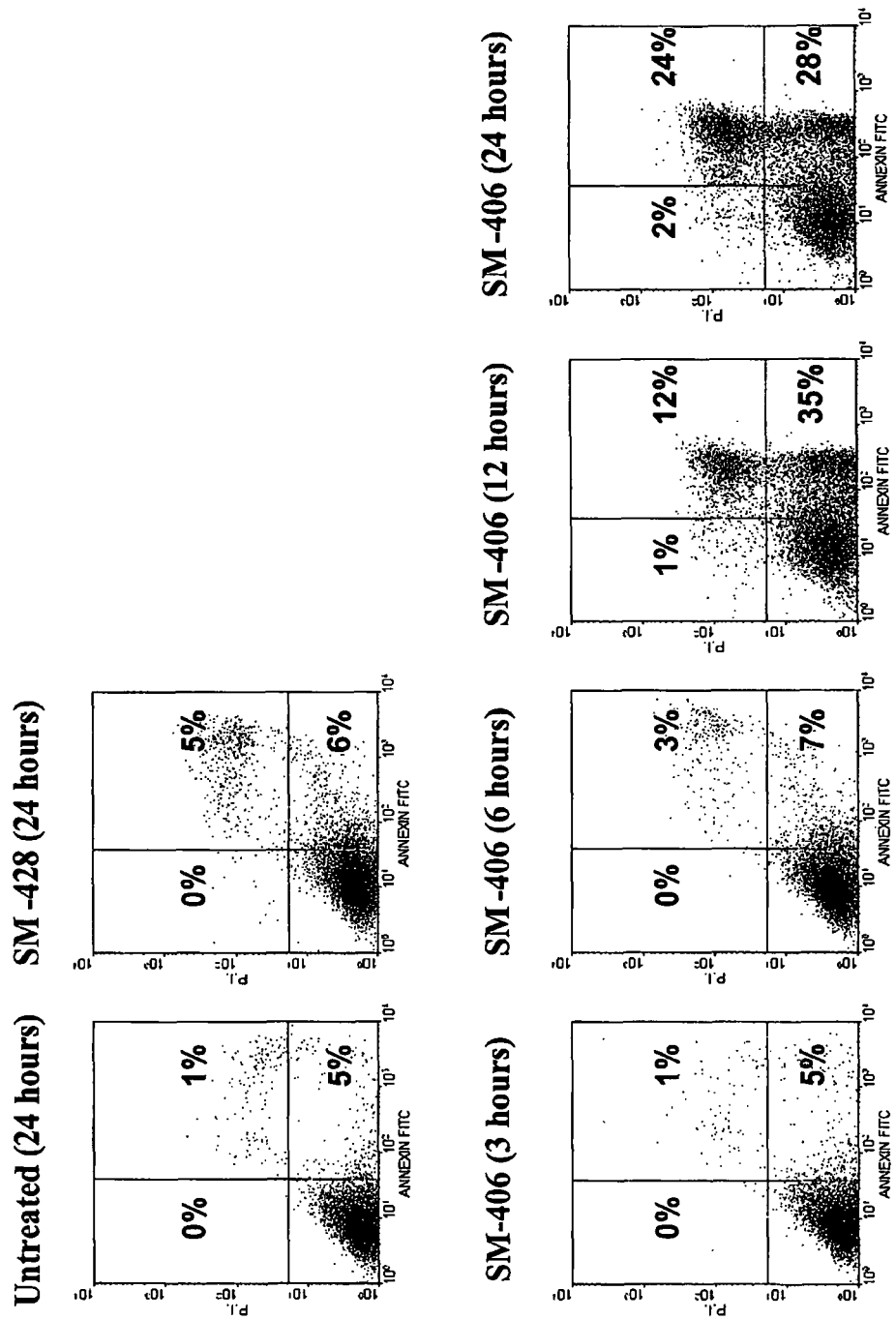
FIG. 22 is a figure illustrating the induction of apoptosis by SM-406 in MDA-MB-231 breast cancer cells.

The induction of apoptosis by SM-406 or SM-428 was measured in MDA-MB-231 breast cancer cells. Cells were treated with SM-406 or SM-428 for different periods of time and apoptosis was analyzed by FITC Annexin V/propidium iodide staining using a flow cytometer. As illustrated in FIG. 22, 3 µM of SM-406 induced apoptosis in MDA-MB-231 breast cancer cells.

EXAMPLE 78

Induction of Apoptosis by SM-406 in SK-OV-3 Cells

Figure 23:
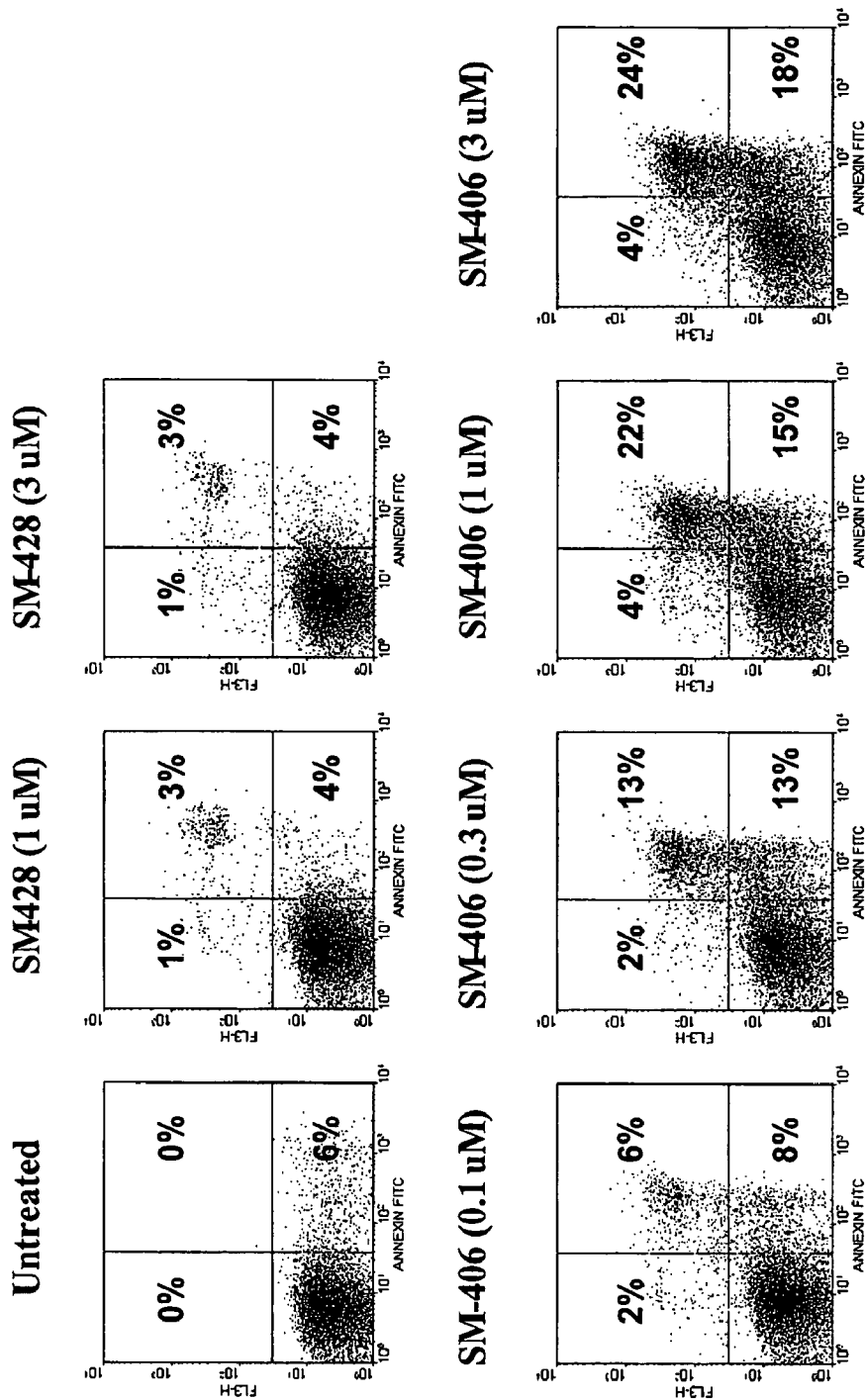
FIG. 23 is a figure illustrating the induction of apoptosis by SM-406 in SK-OV-3 ovarian cancer cells.

The induction of apoptosis by SM-406 or SM-428 was measured in SK-OV-3 ovarian cancer cells. Cell were treated with SM-406 or SM-428 at different concentrations. Apoptosis was analyzed by FITC Annexin V/propidium iodide staining using a flow cytometer. As illustrated in FIG. 23, 0.1, 0.3, 1 and 3 µM of SM-406 induced apoptosis in SK-OV-3 ovarian cancer cells.

EXAMPLE 79

Induction of Apoptosis by SM-406 in Panc-1 Cells

Figure 24:
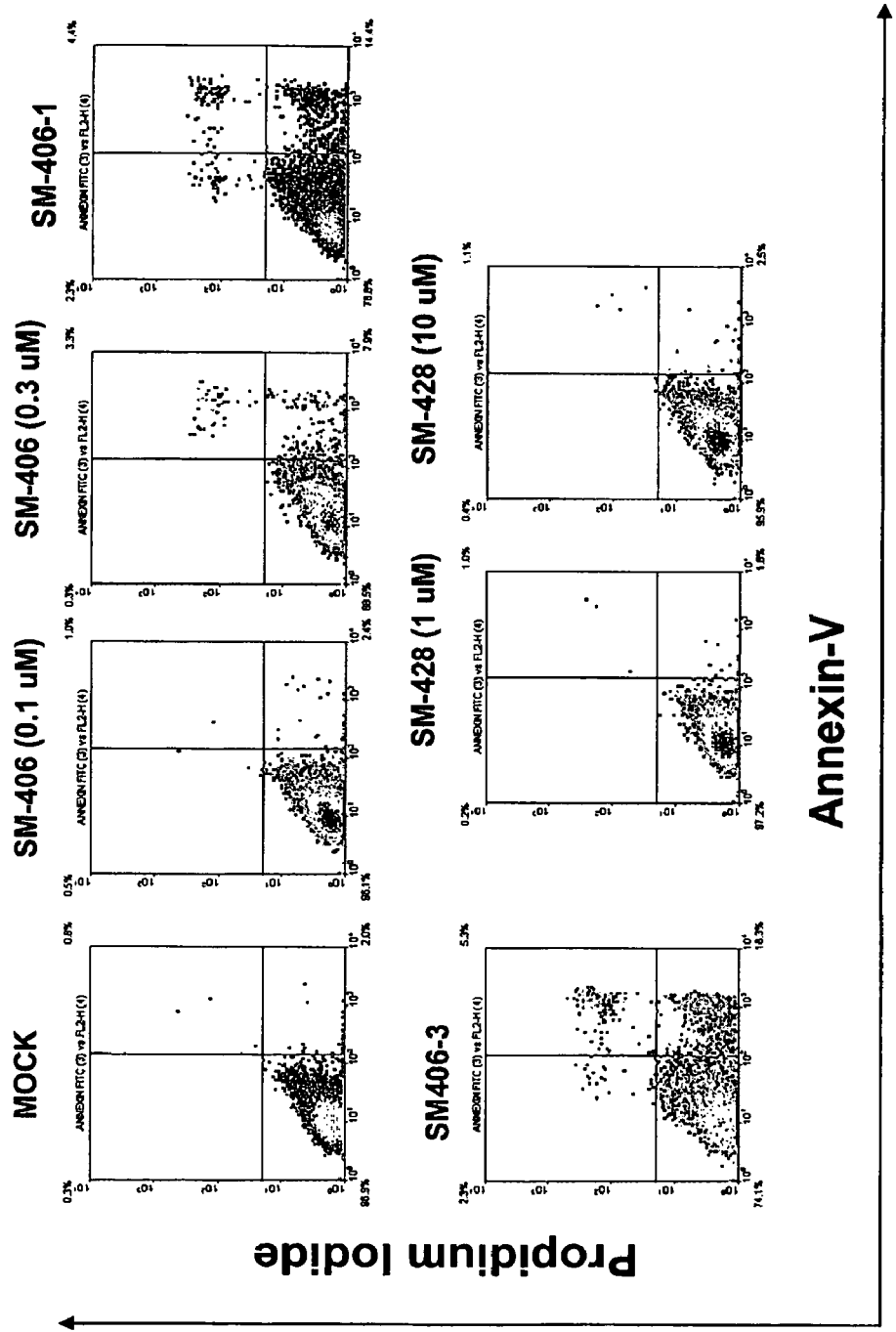
FIG. 24 is a figure illustrating the induction of apoptosis by SM-406 in Panc-1 pancreatic cancer cells.

The induction of apoptosis by SM-406 or SM-428 was measure in Panc-1 pancreatic cancer cells. Cells were treated with SM-406 or SM-428 at different concentrations. Apoptosis was analyzed by FITC Annexin V/propidium iodide staining using a flow cytometer. As illustrated in FIG. 24, 0.3, 1 and 3 µM of SM-406 induced apoptosis in panc-1 pancreatic cancer cells.

EXAMPLE 80

Anti-tumor Activity of SM-406 in MDA-MB-231 Xenograft Model

Figure 25:
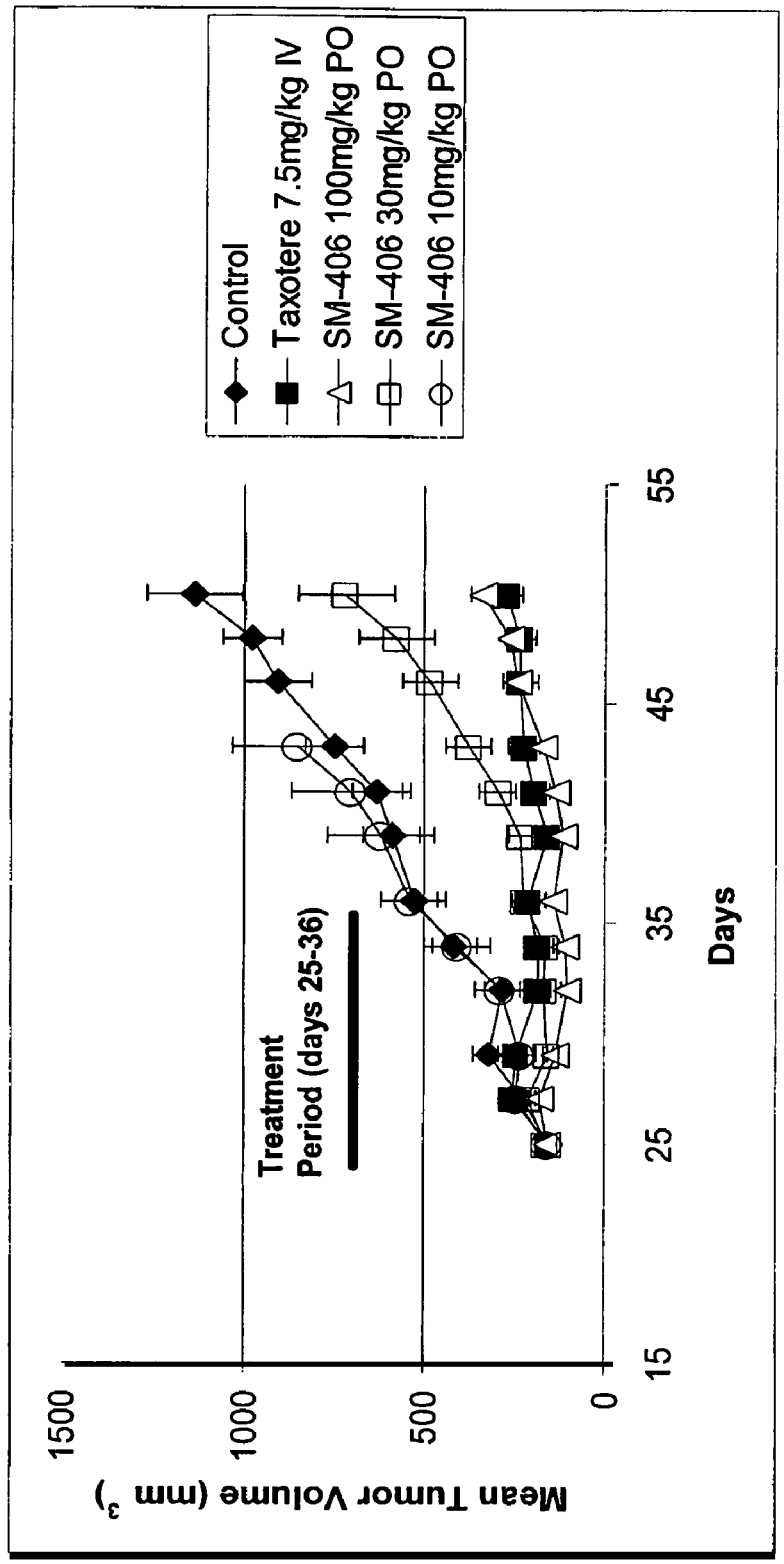
FIG. 25 is a graph illustrating the inhibition of tumor growth by SM-406 in the MDA-MB-231 xenograft model of human breast cancer in severe combined immunodeficient (SCID) mice.

The ability of SM-406 to act as an anti-tumor agent was tested in the MDA-MB-231 xenograft model of human breast cancer in severe combined immunodeficient (SCID) mice. Treatment started when tumors grew to average size of 150 mm$^3$. SM-406 was given daily, 5 days a week for 2 weeks via oral gavage. Taxotere was given intravenously (i.v.) once a week for 2 weeks. As illustrated in FIG. 25, SM-406 displayed anti-tumor activity at 30 and 100 mg/kg PO.

EXAMPLE 81

Anti-tumor Activity of SM-406 in PC-3 Xenograft Model

Figure 26:
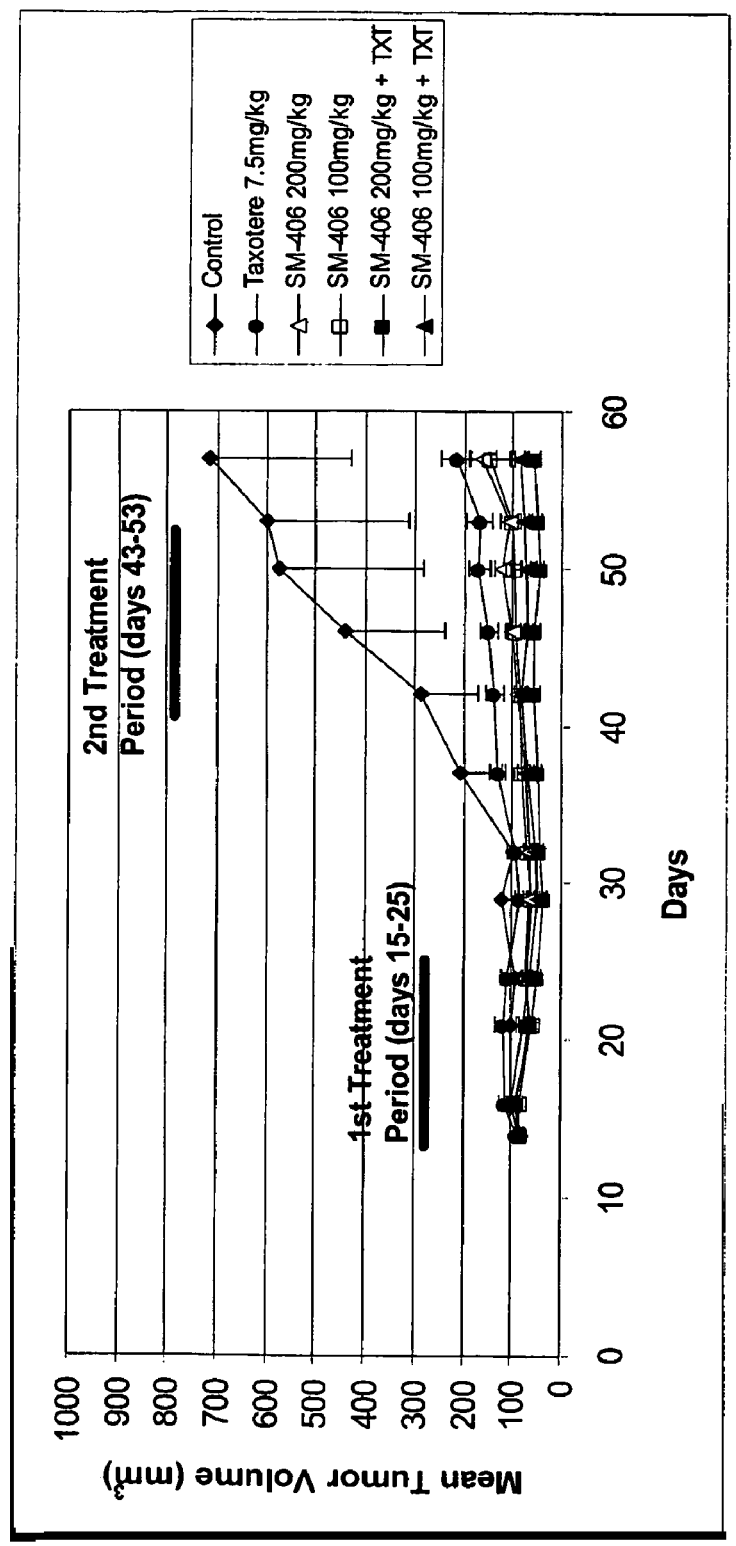
FIG. 26 is a graph illustrating the inhibition of tumor growth by SM-406 in the PC-3 xenograft model of human prostate cancer in nude mice.

The ability of SM-406 to act as an anti-tumor agent was tested in the PC-3 xenograft model of human prostate cancer in nude mice. Treatment started when tumors grew to average size of 100 mm$^3$. SM-406 was given daily, 5 days a week for 2 weeks via oral gavage between days 15-25 and for another 2 weeks between days 43-53. Taxotere was given intravenously (i.v.) once a week for 3 weeks at day 16, 23 and 44. As illustrated in FIG. 26, SM-406 alone or in combination with taxotere displayed anti-tumor activity.

EXAMPLE 82

Anti-tumor Activity of SM-406 in 2LMP Xenograft Model

Figure 27:
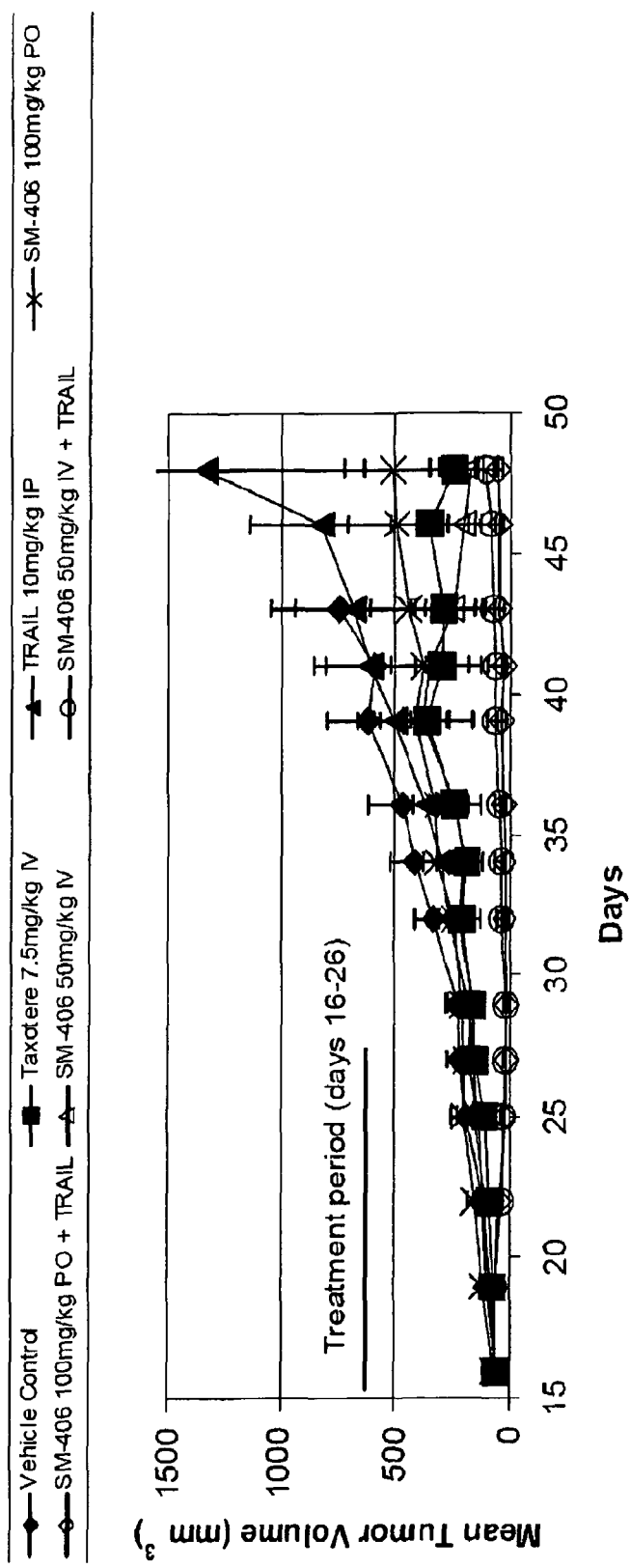
FIG. 27 is a graph illustrating the inhibition of tumor growth by SM-406 in the 2LMP xenograft model of human breast cancer in nude mice.

The ability of SM-406 to act as an anti-tumor agent was tested in the 2LMP xenograft model of human breast cancer in nude mice. SM-406 was given daily for 10 days either intraperitoneal (i.p.) or orally (p.o.) between days 16-26. Taxotere was given intravenously (i.v.) once a week for 2 weeks. Tumor necrosis factor (TNF)-related apoptosis-inducing ligand (TRAIL) was i.p. once a day for 10 days between days 16-26. As illustrated in FIG. 27, SM-406 alone or in combination with TRAIL displayed anti-tumor activity.

EXAMPLE 83

Binding of SM-406 to BIR3 Domains of IAP Proteins

Figure 28:
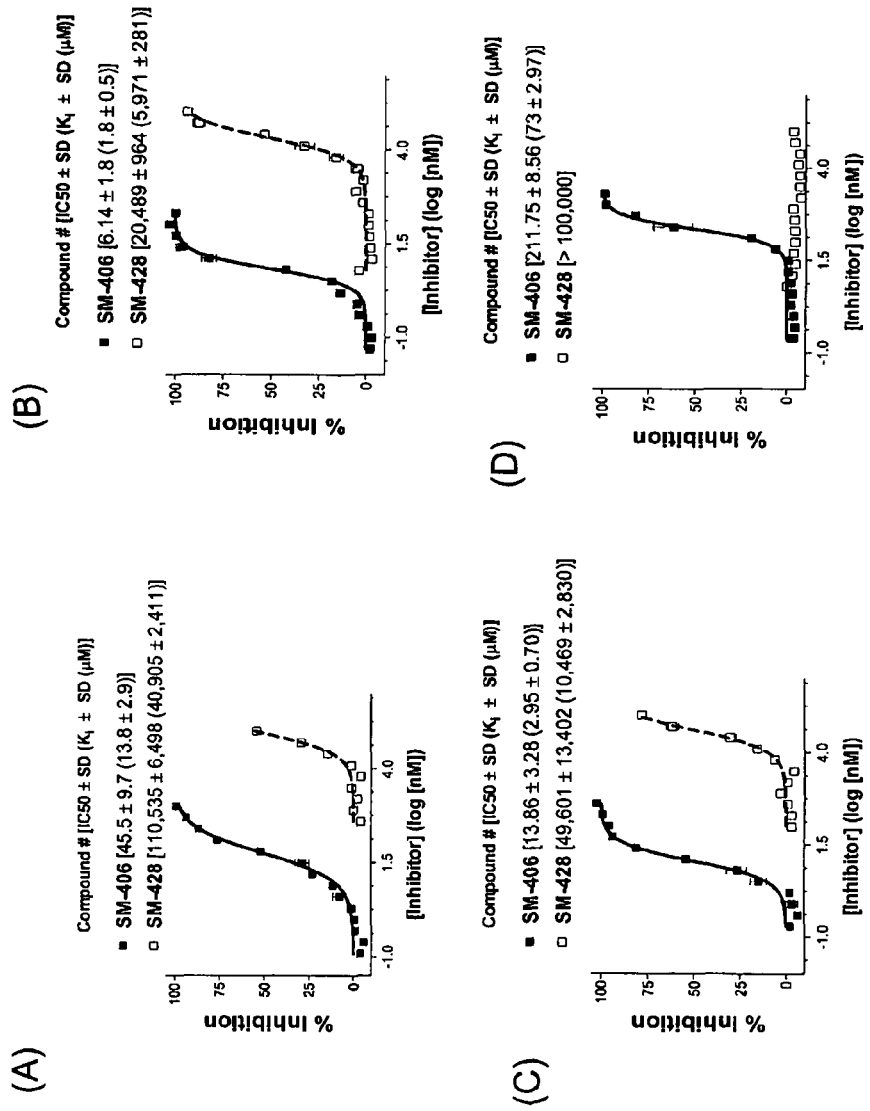
FIG. 28 is a series of graphs illustrating the competitive binding curves SM-406 and SM-428 to BIR3 domains of four members of IAPs proteins ((A) XIAP; (B) cIAP1; (C) cIAP2; (D) ML-IAP) as determined using a fluorescence-polarization-based binding assay.

The competitive binding curves of SM-406 and SM-428 to BIR$^3$ domains of four members of IAP proteins were determined using a fluorescence-polarization-based binding assay. The IAP proteins tested include: (A) XIAP; (B) cIAP1; (C) cIAP2; (D) ML-IAP. As illustrated in FIG. 28, SM-406 binds to all four IAP proteins.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:
1. A compound selected from the group consisting of:
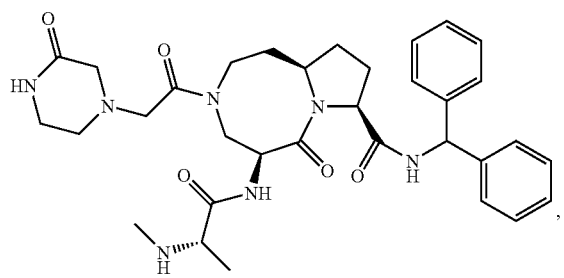
,
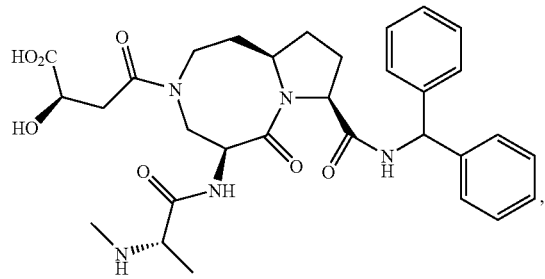
,
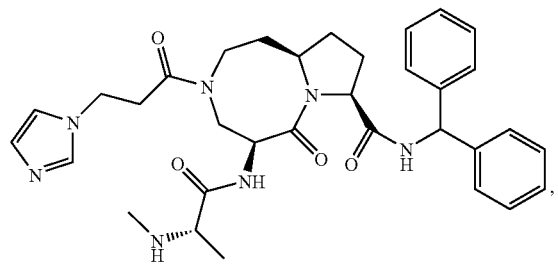
,
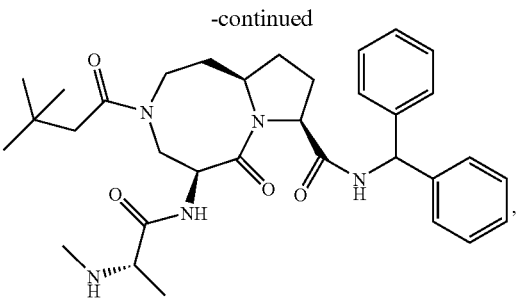
,
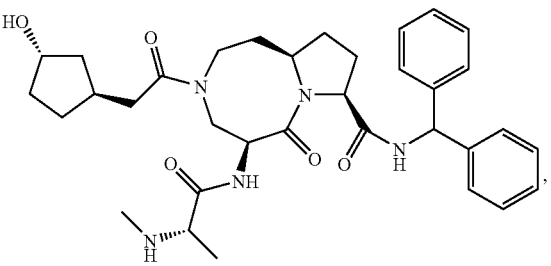
,
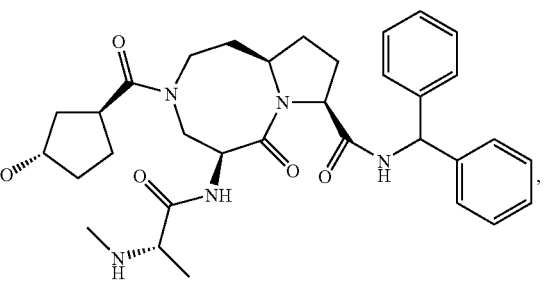
,

109
-continued
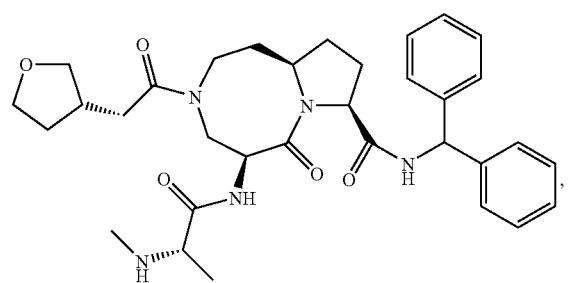
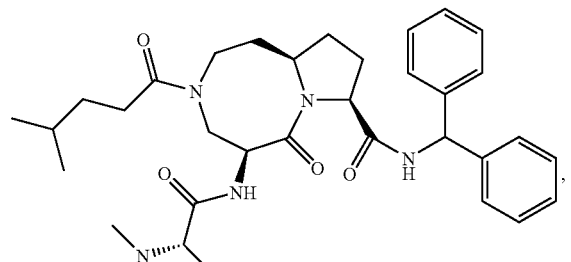
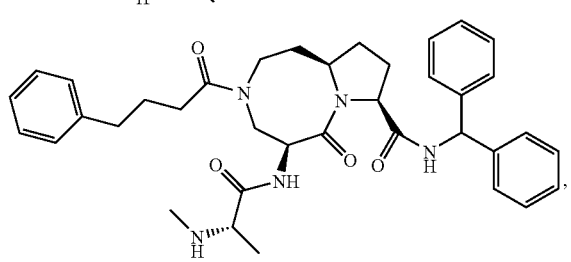
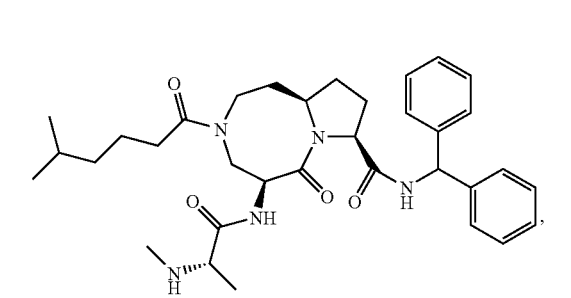
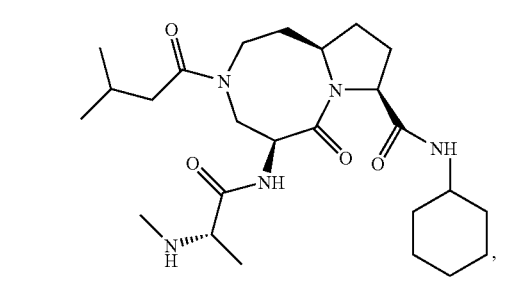
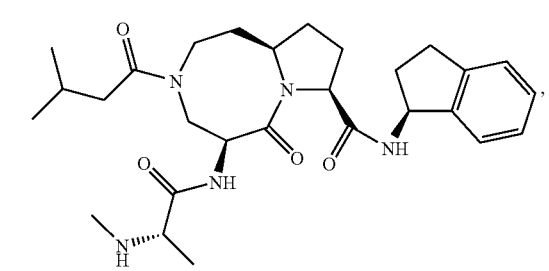
110
-continued
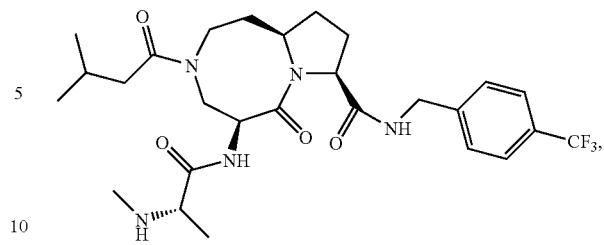
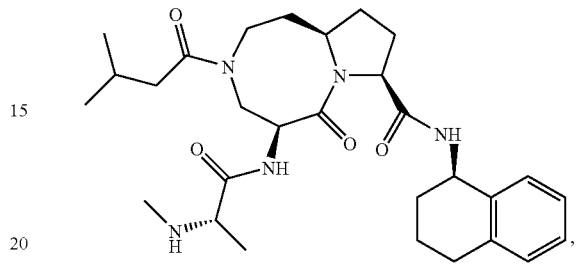
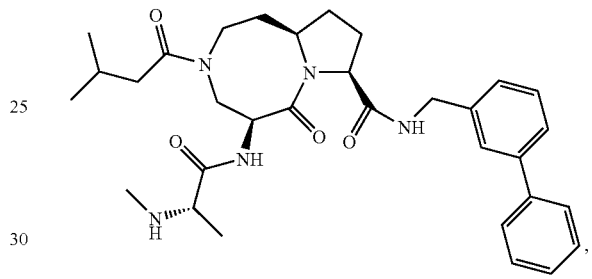
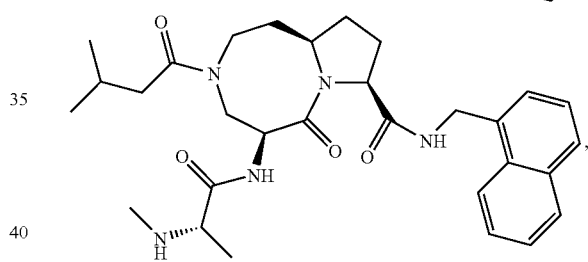
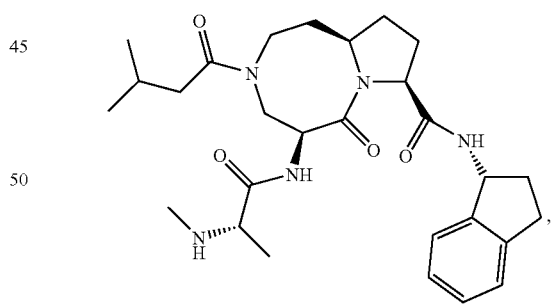
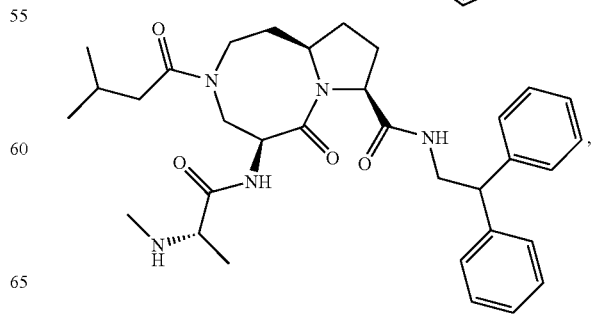

111
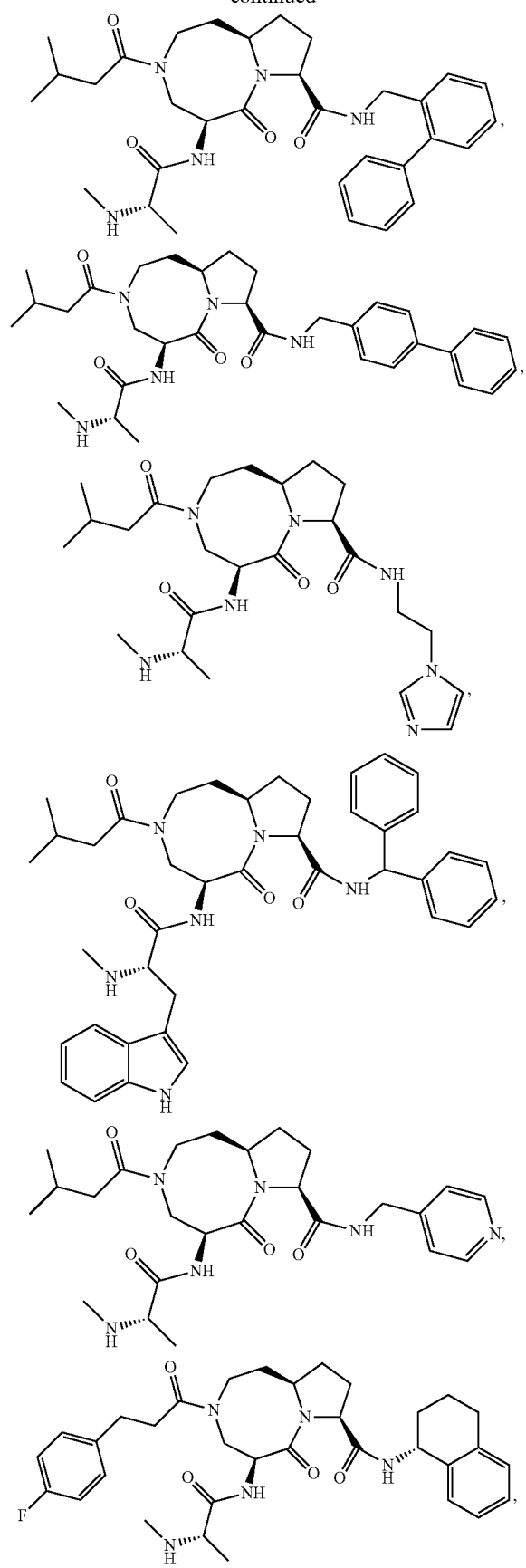
112
-continued
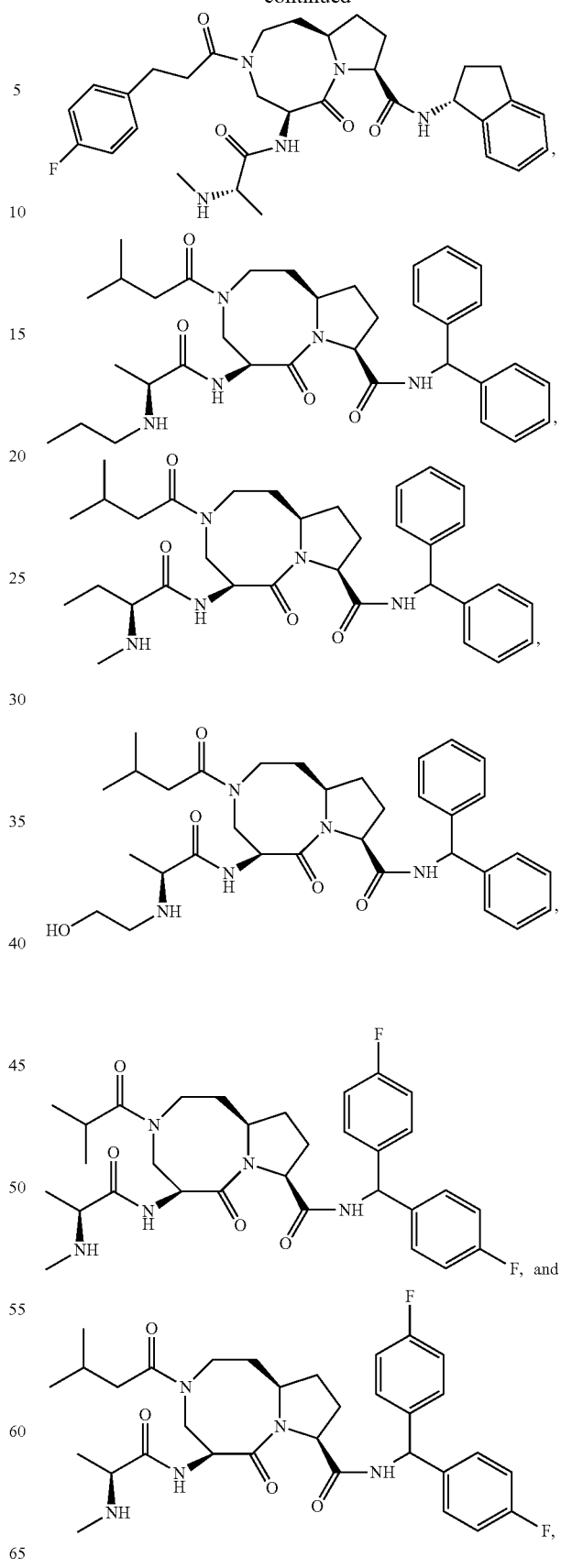
or a pharmaceutically acceptable salt thereof.

2. A compound selected from the group consisting of:
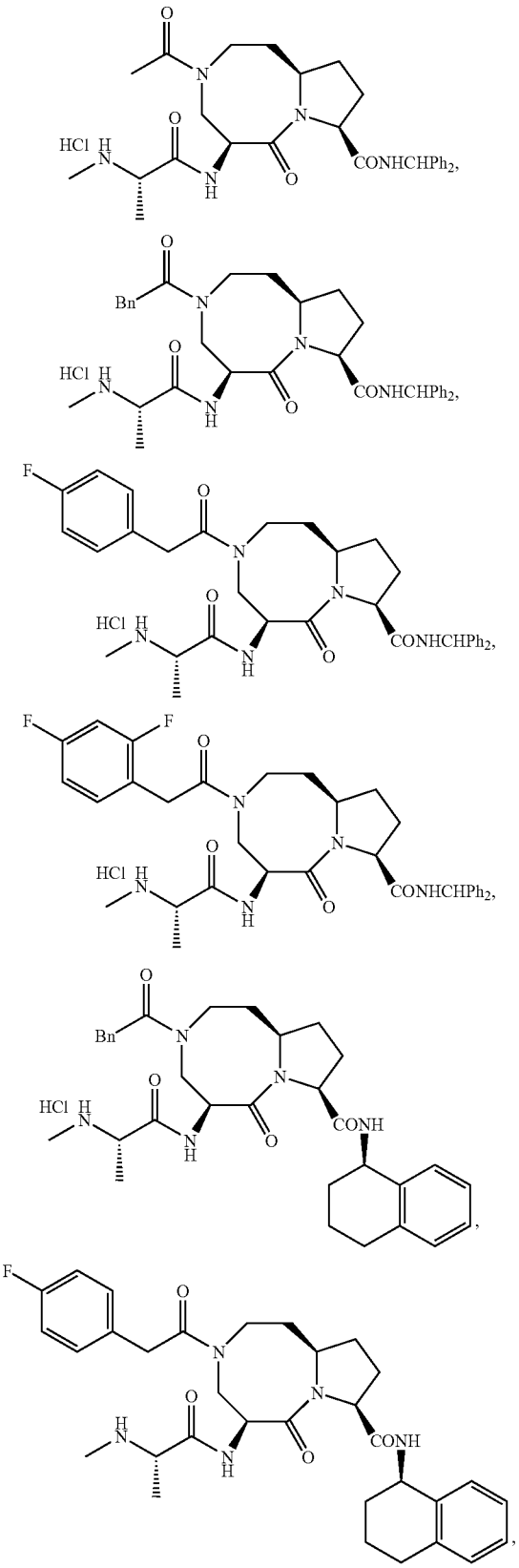
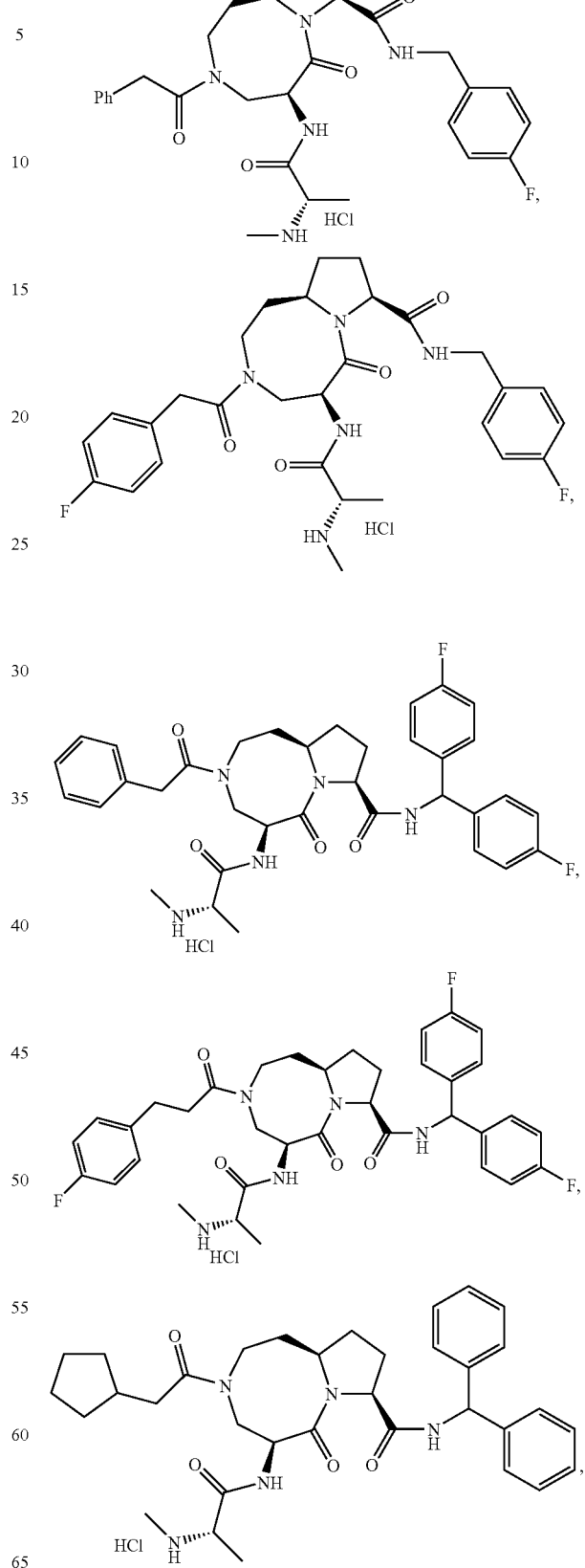

-continued

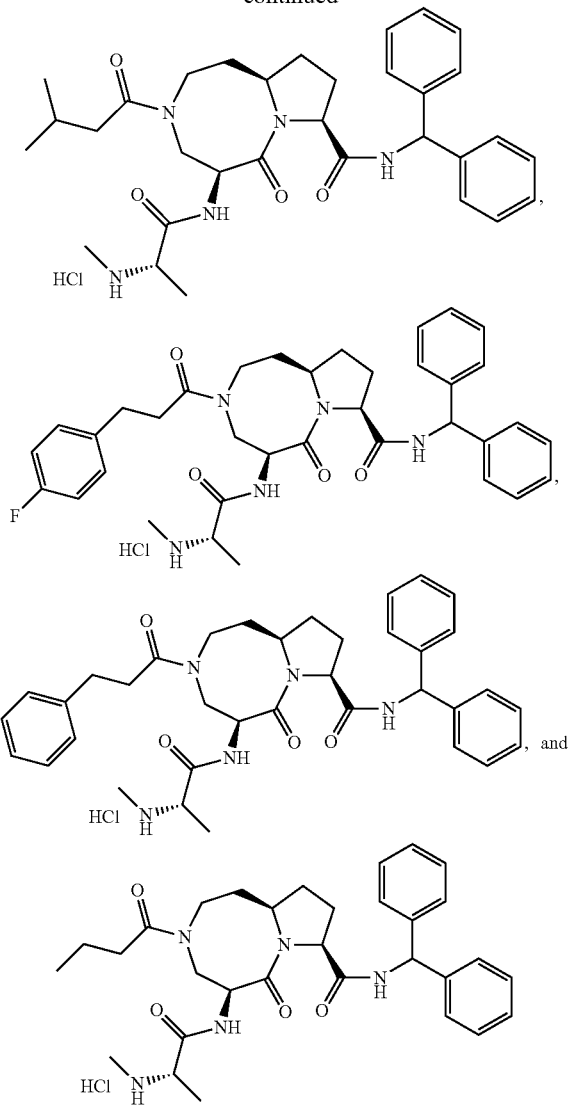

or the free base thereof or another pharmaceutically acceptable salt thereof.

3. A compound of formula:

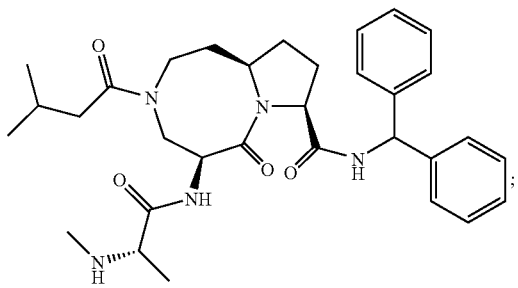

or a pharmaceutically acceptable salt thereof.

4. A pharmaceutical composition comprising the compound of claim 3, or a pharmaceutically acceptable salt thereof, and a pharmaceutically acceptable carrier.

5. A process for preparing a compound of Formula XI

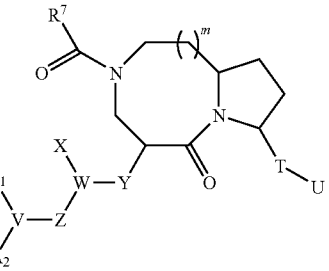

XI wherein
$A_1$ and $A_2$ are independently selected from the group consisting of hydrogen and optionally substituted alkyl;
V is selected from the group consisting of N;
W is selected from the group consisting of CH;
X is selected from the group consisting of hydrogen and optionally substituted $C_{1-3}$ alkyl;
Y is NHCO where NH is connected to the ring and CO is connected to W;
T is C=O;
U is $NR^1R^2$;
Z is $(CR^1R^2)_r$, wherein r is 0;
m is 1;
each of $R^1$ and $R^2$ are independently selected from the group consisting of hydrogen, optionally substituted alkyl, optionally substituted carbocyclic, optionally substituted heterocyclic, optionally substituted aryl and optionally substituted heteroaryl; and
$R^7$ is selected from the group consisting of hydrogen, optionally substituted alkyl, optionally substituted carbocyclic, optionally substituted heterocyclic, optionally substituted aryl and optionally substituted heteroaryl;
comprising condensing a compound of Formula XII

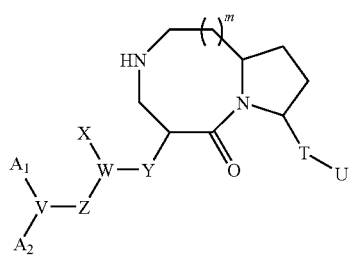

XII wherein $A_1$, $A_2$, V, W, X, Y, T, U and m have the meanings described above for Formula XI;
with $R^7$CO-L, and
L is a leaving group, to form a compound of Formula XI.

* * * * *